US009551041B2

(12) United States Patent
Luck et al.

(10) Patent No.: US 9,551,041 B2
(45) Date of Patent: Jan. 24, 2017

(54) GENETIC LOCI ASSOCIATED WITH FUSARIUM EAR MOLD RESISTANCE IN MAIZE

(71) Applicants: E I DU PONT DE NEMOURS AND COMPANY, Wilmington, DE (US); PIONEER HI BRED INTERNATIONAL INC, Johnston, IA (US)

(72) Inventors: Stanley Luck, Wilmington, DE (US); Dario Prada, Cremona (IT); Kevin Simcox, West Des Moines, IA (US); Adriana Tomas, Newark, DE (US)

(73) Assignees: E I DU PONT DE NEMOURS AND COMPANY, Wilmington, DE (US); PIONEER HI BRED INTERNATIONAL INC, Johnston, IA (US)

( * ) Notice: Subject to any disclaimer, the term of this patent is extended or adjusted under 35 U.S.C. 154(b) by 455 days.

(21) Appl. No.: 14/191,477

(22) Filed: Feb. 27, 2014

(65) Prior Publication Data

US 2014/0237679 A1 Aug. 21, 2014

Related U.S. Application Data

(62) Division of application No. 12/759,178, filed on Apr. 13, 2010, now Pat. No. 8,697,942.

(60) Provisional application No. 61/168,779, filed on Apr. 13, 2009.

(51) Int. Cl.
*C12Q 1/68* (2006.01)
*A01H 1/04* (2006.01)
*A01H 5/10* (2006.01)
*C12N 15/82* (2006.01)

(52) U.S. Cl.
CPC .............. *C12Q 1/6895* (2013.01); *A01H 1/04* (2013.01); *A01H 5/10* (2013.01); *C12N 15/8282* (2013.01); *C12Q 2600/156* (2013.01)

(58) Field of Classification Search
None
See application file for complete search history.

(56) References Cited

FOREIGN PATENT DOCUMENTS

| WO | 2008/087208 | 7/2008 |
|----|-------------|---------|
| WO | 2008/128761 | 10/2008 |
| WO | 2008/143993 | 11/2008 |

OTHER PUBLICATIONS

Jun-Qiang Ding et al., QTL mapping of resistance of Fusarium ear rot using a RIL population in maize, Molecular Breeding, 2008, pp. 395-403, vol. 22.
Keith E. Duncan et al. Biology of Maize Kernel Infection by Fusarium verticillioides, Molecular Plant-Microbe Interactions, 2010, pp. 6-16, vol. 23, No. 1.
Jon Duvick, Prospects for Reducing Fumonisin Contamination of Maize through Genetic Modification, Environmental Health Perspectives, May 2001, pp. 337-342, vol. 109.
E. Frascaroli et al., Allelic Frequency Change of P1 Gene in a Maize Population After Recurrent Selection for Grain Yield, Crop Science, 1998, pp. 1391-1394, vol. 38.
Daisy Perez-Brito et al., QTL Mapping of Fusarium moniliforme Ear Rot Resistance in Highland Maize, Mexico, Agrociencia, 2001, pp. 181-196, vol. 35, No. 2.
Leilani A. Robertson-Hoyt et al., QTL Mapping for Fusarium Ear Rot and Fumonisin Contamination Resistance in Two Maize Populations, Crop Science, 2006, pp. 1734-1743, vol. 46.
Leilani A. Robertson-Hoyt et al., Relationships of Resistance to Fusarium Ear Rot and Fumonisin Contamination with Agronomic performance of Maize, Crop Science, 2007, pp. 1770-1778, vol. 47.
Leilani A. Robertson-Hoyt et al., Relationships Among Resistances to Fusarium and Aspergillus Ear Rots and Contamination by Fumonisin and Aflatoxin in Maize, Phytopathology, pp. 311-317, vol. 97.
Nathan J. Vanopdorp, Predicted QTL Locations for Fusarium Ear Rot (FER) Resistance in Maize and the Generation of Improved FER Resistant Maize Inbred Lines, Disseration Purdue University, May 2009, 57 pages, AAT 1469941.
Randall J. Wisser et al., The Genetic Architecture of Disease Resistance in Maize: A Synthesis of Published Studies, Phytopathology, 2006, pp. 120-129, vol. 96(2).
Fan Zhang et al., QTL mapping of Fusarium moniliforme ear rot resistance in maize. 1. map construction with microsatellite and AFLP markers, J. Appl. Genet., 206, pp. 9-15, vol. 47(1).
Fan Zhang et al., Molecular Mapping of QTL for Resistance to Maize Ear Rot Caused by Fusarium moniliforme, Acta Agronomics Sinica, 2007, pp. 491-496, vol. 33(3).

*Primary Examiner* — Amjad Abraham
*Assistant Examiner* — Bratislav Stankovic

(57) ABSTRACT

The invention relates to methods and compositions for identifying and selecting maize plants with enhanced resistance to *Fusarium* ear mold. Maize plants generated by the methods of the invention are also a feature of the invention.

2 Claims, 24 Drawing Sheets

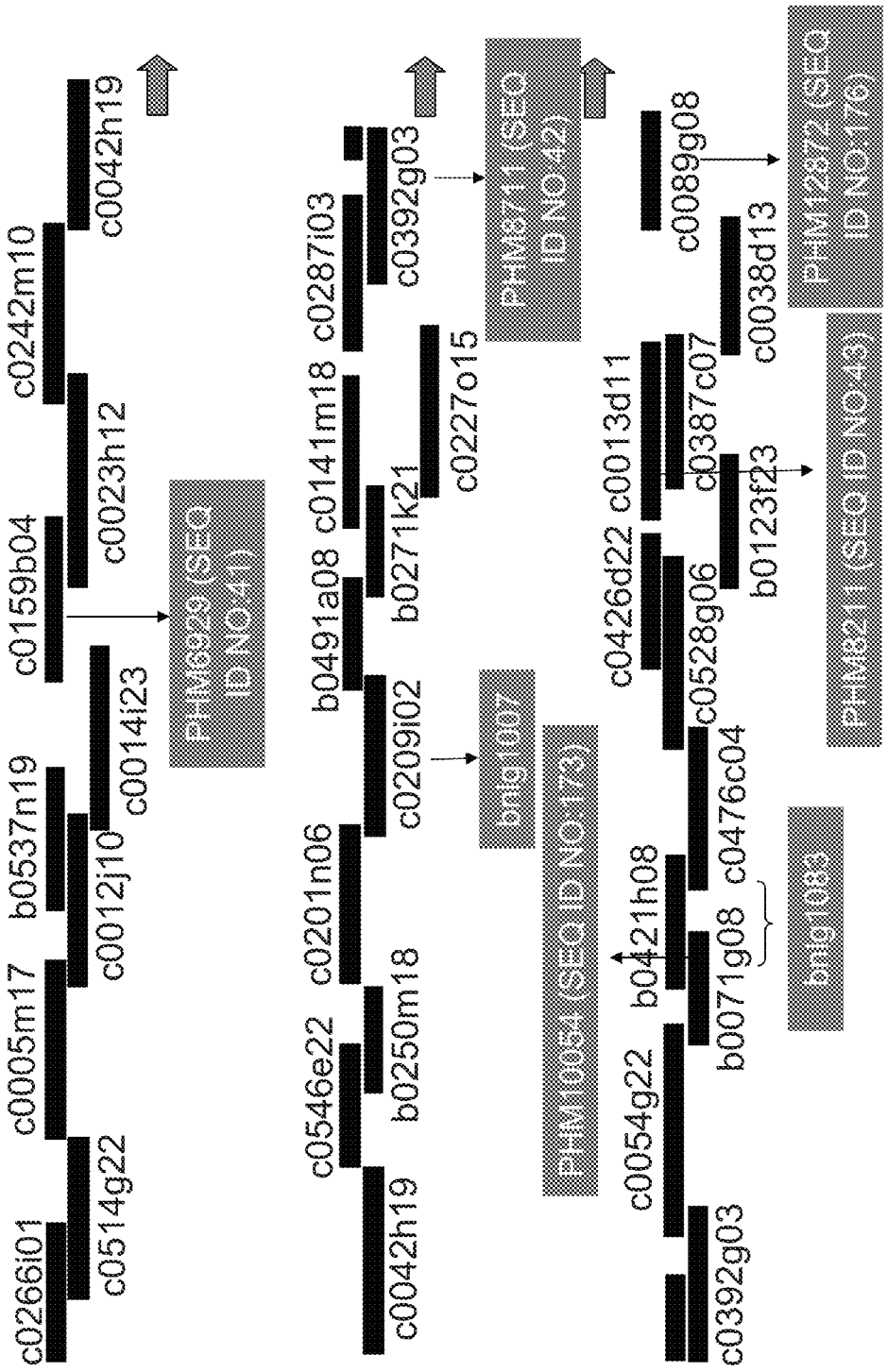
FIG. 1A Chromosome 1 QTL

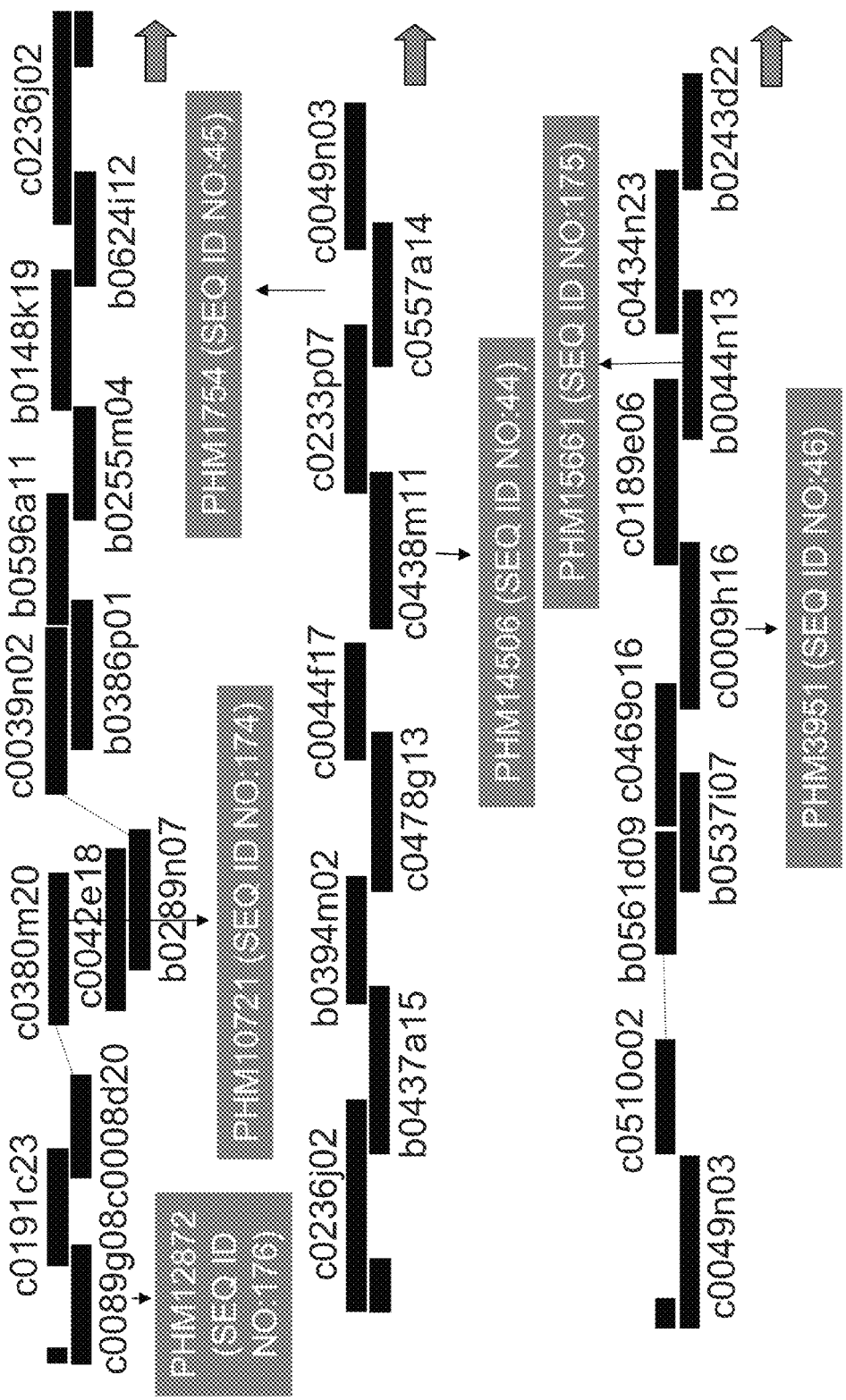
FIG. 1B Chromosome 1 QTL

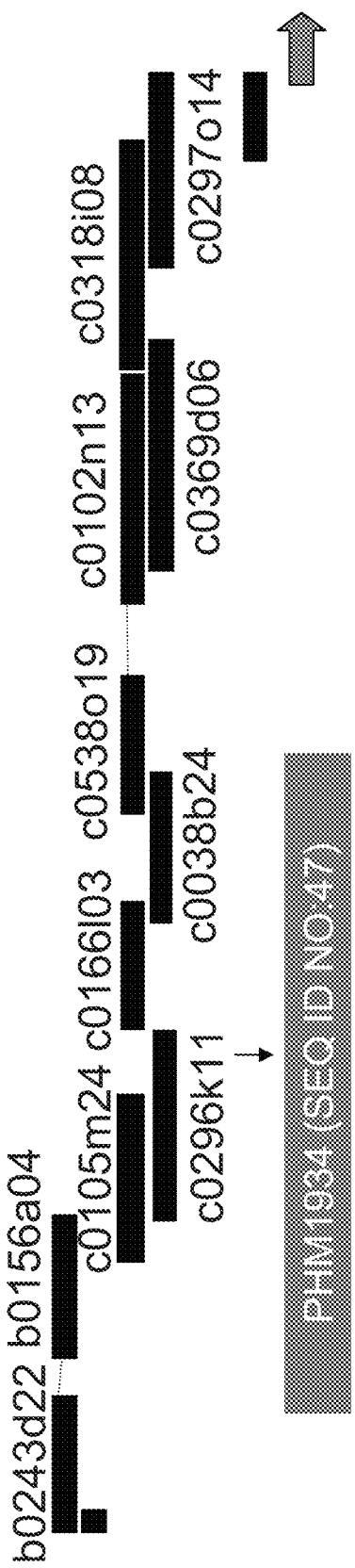

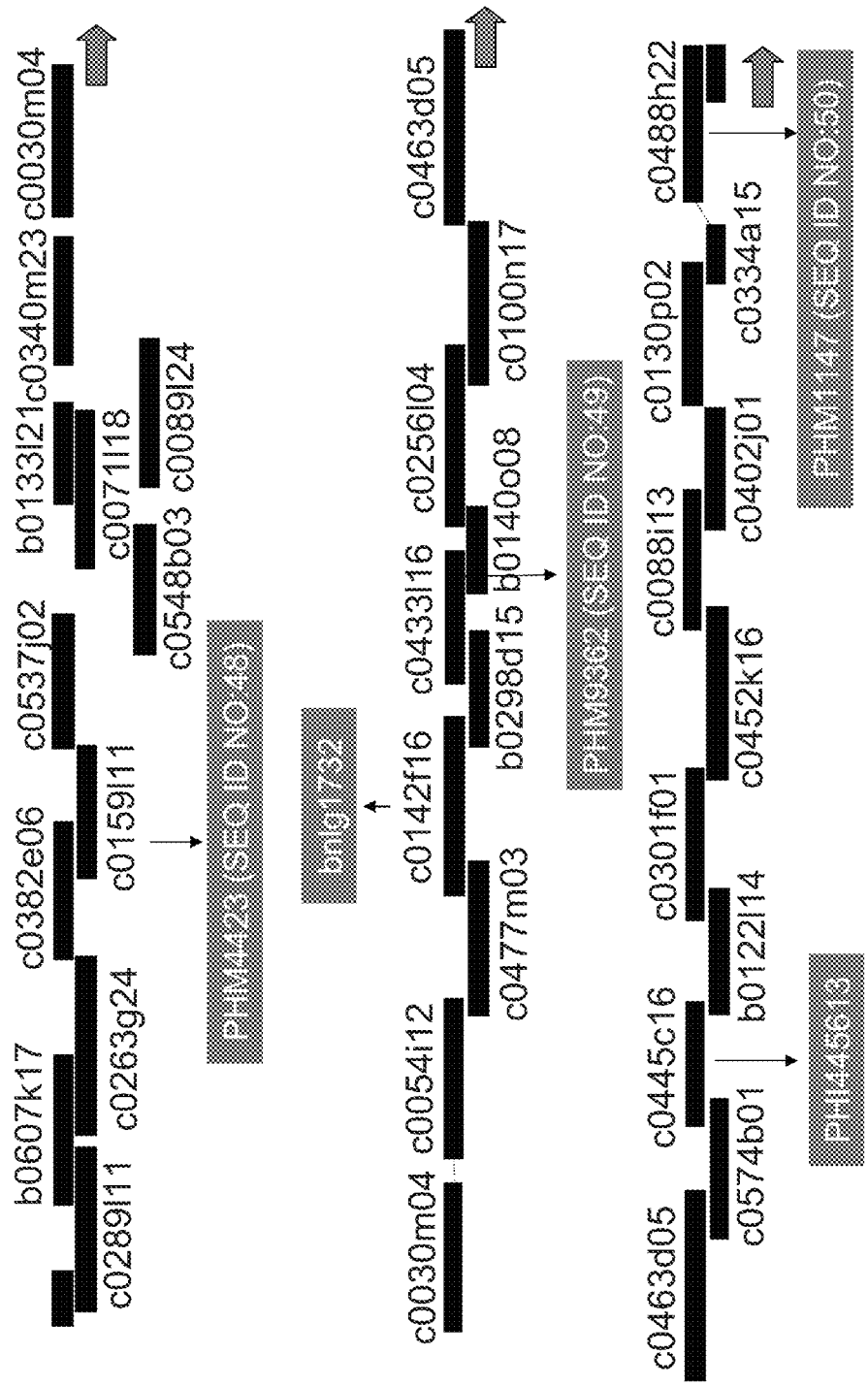
FIG. 2A Chromosome 6 QTL

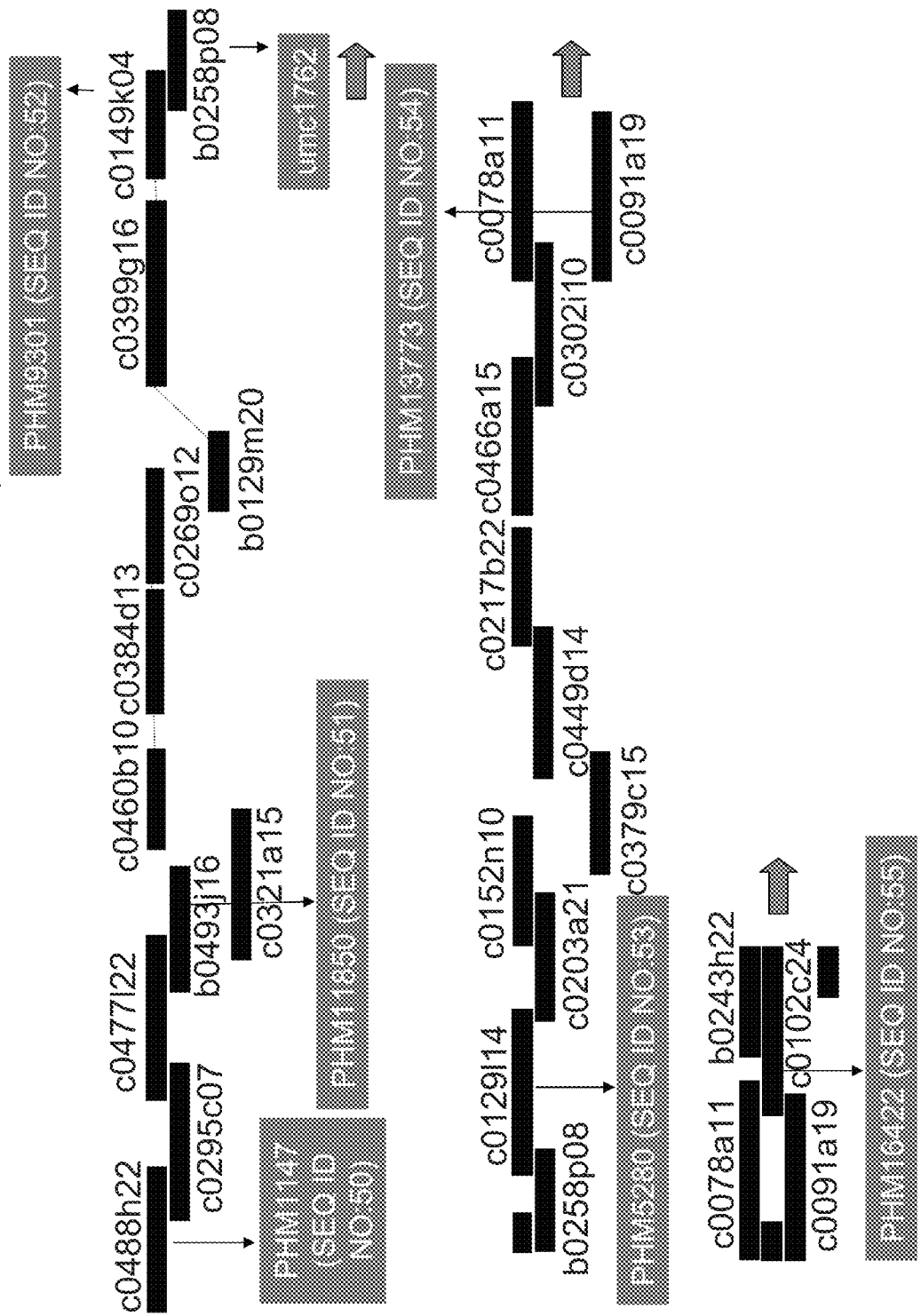
FIG. 2B Chromosome 6 QTL

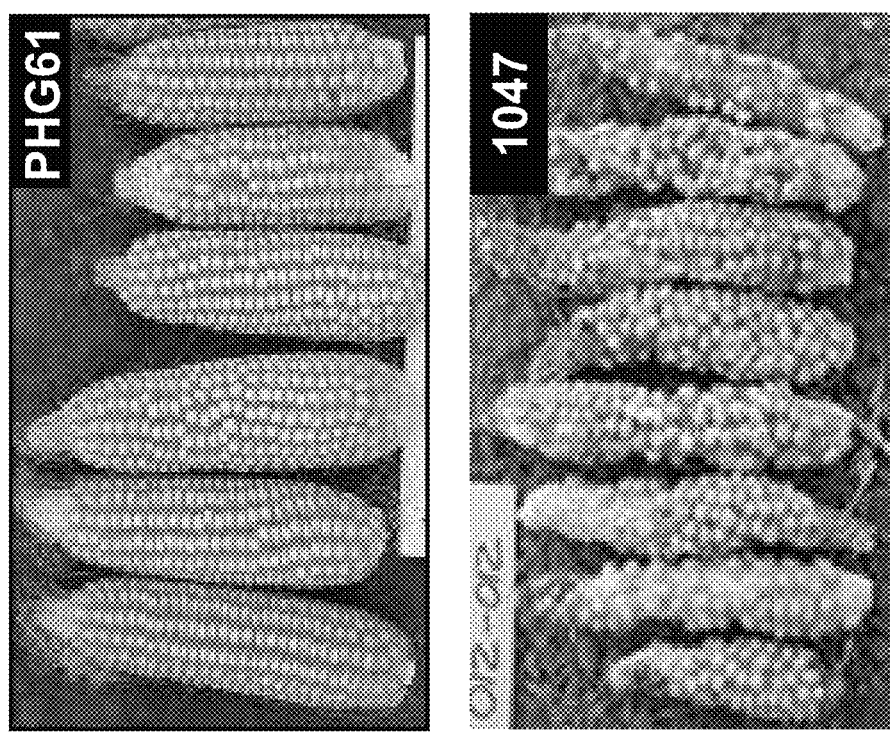
FIG. 3 Comparison between PHG61 and 1047

FIG. 4 FUSERS scale for ear pile

| | |
|---|---|
| 9 | No kernels show starburst or are moldy. |
| 8 | Fewer than 10% of kernels show starburst, no moldy kernels. |
| 7 | Between 10-20% of kernels show starburst, no moldy kernels. |
| 6 | Between 20-50% of kernels show starburst, no moldy kernels. |
| 5 | Between 51-75% of kernels show starburst, no moldy kernels. |
| 4 | Between 76-100% of kernels show starburst and fewer than 50% of kernels are moldy. |
| 3 | Between 76-100% of kernels show starburst and between 50-75% of kernels are moldy. |
| 2 | Between 76-100% of kernels show starburst and between 76-90% of kernels are moldy. |
| 1 | All ears in the pile are mummified, less than 10% of kernels are recognizable. |

FIG. 5A SNP markers for use with Invader Plus platform – QTL1

| Marker Name | PHM6929-3-U | PHM8711-14-U | PHM8211-16-I |
|---|---|---|---|
| SNP Name | PHM6929-3 | PHM8711-14 | PHM8211-16 |
| PRIMER1_F_SEQ | SEQ ID NO:65 | SEQ ID NO:69 | SEQ ID NO:73 |
| PRIMER1_R_SEQ | SEQ ID NO:66 | SEQ ID NO:70 | SEQ ID NO:74 |
| SENSE | SENSE | SENSE | SENSE |
| ALLELE1 | T | T | T |
| ALLELE2 | C | C | G |
| DYE1 | FAM | FAM | FAM |
| DYE2 | RED | RED | RED |
| PROBE_1_SEQ | SEQ ID NO:67 | SEQ ID NO:71 | SEQ ID NO:75 |
| PROBE_2_SEQ | SEQ ID NO:68 | SEQ ID NO:72 | SEQ ID NO:76 |

| Marker Name | PHM14506-7-U | PHM1754-20-U | PHM3951-25-U |
|---|---|---|---|
| SNP Name | PHM14506-7 | PHM1754-20 | PHM3951-25 |
| PRIMER1_F_SEQ | SEQ ID NO:77 | SEQ ID NO:81 | SEQ ID NO:85 |
| PRIMER1_R_SEQ | SEQ ID NO:78 | SEQ ID NO:82 | SEQ ID NO:86 |
| SENSE | ANTI-SENSE | ANTI-SENSE | SENSE |
| ALLELE1 | C | C | C |
| ALLELE2 | T | T | T |
| DYE1 | FAM | FAM | FAM |
| DYE2 | RED | RED | RED |
| PROBE_1_SEQ | SEQ ID NO:79 | SEQ ID NO:83 | SEQ ID NO:87 |
| PROBE_2_SEQ | SEQ ID NO:80 | SEQ ID NO:84 | SEQ ID NO:88 |

FIG. 5B SNP markers for use with Invader Plus platform – QTL1

| Marker Name | PHM1934-37-U | PHM8711-17-U | PHM10054-14-U |
|---|---|---|---|
| SNP Name | PHM1934-37 | PHM8711-17 | PHM10054-14 |
| PRIMER1_F_SEQ | SEQ ID NO:89 | SEQ ID NO:177 | SEQ ID NO:181 |
| PRIMER1_R_SEQ | SEQ ID NO:90 | SEQ ID NO:178 | SEQ ID NO:182 |
| SENSE | ANTI-SENSE | SENSE | SENSE |
| ALLELE1 | C | T | G |
| ALLELE2 | A | C | A |
| DYE1 | FAM | FAM | FAM |
| DYE2 | RED | RED | RED |
| PROBE_1_SEQ | SEQ ID NO:91 | SEQ ID NO:179 | SEQ ID NO:183 |
| PROBE_2_SEQ | SEQ ID NO:92 | SEQ ID NO:180 | SEQ ID NO:184 |

| Marker Name | PHM10721-9-U | PHM10721-16-U | PHM15661-21-U |
|---|---|---|---|
| SNP Name | PHM10721-9 | PHM10721-16 | PHM15661-21 |
| PRIMER1_F_SEQ | SEQ ID NO:185 | SEQ ID NO:189 | SEQ ID NO:193 |
| PRIMER1_R_SEQ | SEQ ID NO:186 | SEQ ID NO:190 | SEQ ID NO:194 |
| SENSE | SENSE | ANTI-SENSE | SENSE |
| ALLELE1 | A | A | A |
| ALLELE2 | G | G | G |
| DYE1 | FAM | FAM | FAM |
| DYE2 | RED | RED | RED |
| PROBE_1_SEQ | SEQ ID NO:187 | SEQ ID NO:191 | SEQ ID NO:195 |
| PROBE_2_SEQ | SEQ ID NO:188 | SEQ ID NO:192 | SEQ ID NO:196 |

FIG. 6A SNP markers for use with Invader Plus platform – QTL6

| Marker Name | PHM4423-4-U | PHM9362-8-U | PHM1147-16-U |
|---|---|---|---|
| SNP Name | PHM4423-4 | PHM9362-8 | PHM1147-16 |
| PRIMER1_F_SEQ | SEQ ID NO:93 | SEQ ID NO:97 | SEQ ID NO:101 |
| PRIMER1_R_SEQ | SEQ ID NO:94 | SEQ ID NO:98 | SEQ ID NO:102 |
| SENSE | SENSE | SENSE | ANTI-SENSE |
| ALLELE1 | T | A | G |
| ALLELE2 | C | G | A |
| DYE1 | FAM | FAM | FAM |
| DYE2 | RED | RED | RED |
| PROBE_1_SEQ | SEQ ID NO:95 | SEQ ID NO:99 | SEQ ID NO:103 |
| PROBE_2_SEQ | SEQ ID NO:96 | SEQ ID NO:100 | SEQ ID NO:104 |

| Marker Name | PHM1147-19-U | PHM11850-3-U | PHM11850-6-U |
|---|---|---|---|
| SNP Name | PHM1147-19 | PHM11850-3 | PHM11850-6 |
| PRIMER1_F_SEQ | SEQ ID NO:105 | SEQ ID NO:109 | SEQ ID NO:113 |
| PRIMER1_R_SEQ | SEQ ID NO:106 | SEQ ID NO:110 | SEQ ID NO:114 |
| SENSE | ANTI-SENSE | ANTI-SENSE | SENSE |
| ALLELE1 | C | T | T |
| ALLELE2 | T | C | C |
| DYE1 | FAM | FAM | FAM |
| DYE2 | RED | RED | RED |
| PROBE_1_SEQ | SEQ ID NO:107 | SEQ ID NO:111 | SEQ ID NO:115 |
| PROBE_2_SEQ | SEQ ID NO:108 | SEQ ID NO:112 | SEQ ID NO:116 |

FIG. 6B SNP markers for use with Invader Plus platform – QTL6

| Marker Name | PHM9301-37-U | PHM5280-41-U | PHM13773-6-U |
|---|---|---|---|
| SNP Name | PHM9301-37 | PHM5280-41 | PHM13773-6 |
| PRIMER1_F_SEQ | SEQ ID NO:117 | SEQ ID NO:121 | SEQ ID NO:125 |
| PRIMER1_R_SEQ | SEQ ID NO:118 | SEQ ID NO:122 | SEQ ID NO:126 |
| SENSE | SENSE | ANTI-SENSE | SENSE |
| ALLELE1 | T | G | A |
| ALLELE2 | C | A | G |
| DYE1 | FAM | FAM | FAM |
| DYE2 | RED | RED | RED |
| PROBE_1_SEQ | SEQ ID NO:119 | SEQ ID NO:123 | SEQ ID NO:127 |
| PROBE_2_SEQ | SEQ ID NO:120 | SEQ ID NO:124 | SEQ ID NO:128 |

| Marker Name | PHM13773-11-U | PHM16422-11-U |
|---|---|---|
| SNP Name | PHM13773-11 | PHM16422-11 |
| PRIMER1_F_SEQ | SEQ ID NO:129 | SEQ ID NO:133 |
| PRIMER1_R_SEQ | SEQ ID NO:130 | SEQ ID NO:134 |
| SENSE | SENSE | ANTI-SENSE |
| ALLELE1 | T | C |
| ALLELE2 | C | A |
| DYE1 | FAM | FAM |
| DYE2 | RED | RED |
| PROBE_1_SEQ | SEQ ID NO:131 | SEQ ID NO:135 |
| PROBE_2_SEQ | SEQ ID NO:132 | SEQ ID NO:136 |

FIG. 7A SNP markers for use with Invader Plus platform – QTL5

| Marker Name | PHM9009-13-U | PHM3171-5-U | PHM3860-43-U |
|---|---|---|---|
| SNP Name | PHM9009-13 | PHM3171-5 | PHM3860-43 |
| PRIMER1_F_SEQ | SEQ ID NO:137 | SEQ ID NO:141 | SEQ ID NO:145 |
| PRIMER1_R_SEQ | SEQ ID NO:138 | SEQ ID NO:142 | SEQ ID NO:146 |
| SENSE | SENSE | SENSE | ANTI-SENSE |
| ALLELE1 | T | A | A |
| ALLELE2 | C | G | G |
| DYE1 | FAM | FAM | FAM |
| DYE2 | RED | RED | RED |
| PROBE_1_SEQ | SEQ ID NO:139 | SEQ ID NO:143 | SEQ ID NO:147 |
| PROBE_2_SEQ | SEQ ID NO:140 | SEQ ID NO:144 | SEQ ID NO:148 |

FIG. 7B SNP markers for use with Invader Plus platform – QTL7

| Marker Name | PHM7942-12-U | PHM678-22-U | PHM8358-17-U |
|---|---|---|---|
| SNP Name | PHM7942-12 | PHM678-22 | PHM8358-17 |
| PRIMER1_F_SEQ | SEQ ID NO:149 | SEQ ID NO:153 | SEQ ID NO:157 |
| PRIMER1_R_SEQ | SEQ ID NO:150 | SEQ ID NO:154 | SEQ ID NO:158 |
| SENSE | SENSE | SENSE | ANTI-SENSE |
| ALLELE1 | C | C | G |
| ALLELE2 | T | A | C |
| DYE1 | FAM | FAM | FAM |
| DYE2 | RED | RED | RED |
| PROBE_1_SEQ | SEQ ID NO:151 | SEQ ID NO:155 | SEQ ID NO:159 |
| PROBE_2_SEQ | SEQ ID NO:152 | SEQ ID NO:156 | SEQ ID NO:160 |

FIG. 7C SNP markers for use with Invader Plus platform – QTL8

| Marker Name | PHM16415-8-U | PHM737-215-U | PHM9092-11-U |
|---|---|---|---|
| SNP Name | PHM16415-8 | PHM737-215 | PHM9092-11 |
| PRIMER1_F_SEQ | SEQ ID NO:161 | SEQ ID NO:165 | SEQ ID NO:169 |
| PRIMER1_R_SEQ | SEQ ID NO:162 | SEQ ID NO:166 | SEQ ID NO:170 |
| SENSE | SENSE | SENSE | SENSE |
| ALLELE1 | C | C | T |
| ALLELE2 | T | T | C |
| DYE1 | FAM | FAM | FAM |
| DYE2 | RED | RED | RED |
| PROBE_1_SEQ | SEQ ID NO:163 | SEQ ID NO:167 | SEQ ID NO:171 |
| PROBE_2_SEQ | SEQ ID NO:164 | SEQ ID NO:168 | SEQ ID NO:172 |

FIG. 8 PHCA5 conversion data

| Entry Name | SI_ID | corr_year mld | stddev | # of Reps | 1 PHM 8211 -16 | 1 PHM 3951 -25 | 6 PHM 9362 -8 | 6 PHM 1147 -19 | 6 PHM 11850 -6 | 6 PHM 5280 -41 | 6 PHM 9301 -37 | 5 PHM 9009 -13 | 5 PHM 3860 -43 | 7 PHM 7942 -12 | 7 PHM 8358 -17 | 8 PHM 16415 -8 | 8 PHM 737 -215 |
|---|---|---|---|---|---|---|---|---|---|---|---|---|---|---|---|---|---|
| PHG61 PHCA5 | 9785438 | | | | T | T | G | T | C | G | T | C | G | C | G | T | T |
| PHCA5FR1 | 11510073 | 4.0 | . | 1 | G | C | A | C | T | A | C | T | A | T | C | C | C |
| PHCA5FR1 | 11510074 | 4.0 | . | 1 | T | C,T | G | C | T | A | C | T | A | T | C | C | C |
| PHCA5FR3 | 11510082 | 4.0 | . | 1 | T | T | A | C | T | A | C | T | NF | T | NF | C | C |
| PHCA5FR4 | 11710275 | 4.0 | . | 1 | G | C | G | T | C | EQV | T | T | A | T | C | C | C |
| PHCA5FR4 | 11710277 | 5.5 | 0.7 | 2 | T | C,T | A | C | T | A | C | T | A | T | C | C | C |
| | | | | | T | C,T | G | C | T | A | C | T | A | T | C | C | C |

FIG. 9 PH51H conversion data

| Entry Name | SI_ID | corr_year mid | stdd ev | # of Reps | 1 PHM 8711 -17 | 1 PHM 8211 -16 | 1 PHM 1754 -20 | 1 PHM 3951 -25 | 6 PHM 9362 -8 | 6 PHM 1147 -16 | 6 PHM 1147 -19 | 6 PHM 11850 -6 | 6 PHM 9301 -37 | 5 PHM 9009 -13 | 7 PHM 7942 -12 | 7 PHM 8358 -17 | 8 PHM 16415 -8 | 8 PHM 9092 -11 |
|---|---|---|---|---|---|---|---|---|---|---|---|---|---|---|---|---|---|---|
| PHG61 | | | | | C | T | C | T | G | A | G | C | T | C | C | G | T | T |
| PH51H | 12030304 | 4.7 | 0.6 | 3 | T | G | T | C | A | A | C | T | C | T | T | C | C | C |
| PH51HFR2 | 11066809 | 5.5 | 0.7 | 2 | EQV | T | C,T | C,T | A,G | A | C | T | C | T | C,T | C,G | C | C |
| PH51HFR2 | 11066811 | 7.5 | 0.7 | 2 | T | G | T | C | A,G | A | C | T | C | T | T | C,G | C | C |
| PH51HFR2 | 11066837 | 5.0 | . | 1 | C,T | T | C,T | C,T | A,G | A | C | T | C | T | C | C,G | NF | NF |
| PH51HFR2 | 11066838 | 6.3 | 0.6 | 3 | C,T | T | C,T | C,T | NF | NF | NF | NF | NF | T | C,T | C,G | C | C |
| PH51HFR2 | 11066839 | 6.0 | . | 1 | C,T | T | C,T | C,T | A,G | A | C | T | C | T | C | C,G | C | C |
| PH51HFR2 | 11066841 | 6.7 | 0.6 | 3 | T | G | NF | C,T | A | A | C | T | NF | NF | NF | C,G | NF | NF |

FIG. 10 PH70R conversion data

| Entry Name | SI_ID | corr_year mld | stdd ev | # of Reps | 1 PHM 8211 -16 | 6 PHM 9362 -8 | 6 PHM 1147 -16 | 6 PHM 1147 -19 | 5 PHM 9009 -13 | 7 PHM 7942 -12 | 7 PHM 8358 -17 |
|---|---|---|---|---|---|---|---|---|---|---|---|
| PHG61 PH70R | 7230795 | 3.0 | 0.0 | 5 | T | G | G | T | C | C | G |
| PH70RFR3 | 11067135 | 3.0 | 0.0 | 2 | G | A | A | C | T | T | C |
| PH70RFR3 | 11067168 | 4.0 | . | 1 | G | G | G | T | T | T | C |
| PH70RFR2 | 11067060 | 5.0 | . | 1 | G,T | G | A,G | C,T | T | T | C |
| PH70RFR3 | 11067174 | 5.0 | 0.0 | 2 | T | G | G | T | T | T | C |
| PH70RFR3 | 11067126 | 5.5 | 2.1 | 2 | T | G | G | T | T | T | C |
| PH70RFR2 | 11067046 | 3.0 | 0.0 | 2 | T | A | A | C | T | T | C |
| PH70RFR3 | 11067139 | 3.5 | 0.7 | 2 | T | A,G | A,G | C,T | T | T | C |
| PH70RFR2 | 11067095 | 4.7 | 0.6 | 3 | T | A,G | A,G | C,T | T | T | C |
| PH70RFR3 | 11062329 | 5.0 | . | 1 | T | A,G | A,G | C,T | NF | T | C |

FIG. 11 PH87H conversion data

| Entry Name | SI_ID | corr_year mld | stddev | # of Reps | 1 PHM 8211 -16 | 1 PHM 1754 -20 | 1 PHM 3951 -25 | 6 PHM 9362 -8 | 6 PHM 1147 -19 | 6 PHM 11850 -6 | 6 PHM 5280 -41 | 6 PHM 9301 -37 | 5 PHM 9009 -13 | 5 PHM 3171 -5 | 5 PHM 3860 -43 | 7 PHM 7942 -12 | 7 PHM 8358 -17 | 8 PHM 16415 -8 | 8 PHM 737 -215 |
|---|---|---|---|---|---|---|---|---|---|---|---|---|---|---|---|---|---|---|---|
| PHG61 | | | | | | | | | | | | | | | | | | | |
| PH87H | 8816397 | 5.5 | 0.7 | 2 | T | C | C | G | T | C | G | T | C | G | G | C | G | T | T |
| PH87HFR3 | 11066328 | 3.7 | 0.6 | 3 | G | T | C | A | C | T | A | C | T | A | A | T | C | C,T | C,T |
| PH87HFR3 | 11066329 | 4.0 | 0.0 | 2 | T | C,T | C,T | A,G | C,T | T | A | C | C | G | G | T | C | C,T | T |
| PH87HFR3 | 11066314 | 4.0 | 0.0 | 2 | T | C | T | G | T | T | A | C | T | A | A,G | T | C | C,T | C,T |
| PH87HFR1 | 11066230 | 4.3 | 1.2 | 3 | G | T | C | A | C | T | A | C | C,T | G | G | T | C | C,T | T |
| PH87HFR1 | 11066235 | 6.0 | . | 1 | T | T | C | A | C | T | A | C | T | A | A | T | C | C | T |
| PH87HFR1 | 11066277 | 6.0 | . | 1 | T | T | C | A | C | T | A | C | T | A | A | T | C | C | T |
| PH87HFR3 | 11066377 | 6.0 | 1.4 | 2 | T | C,T | C,T | G | T | T | A | C | C,T | A,G | A,G | T | C | C | C |
| PH87HFR3 | 11062279 | 6.0 | 0.0 | 2 | T | C | T | NF | NF | NF | NF | C | C | G | G | T | C | C | C,T |
| PH87HFR3 | 11066321 | 6.0 | 0.8 | 4 | T | C | T | A,G | C,T | T | A | C | T | A,G | A,G | T | C | C,T | C,T |

FIG. 12 PHFCJ conversion data

| Entry Name | SL_ID | corr_year_mld | stddev | # of Reps | 1 PHM 8711 -17 | 1 PHM 1754 -20 | 1 PHM 3951 -25 | 6 PHM 1147 -19 | 6 PHM 11850 -6 | 6 PHM 5280 -41 | 5 PHM 9009 -13 | 5 PHM 3171 -5 | 5 PHM 3860 -43 | 7 PHM 7942 -12 | 7 PHM 678 -22 | 8 PHM 9092 -11 |
|---|---|---|---|---|---|---|---|---|---|---|---|---|---|---|---|---|
| PHG61 | | | | | C | C | T | T | C | G | C | G | G | C | C | T |
| PHFCJ | 8431393 | 5.3 | 1.3 | 4 | T | T | C | T | T | A | T | A | A | T | A | C |
| PHFCJFR4 | 11066486 | 3.7 | 0.6 | 3 | C,T | C,T | C,T | T | C | G | T | A | A | T | A | C |
| PHFCJFR4 | 11066514 | 4.0 | 1.0 | 3 | NF | C | T | T | C | G | T | A | NF | T | A | C |
| PHFCJFR4 | 11066522 | 4.0 | 0.0 | 2 | T | C,T | C,T | C,T | C,T | A | T | A | A | T | A | C |

FIG. 13 PH890 conversion data

| Entry Name | SI_ID | corr_yearm_ld | stddev | # of Reps | 1 PHM 8211 -16 | 1 PHM 3951 -25 | 6 PHM 9362 -8 | 6 PHM 1147 -19 | 6 PHM 11850 -6 | 6 PHM 5280 -41 | 6 PHM 9301 -37 | 5 PHM 9009 -13 | 5 PHM 3171 -5 | 5 PHM 3860 -43 | 7 PHM 7942 -12 | 7 PHM 678 -22 | 7 PHM 8358 -17 | 8 PHM 16415 -8 | 8 PHM 737 -215 |
|---|---|---|---|---|---|---|---|---|---|---|---|---|---|---|---|---|---|---|---|
| PH861 | | | | | T | T | G | T | C | G | T | C | G | G | C | C | G | T | T |
| PH890 | 7230834 | 3.5 | 1.0 | 6 | G | C | A | C | T | A | C | T | NF | A | C | NF | C | C | C |
| PH890FR2 | 11062294 | 5.0 | 0.8 | 4 | T | C,T | G | T | C | G | T | T | A | A | C | C | C | C | C |
| PH890FR2 | 11062297 | 4.0 | | 1 | G | C | A,G | C,T | C,T | EQV | C,T | T | A | A | C | C | C | C | C |
| PH890FR2 | 11066544 | 4.4 | 1.1 | 5 | EQV | C,T | A | C | T | A | C | T | A | A | C | C | C | C | C |
| PH890FR2 | 11066565 | 5.0 | 2.8 | 2 | T | T | A,G | EQV | EQV | A,G | C,T | T | A | A | C | C | C | C | C |
| PH890FR2 | 11066600 | 4.5 | 0.7 | 2 | T | T | G | T | C | G | EQV | T | A | A | C | C | C | C | C |
| PH890FR2 | 11066601 | 4.0 | 1.0 | 3 | T | T | A,G | C,T | C,T | A | C,T | T | A | A | C | C | C | C | C |
| PH890FR4 | 11066639 | 4.0 | . | 1 | G | C | G | T | C | G | T | T | A | A | C | C | C | C | C |
| PH890FR4 | 11066659 | 3.0 | 0.0 | 2 | G | C | G | T | C | G | T | T | A | A | C | C | C | C | C |
| PH890FR4 | 11066672 | 3.7 | 1.5 | 3 | T | C,T | NF | NF | NF | NF | NF | T | A | A | C | C | C | C | C |
| PH890FR4 | 11066680 | 4.0 | . | 1 | T | T | A,G | EQV | EQV | A,G | C,T | T | A | A | C | C | C | C | C |
| PH890FR4 | 11066707 | 2.5 | 0.7 | 2 | T | T | A,G | T | C | G | T | T | A | A | C | C | C | C | C |

FIG. 14 PHB1V conversion data

| Entry Name | SI_ID | corr_year mid | stddev | # of Reps | 1 PHM 8711 -17 | 1 PHM 8211 -16 | 1 PHM 1754 -20 | 1 PHM 3951 -25 | 6 PHM 9362 -8 | 6 PHM 1147 -16 | 6 PHM 1147 -19 | 5 PHM 9009 -13 | 7 PHM 7942 -12 | 7 PHM 678 -22 | 8 PHM 9092 -11 |
|---|---|---|---|---|---|---|---|---|---|---|---|---|---|---|---|
| PHG61 | 4788824 | | | | C | T | C | T | G | G | T | C | C | C | T |
| PHB1V | 11066895 | 4.2 | 0.4 | 6 | T | G | T | C | A | A | C | T | T | A | C |
| PHB1VFR1 | 11066896 | 4.0 | 0.7 | 5 | C | T | C | T | A | A | C | NF | T | A | NF |
| PHB1VFR1 | 11066911 | 4.4 | 0.5 | 5 | T | G | T | C | A | A | C | T | T | A | C |
| PHB1VFR1 | 11066923 | 4.0 | . | 1 | T | G | T | C | A | A | C | T | T | A | C |
| PHB1VFR1 | 11066930 | 5.3 | 0.6 | 3 | C | T | C | T | A | A | C | T | T | A | C |
| PHB1VFR1 | 11066981 | 5.0 | . | 1 | C | T | C | T | A,G | A | C | T | T | A | C |
| PHB1VFR3 | 11066988 | 7.0 | 1.4 | 2 | C | T | C,T | C,T | G | A | C | T | T | A | C |
| PHB1VFR3 | 11067002 | 6.0 | 1.0 | 3 | T | EQV | T | C,T | G | A | C | T | T | NF | C |
| PHB1VFR3 | 11067017 | 8.0 | . | 1 | C | T | C | T | A,G | A | C | T | T | A | C |
| PHB1VFR3 | 11067023 | 6.6 | 1.1 | 5 | C | T | C | T | A | A | C | T | T | A | C |
| PHB1VFR3 | 11067023 | 6.8 | 0.5 | 4 | C | T | C | T | A | A | C | T | T | A | C |

FIG. 15A Hybrid data

| ID | Cross PHG61 | Mean visual ear mold | SE mean | Chromosome 1 | | | Chromosome 6 | | | | |
|---|---|---|---|---|---|---|---|---|---|---|---|
| | | | | PHM 6929 -3 | PHM 8211 -16 | PHM 14506 -7 | PHM 4423 -4 | PHM 9362 -8 | PHM 1147 -19 | PHM 11850 -6 | |
| 12022399 | PHFCJ/PH1JC | 2.8 | 0.4 | C | T | C | T | G | T | C | |
| 12022400 | PHFCJFR3/PH1JC | 4.2 | 0.4 | T | G,T | C | C | A,G | T | C,T | |
| 12022401 | PHFCJFR3/PH1JC | 3.2 | 0.4 | C,T | G,T | C | C,T | A | C,T | C,T | |
| 12022402 | PHFCJFR3/PH1JC | 3.8 | 0.4 | T | G,T | C | C,T | A,G | C,T | C,T | |
| 12022383 | PHFCJFR4/PH1JC | 2.8 | 0.4 | | G,T | C,T | C,T | A,G | T | C | |
| 12022384 | PHFCJFR4/PH1JC | 3.3 | 0.4 | C,T | G,T | C,T | C,T | A | C,T | C,T | |
| 12022385 | PHFCJFR4/PH1JC | 3.5 | 0.4 | EQV | G,T | C,T | C,T | A,G | T | C | |
| 12022392 | PH3RC/PH70R | 5.5 | 0.4 | T | G | C | C | A | C | C,T | |
| 12022393 | PH3RC/PH70RFR2 | 5.5 | 0.4 | T | G,T | C,T | NF | NF | NF | NF | |
| 12022394 | PH3RC/PH70RFR2 | 6.2 | 0.4 | T | G,T | C,T | C | A | C | C,T | |
| 12022395 | PH3RC/PH70RFR2 | 7.2 | 0.4 | T | NF | C,T | C,T | A,G | C,T | C,T | |
| 12022396 | PH3RC/PH70RFR3 | 5.0 | 0.4 | C,T | G,T | C,T | C,T | A,G | C,T | C,T | |
| 12022397 | PH3RC/PH70RFR3 | 7.2 | 0.4 | C,T | G,T | C,T | C,T | A,G | C,T | C,T | |
| 12022398 | PH3RC/PH70RFR3 | 5.5 | 0.4 | C,T | G,T | C,T | C,T | A,G | C,T | C,T | |
| 12022386 | PH89O/PH4CN | 3.8 | 0.4 | C,T | G | C,T | C | A | C | T | |
| 12022387 | PH89OFR2/PH4CN | 5.8 | 0.4 | C | G,T | T | C,T | A,G | C,T | C,T | |
| 12022388 | PH89OFR2/PH4CN | 4.7 | 0.4 | C | G,T | T | C,T | A,G | C,T | C,T | |
| 12022389 | PH89OFR2/PH4CN | 5.5 | 0.4 | C | G,T | T | C,T | A,G | C,T | C,T | |
| 12022390 | PH89OFR4/PH4CN | 4.8 | 0.4 | C | G,T | T | C,T | A,G | C,T | C,T | |
| 12022391 | PH89OFR4/PH4CN | 3.8 | 0.4 | C,T | G | C,T | C,T | A,G | C,T | C,T | |

 PHG61 allele

FIG. 15B Hybrid data (cont.)

| ID | Cross PHG61 | Mean visual ear mold | SE mean | Chromosome 1 PHM 6929 -3 | PHM 8211 -16 | PHM 14506 -7 | Chromosome 6 PHM 4423 -4 | PHM 9362 -8 | PHM 1147 -19 | PHM 11850 -6 |
|---|---|---|---|---|---|---|---|---|---|---|
| X4P380 | PHEKJ/PH51H | 2.0 | 0.3 | C | T | T | T | G | T | C |
| TQI4991831 | PHEKJ/PH51HFR2 | 6.0 | 0.6 | T | G | C | C | A | C | T |
| TQI4991831 | PHEKJ/PH51HFR2 | 3.3 | 0.3 | C,T | G,T | C,T | C,T | A,G | C | T |
| TQI4991831 | PHEKJ/PH51HFR2 | 3.3 | 0.3 | T | G | C | C,T | EQV | C | T |
| TQI4991831 | PHEKJ/PH51HFR2 | 5.0 | 0.3 | C,T | G,T | C,T | C,T | A,G | C | T |
| TIX4R620 | PHF1J/PH51H | 7.3 | 0.3 | C,T | G | C,T | C | A | C,T | T |
| TQI4991832 | PHF1J/PH51HFR2 | 7.3 | 0.3 | C | EQV | T | C,T | A | C,T | T |
| TQI4991832 | PHF1J/PH51HFR2 | 7.0 | 0.3 | C,T | G,T | C,T | C,T | A | C,T | T |
| TQI4991832 | PHF1J/PH51HFR2 | 7.3 | 0.3 | C | G,T | T | C,T | A,G | C,T | T |
| YS10959434 | PH1W2/PH51H | 5.3 | 0.3 | T | G | C | C | A | C | T |
| TQI4991833 | PH1W2/PH51HFR2 | 6.5 | 0.4 | C,T | G,T | C,T | C,T | A,G | C | T |
| TQI4991833 | PH1W2/PH51HFR2 | 6 | 0.3 | C,T | G,T | C,T | C,T | A,G | C | T |
| TQI4991833 | PH1W2/PH51HFR2 | 5.7 | 0.3 | C,T | G,T | C,T | C,T | A,G | C | T |

PHG61 allele

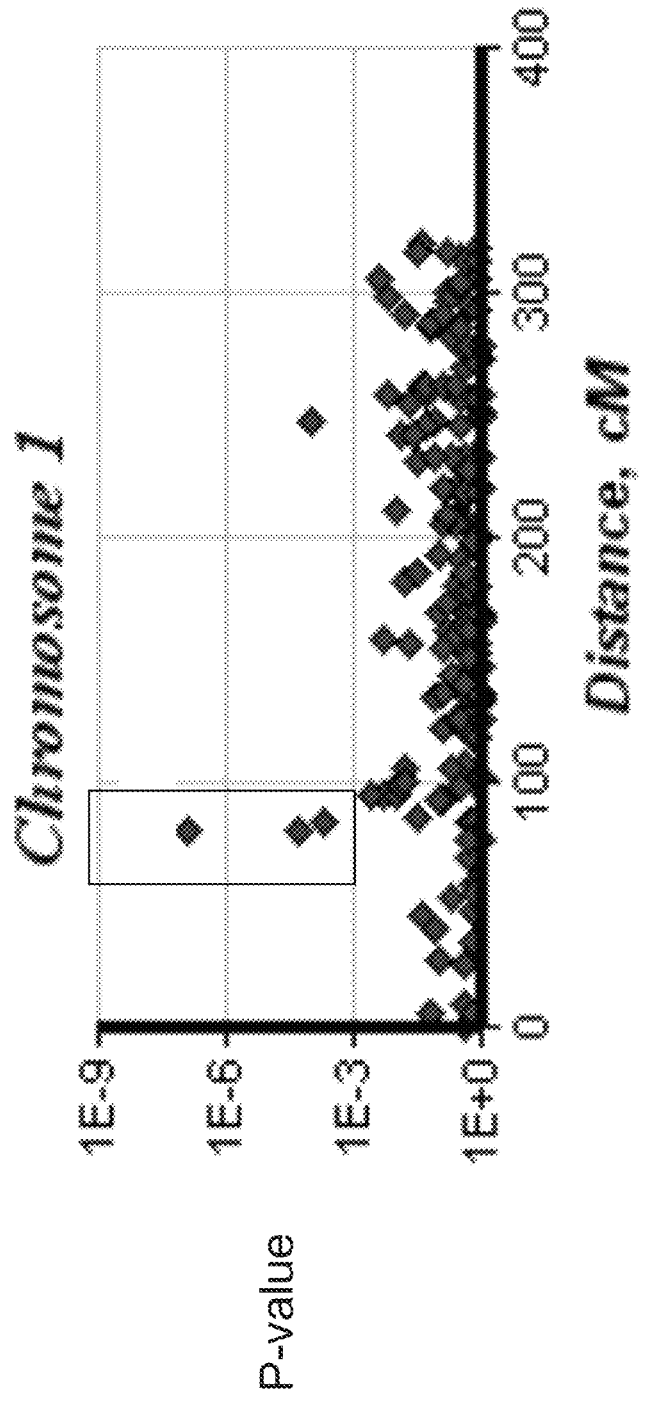
FIG. 16: Associations between marker loci on chromosome 1 and *Fusarium* ear mold resistance in a non-stiff stalk subpopulation
Boxed region indicates marker loci that are significantly associated with *Fusarium* ear mold resistance at $p \leq 0.001$.

GENETIC LOCI ASSOCIATED WITH FUSARIUM EAR MOLD RESISTANCE IN MAIZE

CROSS-REFERENCE TO RELATED APPLICATION

This application is a Divisional of U.S. application Ser. No. 12/759,178, filed Apr. 13, 2010, which claims the benefit of U.S. Provisional Application No. 61/168,779, filed Apr. 13, 2009, which is incorporated by reference in its entirety.

FIELD OF THE INVENTION

The present disclosure relates to compositions and methods useful in enhancing resistance to *Fusarium* ear mold in maize plants.

BACKGROUND OF THE INVENTION

*Fusarium* ear mold (also referred to as *Fusarium* ear rot) is a devastating disease of maize caused by species of the *Gibberella fuijkuroi* complex, namely *F. verticillioides*, *F. proliferatum*, and/or *F. subglutinans*. It is predominantly found in the southeastern United States, southern Europe, Mexico, Brazil, Argentina, and South Africa, and affects both grain yield and quality. *Fusarium* ear mold also results in contamination by several mycotoxins, including fumonisins (FUM), moniliformin (MON), and/or beauvericin, which appear to cause a number of human and animal diseases. Fumonisins, e.g., are linked to several animal toxicoses including leukoencephalomalacia (Marasas et al. (1988) Onderstepoort J. Vet. Res. 55:197-204; Wilson et al. (1990) American Association of Veterinary Laboratory Diagnosticians: Abstracts 33rd Annual Meeting, Denver, Colo., Madison, Wis., USA) and porcine pulmonary edema (Colvin et al. (1992) Mycopathologia 117:79-82). Fumonisins are also suspected carcinogens (Geary et al. (1971) Coord. Chem. Rev. 7:81; Gelderblom et al. (1991) Carcinogenesis 12:1247-1251; Gelderblom et al. (1992) Carcinogenesis 13:433-437) and have been linked to birth defects in humans (Missmer et al. (2006) Environ Health perspect 114:237-41).

The etiology of *Fusarium* ear mold is poorly understood, although physical damage to the ear and certain environmental conditions can contribute to its occurrence (Nelson et al. (1992) Mycopathologia 117:29-36). When conditions for fungal growth are optimum, there are no cultural practices sufficient to minimize mycotoxin levels to a level deemed as "safe" by the Food and Drug Administration. Genetic resistance to *Fusarium* ear mold has been identified (Gendloff et al. (1986) Phytopathology 76:684-688; Holley et al. (1989) Plant Dis. 73:578-580), and several breeding efforts have led to the identification of maize germplasm with heritable resistance to *Fusarium* ear mold. However, incorporation of this resistance in maize inbred lines has been difficult. The use of phenotypic selection to introgress resistance is time consuming and difficult, and since *Fusarium* ear mold is sensitive to environmental conditions, selection for resistance from year to year based solely on phenotype has proven unreliable. In addition, specialized disease screening sites can be costly to operate, and plants must be grown to maturity in order to classify the level of resistance or susceptibility.

Selection through the use of molecular markers associated with *Fusarium* ear mold resistance has the advantage of permitting at least some selection based solely on the genetic composition of the progeny. Moreover, resistance to *Fusarium* ear mold can be determined very early on in the plant life cycle, even as early as the seed stage. The increased rate of selection that can be obtained through the use of molecular markers associated with the *Fusarium* ear mold resistance trait means that plant breeding for *Fusarium* ear mold resistance can occur more rapidly, thereby generating commercially acceptable resistant plants in a relatively short amount of time. Thus, it is desirable to provide compositions and methods for identifying and selecting maize plants with enhanced resistance to *Fusarium* ear mold. These plants can be used in breeding programs to generate high-yielding hybrids with resistance to *Fusarium* ear mold.

SUMMARY

Compositions and methods for identifying and selecting maize plants with enhanced resistance to *Fusarium* ear mold are provided.

In one embodiment, methods of selecting a maize plant with enhanced resistance to *Fusarium* ear mold are provided. In these methods, DNA is obtained, and the presence of at least one marker allele is detected. The marker allele can include any marker allele that is linked to and associated with any of the following marker alleles: a "T" at PHM8211-16, a "C" at PHM8711-14, a "T" at PHM14506-7, a "C" at PHM1934-37, a "C" at PHM8711-17, a "C" at PHM1754-20, a "T" at PHM3951-25, a "C" at PHM6929-3, an "A" at PHM10054-14, an "A" at PHM10721-9, an "A" at PHM10721-16, a "G" at PHM15661-21, a "G" at PHM9362-8, a "G" at PHM1147-16, a "T" at PHM11850-3, a "C" at PHM11850-6, an "A" at PHM13773-6, a "C" at PHM13773-11, an "A" at PHM16422-11, a "T" at PHM1147-19, a "G" at PHM5280-41, a "T" at PHM9301-37, and a "T" at PHM4423-4. A maize plant that has the marker allele linked to and associated with any of the marker alleles listed above is then selected as having enhanced *Fusarium* ear mold resistance.

In other embodiments, the marker allele can be linked to any of the following marker alleles: a "T" at PHM8211-16, a "C" at PHM8711-14, a "T" at PHM14506-7, a "C" at PHM1934-37, a "C" at PHM8711-17, a "C" at PHM1754-20, a "T" at PHM3951-25, a "C" at PHM6929-3, an "A" at PHM10054-14, an "A" at PHM10721-9, an "A" at PHM10721-16, a "G" at PHM15661-21, a "G" at PHM9362-8, a "G" at PHM1147-16, a "T" at PHM11850-3, a "C" at PHM11850-6, an "A" at PHM13773-6, a "C" at PHM13773-11, an "A" at PHM16422-11, a "T" at PHM1147-19, a "G" at PHM5280-41, a "T" at PHM9301-37, and a "T" at PHM4423-4 by 30 cM, 25, 20, 15, 10, 9, 8, 7, 6, 5, 4, 3, 2, 1, 0.9, 0.8, 0.7, 0.6, 0.5, 0.4, 0.3, 0.2, or 0.1 cM, or it can be any of the following marker alleles: a "T" at PHM8211-16, a "C" at PHM8711-14, a "T" at PHM14506-7, a "C" at PHM1934-37, a "C" at PHM8711-17, a "C" at PHM1754-20, a "T" at PHM3951-25, a "C" at PHM6929-3, an "A" at PHM10054-14, an "A" at PHM10721-9, an "A" at PHM10721-16, a "G" at PHM15661-21, a "G" at PHM9362-8, a "G" at PHM1147-16, a "T" at PHM11850-3, a "C" at PHM11850-6, an "A" at PHM13773-6, a "C" at PHM13773-11, an "A" at PHM16422-11, a "T" at PHM1147-19, a "G" at PHM5280-41, a "T" at PHM9301-37, and a "T" at PHM4423-4.

In one embodiment, methods for identifying maize plants with enhanced resistance to *Fusarium* ear mold by detecting a marker locus in the genome of the maize plant using the sequence of the marker locus, a portion of the sequence of the marker locus, or a complement of the sequence of the marker locus, or of a portion thereof, as a marker probe, are provided. The marker probe hybridizes under stringent conditions to the contiguous DNA between and including SEQ ID NO:41, or a nucleotide sequence that is 95% identical to SEQ ID NO:41 based on the Clustal V method of alignment, and SEQ ID NO:47, or a nucleotide sequence that is 95% identical to SEQ ID NO:47 based on the Clustal V method of alignment, and the marker locus comprises at least one allele that is associated with the enhanced resistance to *Fusarium* ear mold. Maize plants identified by this method are also of interest.

In another embodiment, methods for identifying maize plants with enhanced resistance to *Fusarium* ear mold by detecting at least one marker allele associated with the enhanced resistance in the germplasm of a maize plant are provided. The marker locus can be selected from any of the following marker loci: the PHM and SSR markers PHM6929, bnlg1007, PHM8711, bnlg1083, PHM8211, PHM14506, PHM1754, PHM3951, PHM1934, PHM10054, PHM10721, and PHM15661; and the SNP markers PHM8211-16-I, PHM8711-14-U, PHM14506-7-U, PHM1934-37-U, PHM8711-17-U, PHM1754-20-U, PHM3951-25-U, PHM6929-3-U, PHM10054-14-U, PHM10721-9-U, PHM10721-16-U, and PHM15661-21-U; as well as any other marker that is linked to these markers. The marker locus can also be found within the interval on chromosome 1 comprising and flanked by:
  i. PHM6929 and PHM1934, or
  ii. PHM6929 and PHM14506.

The marker locus comprises at least one allele that is associated with enhanced resistance to *Fusarium* ear mold. Maize plants identified by this method are also of interest.

In another embodiment, methods for identifying maize plants with enhanced resistance to *Fusarium* ear mold by detecting a haplotype in the germplasm of the maize plant that is associated with enhanced resistance to *Fusarium* ear mold are provided. The haplotype comprises alleles at one or more marker loci, wherein the one or more marker loci are found within the interval on chromosome 1 comprising and flanked by:
  i. PHM6929 and PHM1934, or
  ii. PHM6929 and PHM14506.

The haplotype can comprise at least one of the following alleles: a "T" at PHM8211-16, a "C" at PHM8711-14, a "T" at PHM14506-7, a "C" at PHM1934-37, a "C" at PHM8711-17, a "C" at PHM1754-20, a "T" at PHM3951-25, a "C" at PHM6929-3, an "A" at PHM10054-14, an "A" at PHM10721-9, an "A" at PHM10721-16, and a "G" at PHM15661-21. The haplotype may also constitute:
  i. a "C" at PHM6929-3, a "T" at PHM8211-16, and a "T" at PHM14506-7;
  ii. an "A" at PHM10054-14 and an "A" at PHM10721-9; and
  iii. an "A" at PHM10054-14, a "T" at PHM8211-16, and an "A" at PHM10721-9. Maize plants identified by this method are also of interest.

In another embodiment, methods of selecting plants with enhanced resistance to *Fusarium* ear mold are provided. In one aspect, a first maize plant is obtained that has at least one allele of a marker locus wherein the allele is associated with the enhanced resistance. The marker locus can be found within the interval on chromosome 1 comprising and flanked by:
  i. PHM6929 and PHM1934, or
  ii. PHM6929 and PHM14506.

The first maize plant can then be crossed to a second maize plant, and the progeny plants resulting from the cross can be evaluated for the allele of the first maize plant. Progeny plants that possess the allele of the first maize plant can be selected as having enhanced resistance to *Fusarium* ear mold. Progeny plants selected by this method are also of interest.

In another embodiment, methods of selecting maize plants with enhanced resistance to *Fusarium* ear mold are provided. In one aspect, a first maize plant is obtained that has a "C" at PHM6929-3, a "T" at PHM8211-16, and a "T" at PHM14506-7; an "A" at PHM10054-14 and an "A" at PHM10721-9; or an "A" at PHM10054-14, a "T" at PHM8211-16, and an "A" at PHM10721-9. The first maize plant can be crossed to a second maize plant, and the progeny plants resulting from the cross can be evaluated for said alleles. Progeny plants that possess said alleles can be selected as having enhanced resistance to *Fusarium* ear mold. Progeny plants selected by this method are also of interest.

In another embodiment, methods for identifying maize plants with enhanced resistance to *Fusarium* ear mold by detecting a marker locus in the genome of the maize plant using the sequence of the marker locus, a portion of the sequence of the marker locus, or a complement of the sequence of the marker locus, or of a portion thereof, as a marker probe, are provided. The marker probe hybridizes under stringent conditions to the contiguous DNA between and including SEQ ID NO:48, or a nucleotide sequence that is 95% identical to SEQ ID NO:48 based on the Clustal V method of alignment, and SEQ ID NO:55, or a nucleotide sequence that is 95% identical to SEQ ID NO:55 based on the Clustal V method of alignment, and the marker locus comprises at least one allele that is associated with enhanced resistance to *Fusarium* ear mold. Maize plants identified by this method are also of interest.

In another embodiment, methods for identifying maize plants with enhanced resistance to *Fusarium* ear mold by detecting at least one marker allele associated with the enhanced resistance in the germplasm of a maize plant are provided. The marker locus can be selected from any of the following marker loci: the PHM and SSR markers PHM4423, bnlg1732, PHM9362, PHI445613, PHM1147, PHM11850, PHM9301, umc1762, PHM5280, PHM13773, and PHM16422; and the SNP markers PHM9362-8-U, PHM1147-16-U, PHM11850-3-U, PHM11850-6-U, PHM13773-6-U, PHM13773-11-U, PHM16422-11-U, PHM1147-19-U, PHM5280-41-U, PHM9301-37-U, and PHM4423-4-U, as well as any other marker that is linked to these markers. The marker locus can be found within the interval on chromosome 6 comprising and flanked by PHM4423 and PHM16422. The marker locus comprises at least one allele that is associated with enhanced resistance to *Fusarium* ear mold. Maize plants identified by this method are also of interest.

In another embodiment, methods for identifying maize plants with enhanced resistance to *Fusarium* ear mold by detecting a haplotype in the germplasm of the maize plant are provided. The haplotype comprises alleles at one or more marker loci, wherein the one or more marker loci are found within the interval on chromosome 6 comprising and flanked by PHM4423 and PHM16422. The haplotype is associated with enhanced resistance to *Fusarium* ear mold and can comprise at least one of the following alleles: a "G" at PHM9362-8, a "G" at PHM1147-16, a "T" at PHM11850-3, a "C" at PHM11850-6, an "A" at PHM13773-6, a "C" at PHM13773-11, an "A" at PHM16422-11, a "T" at PHM1147-19, a "G" at PHM5280-41, a "T" at PHM9301-37, and a "T" at PHM4423-4. The haplotype may also constitute:

i. a "T" at PHM4423-4, a "T" at PHM11850-3, and an "A" at PHM13773-6; or ii. a "G" at PHM9362-8 and an "A" at PHM13773-6.

Maize plants identified by this method are also of interest.

In another embodiment, methods of selecting maize plants with enhanced resistance to *Fusarium* ear mold are provided. In one aspect, a first maize plant is obtained that has at least one allele of a marker locus wherein the allele is associated with the enhanced resistance. The marker locus can be found within the chromosomal interval comprising and flanked by PHM4423 and PHM16422. The first maize plant can be crossed to a second maize plant, and the progeny plants resulting from the cross can be evaluated for the allele of the first maize plant. Progeny plants that possess the alleles from the first maize plant can be selected as having enhanced resistance to *Fusarium* ear mold. Progeny plants selected by this method are also of interest.

In another embodiment, methods of selecting maize plants with enhanced resistance to *Fusarium* ear mold are provided. In one aspect, a first maize plant is obtained that has a "T" at PHM4423-4, a "T" at PHM11850-3, and an "A" at PHM13773-6 or a "G" at PHM9362-8 and an "A" at PHM13773-6. The first maize plant can be crossed to a second maize plant, and the progeny plants resulting from the cross can be evaluated at said alleles. Progeny plants that possess said alleles can be selected as having enhanced resistance to *Fusarium* ear mold. Progeny plants selected by this method are also of interest.

In another embodiment, methods for identifying maize plants with enhanced resistance to *Fusarium* ear mold by detecting alleles at two separate marker loci, referred to herein as marker locus 1 and marker locus 2, in the germplasm of the maize plant are provided. Marker locus 1 is located within an interval on chromosome 1 comprising and flanked by:

i. PHM6929 and PHM1934, or ii. PHM6929 and PHM14506; and marker locus 2 is located within an interval on chromosome 6 comprising and flanked by PHM4423 and PHM16422. Each marker locus comprises at least one allele that is associated with enhanced resistance to *Fusarium* ear mold. Maize plants identified by this method are also of interest.

In another embodiment, methods for identifying maize plants with enhanced resistance to *Fusarium* ear mold by detecting in the germplasm of the maize plant haplotype 1 and haplotype 2 are provided. Both haplotype 1 and haplotype 2 comprise alleles at one or more marker loci. For haplotype 1, the marker loci are located within an interval on chromosome 1 comprising and flanked by:

i. PHM6929 and PHM1934, or ii. PHM6929 and PHM14506; and for haplotype 2, the marker loci are located within an interval on chromosome 6 comprising and flanked by PHM4423 and PHM16422. Both haplotypes are associated with enhanced resistance to *Fusarium* ear mold. Haplotype 1 can comprise:

i. a "C" at PHM6929-3, a "T" at PHM8211-16, and a "T" at PHM14506-7, ii. an "A" at PHM10054-14 and an "A" at PHM10721-9; or iii. an "A" at PHM10054-14, a "T" at PHM8211-16, and an "A" at PHM 10721-9;

and haplotype 2 can comprise:

i. a "T" at PHM4423-4, a "T" at PHM11850-3, and an "A" at PHM13773-6; or ii. a "G" at PHM9362-8 and an "A" at PHM13773-6.

Maize plants identified by this method are also of interest.

In another embodiment, methods of selecting maize plants with enhanced resistance to *Fusarium* ear mold are provided. In one aspect, a first maize plant is obtained that has at least one allele of a first marker locus and at least one allele of second marker locus. The first marker locus is located within an interval on chromosome 1 comprising and flanked by:

i. PHM6929 and PHM1934, or ii. PHM6929 and PHM14506, and the second marker locus is located within an interval on chromosome 6 comprising and flanked by PHM4423 and PHM16422. The at least one allele of the first marker locus and the at least one allele of the second marker locus are associated with enhanced resistance to *Fusarium* ear mold. The first maize plant can be crossed to a second maize plant, and the progeny plants resulting from the cross can be evaluated for the alleles of the first maize plant. Progeny plants that possess the alleles of the first maize plant can be selected as having enhanced resistance to *Fusarium* ear mold. Progeny plants selected by this method are also of interest.

In another embodiment, methods of selecting maize plants with enhanced resistance to *Fusarium* ear mold are provided. In one aspect, a first maize plant is obtained that has a haplotype at the chromosome 1 QTL that is associated with enhanced resistance to *Fusarium* ear mold and a haplotype at the chromosome 6 QTL that is associated with enhanced resistance to *Fusarium* ear mold. The first maize plant can be crossed to a second maize plant, and the progeny plants resulting from the cross can be evaluated for said alleles. Progeny plants that possess said alleles can be selected as having enhanced resistance to *Fusarium* ear mold. Progeny plants selected by this method are also of interest.

BRIEF DESCRIPTION OF FIGURES AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIGS. 1A, 1B, and 1C show the physical map arrangement of sequenced BACs (obtained from the Maize Genome Browser, which is publicly available on the internet; at maizesequence.org) on chromosome 1 that assemble to the region defined by and including PHM6929 (SEQ ID NO:41) and PHM1934 (SEQ ID NO:47). The positions of the PHM and SSR markers described herein are indicated; the SEQ ID NOs of the PHM reference sequences are indicated in the figures.

FIGS. 2A and 2B show the physical map arrangement of sequenced BACs (obtained from the Maize Genome Browser, which is publicly available on the internet; at maizesequence.org) on chromosome 6 that assemble to the region defined by and including PHM4423 (SEQ ID NO:48) and PHM16422 (SEQ ID NO:55). The positions of the PHM and SSR markers described herein are indicated; the SEQ ID NOs of the PHM reference sequences are indicated in the figures.

FIG. 3 shows a comparison between PHG61, the highly resistant line, and 1047, a susceptible line.

FIG. 4 shows the FUSERS scale used as a guide to score *Fusarium* ear mold infection.

FIGS. 5A and 5B show the SEQ ID NOs for the oligos and probes designed for use with Invader Plus® reactions in the haplotyping of individual plants in the genomic intervals containing *Fusarium* ear mold QTL1.

FIGS. 6A and 6B show the SEQ ID NOs for the oligos and probes designed for use with Invader Plus® reactions in the haplotyping of individual plants in the genomic interval containing *Fusarium* ear mold QTL6.

FIGS. 7A, 7B, and 7C show the SEQ ID NOs for the oligos and probes designed for use with Invader Plus® reactions in the haplotyping of individual plants in the genomic interval containing *Fusarium* ear mold QTL5, QTL7, and QTL8, respectively.

FIG. 8 shows the PHCA5 conversion data.
FIG. 9 shows the PH51H conversion data.
FIG. 10 shows the PH70R conversion data.
FIG. 11 shows the PH87H conversion data.
FIG. 12 shows the PHFCJ conversion data.
FIG. 13 shows the PH890 conversion data.
FIG. 14 shows the PHB1V conversion data.
FIGS. 15A and 15B show the phenotypic results of using a converted line as a parent in a hybrid cross versus using a non-converted line.

FIG. 16 shows associations between marker loci on chromosome 1 and *Fusarium* ear mold resistance in a non stiff stalk subpopulation.

SEQ ID NO:1 and SEQ ID NO:2 are the primers for AFLP marker 177.
SEQ ID NO:3 and SEQ ID NO:4 are the primers for AFLP marker T292.
SEQ ID NO:5 and SEQ ID NO:6 are the primers for AFLP marker D166.
SEQ ID NO:7 and SEQ ID NO:8 are the primers for AFLP marker C116.
SEQ ID NO:9 and SEQ ID NO:10 are the primers for SSR marker bnlg1953.
SEQ ID NO:11 and SEQ ID NO:12 are the primers for SSR marker LGI112958.
SEQ ID NO:13 and SEQ ID NO:14 are the primers for SSR marker PHI445613.
SEQ ID NO:15 and SEQ ID NO:16 are the primers for SSR marker PHI364545.
SEQ ID NO:17 and SEQ ID NO:18 are the primers for SSR marker bnlg1732.
SEQ ID NO:19 and SEQ ID NO:20 are the primers for SSR marker umc1762.
SEQ ID NO:21 and SEQ ID NO:22 are the primers for SSR marker bnlg1007.
SEQ ID NO:23 and SEQ ID NO:24 are the primers for SSR bnlg1083.
SEQ ID NO:25 and SEQ ID NO:26 are the primers for SSR marker PH1256546.
SEQ ID NO:27 and SEQ ID NO:28 are the primers for SSR bnlg1174.
SEQ ID NO:29 and SEQ ID NO:30 are the primers for SSR umc1805.
SEQ ID NO:31 and SEQ ID NO:32 are the primers for SSR umc1462.
SEQ ID NO:33 is the sequence of the PHM8211 forward external primer.
SEQ ID NO:34 is the sequence of the PHM8211 forward internal primer.
SEQ ID NO:35 is the sequence of the PHM8211 reverse internal primer.
SEQ ID NO:36 is the sequence of the PHM8211 reverse external primer.
SEQ ID NO:37 is the sequence of the PHM1934 forward external primer.
SEQ ID NO:38 is the sequence of the PHM1934 forward internal primer.
SEQ ID NO:39 is the sequence of the PHM1934 reverse internal primer.
SEQ ID NO:40 is the sequence of the PHM1934 reverse external primer.
SEQ ID NO:41 is the reference sequence for PHM6929.
SEQ ID NO:42 is the reference sequence for PHM8711.
SEQ ID NO:43 is the reference sequence for PHM8211.
SEQ ID NO:44 is the reference sequence for PHM14506.
SEQ ID NO:45 is the reference sequence for PHM1754.
SEQ ID NO:46 is the reference sequence for PHM3951.
SEQ ID NO:47 is the reference sequence for PHM1934.
SEQ ID NO:48 is the reference sequence for PHM4423.
SEQ ID NO:49 is the reference sequence for PHM9362.
SEQ ID NO:50 is the reference sequence for PHM1147.
SEQ ID NO:51 is the reference sequence for PHM11850.
SEQ ID NO:52 is the reference sequence for PHM9301.
SEQ ID NO:53 is the reference sequence for PHM5280.
SEQ ID NO:54 is the reference sequence for PHM13773.
SEQ ID NO:55 is the reference sequence for PHM16422.
SEQ ID NO:56 is the reference sequence for PHM9009.
SEQ ID NO:57 is the reference sequence for PHM3171.
SEQ ID NO:58 is the reference sequence for PHM3860.
SEQ ID NO:59 is the reference sequence for PHM7942.
SEQ ID NO:60 is the reference sequence for PHM678.
SEQ ID NO:61 is the reference sequence for PHM8358.
SEQ ID NO:62 is the reference sequence for PHM16415.
SEQ ID NO:63 is the reference sequence for PHM737.
SEQ ID NO:64 is the reference sequence for PHM9092.
SEQ ID NO:65 is the sequence of the PHM6929-3-U forward primer.
SEQ ID NO:66 is the sequence of the PHM6929-3-U reverse primer.
SEQ ID NO:67 is the sequence of PHM6929-3-U probe 1.
SEQ ID NO:68 is the sequence of PHM6929-3-U probe 2.
SEQ ID NO:69 is the sequence of the PHM8711-14-U forward primer.
SEQ ID NO:70 is the sequence of the PHM8711-14-U reverse primer.
SEQ ID NO:71 is the sequence of PHM8711-14-U probe 1.
SEQ ID NO:72 is the sequence of PHM8711-14-U probe 2.
SEQ ID NO:73 is the sequence of the PHM8211-16-I forward primer.
SEQ ID NO:74 is the sequence of the PHM8211-16-I reverse primer.
SEQ ID NO:75 is the sequence of PHM8211-16-I probe 1.
SEQ ID NO:76 is the sequence of PHM8211-16-I probe 2.
SEQ ID NO:77 is the sequence of the PHM14506-7-U forward primer.

SEQ ID NO:78 is the sequence of the PHM14506-7-U reverse primer.

SEQ ID NO:79 is the sequence of PHM14506-7-U probe 1.

SEQ ID NO:80 is the sequence of PHM14506-7-U probe 2.

SEQ ID NO:81 is the sequence of the PHM1754-20-U forward primer.

SEQ ID NO:82 is the sequence of the PHM1754-20-U reverse primer.

SEQ ID NO:83 is the sequence of PHM1754-20-U probe 1.

SEQ ID NO:84 is the sequence of PHM1754-20-U probe 2.

SEQ ID NO:85 is the sequence of the PHM3951-25-U forward primer.

SEQ ID NO:86 is the sequence of the PHM3951-25-U reverse primer.

SEQ ID NO:87 is the sequence of PHM3951-25-U probe 1.

SEQ ID NO:88 is the sequence of PHM3951-25-U probe 2.

SEQ ID NO:89 is the sequence of the PHM1934-37-U forward primer.

SEQ ID NO:90 is the sequence of the PHM1934-37-U reverse primer.

SEQ ID NO:91 is the sequence of PHM1934-37-U probe 1.

SEQ ID NO:92 is the sequence of PHM1934-37-U probe 2.

SEQ ID NO:93 is the sequence of the PHM4423-4-U forward primer.

SEQ ID NO:94 is the sequence of the PHM4423-4-U reverse primer.

SEQ ID NO:95 is the sequence of PHM4423-4-U probe 1.

SEQ ID NO:96 is the sequence of PHM4423-4-U probe 2.

SEQ ID NO:97 is the sequence of the PHM9362-8-U forward primer.

SEQ ID NO:98 is the sequence of the PHM9362-8-U reverse primer.

SEQ ID NO:99 is the sequence of PHM9362-8-U probe 1.

SEQ ID NO:100 is the sequence of PHM9362-8-U probe 2.

SEQ ID NO:101 is the sequence of the PHM1147-16-U forward primer.

SEQ ID NO:102 is the sequence of the PHM1147-16-U reverse primer.

SEQ ID NO:103 is the sequence of PHM1147-16-U probe 1.

SEQ ID NO:104 is the sequence of PHM1147-16-U probe 2.

SEQ ID NO:105 is the sequence of the PHM1147-19-U forward primer.

SEQ ID NO:106 is the sequence of the PHM1147-19-U reverse primer.

SEQ ID NO:107 is the sequence of PHM1147-19-U probe 1.

SEQ ID NO:108 is the sequence of PHM1147-19-U probe 2.

SEQ ID NO:109 is the sequence of the PHM11850-3-U forward primer.

SEQ ID NO:110 is the sequence of the PHM11850-3-U reverse primer.

SEQ ID NO:111 is the sequence of PHM11850-3-U probe 1.

SEQ ID NO:112 is the sequence of PHM11850-3-U probe 2.

SEQ ID NO:113 is the sequence of the PHM11850-6-U forward primer.

SEQ ID NO:114 is the sequence of the PHM11850-6-U reverse primer.

SEQ ID NO:115 is the sequence of PHM11850-6-U probe 1.

SEQ ID NO:116 is the sequence of PHM11850-6-U probe 2.

SEQ ID NO:117 is the sequence of the PHM9301-37-U forward primer.

SEQ ID NO:118 is the sequence of the PHM9301-37-U reverse primer.

SEQ ID NO:119 is the sequence of PHM9301-37-U probe 1.

SEQ ID NO:120 is the sequence of PHM9301-37-U probe 2.

SEQ ID NO:121 is the sequence of the PHM5280-41-U forward primer.

SEQ ID NO:122 is the sequence of the PHM5280-41-U reverse primer.

SEQ ID NO:123 is the sequence of PHM5280-41-U probe 1.

SEQ ID NO:124 is the sequence of PHM5280-41-U probe 2.

SEQ ID NO:125 is the sequence of the PHM13773-6-U forward primer.

SEQ ID NO:126 is the sequence of the PHM13773-6-U reverse primer.

SEQ ID NO:127 is the sequence of PHM13773-6-U probe 1.

SEQ ID NO:128 is the sequence of PHM13773-6-U probe 2.

SEQ ID NO:129 is the sequence of the PHM13773-11-U forward primer.

SEQ ID NO:130 is the sequence of the PHM13773-11-U reverse primer.

SEQ ID NO:131 is the sequence of PHM13773-11-U probe 1.

SEQ ID NO:132 is the sequence of PHM13773-11-U probe 2.

SEQ ID NO:133 is the sequence of the PHM16422-11-U forward primer.

SEQ ID NO:134 is the sequence of the PHM16422-11-U reverse primer.

SEQ ID NO:135 is the sequence of PHM16422-11-U probe 1.

SEQ ID NO:136 is the sequence of PHM16422-11-U probe 2.

SEQ ID NO:137 is the sequence of the PHM9009-13-U forward primer.

SEQ ID NO:138 is the sequence of the PHM9009-13-U reverse primer.

SEQ ID NO:139 is the sequence of PHM9009-13-U probe 1.

SEQ ID NO:140 is the sequence of PHM9009-13-U probe 2.

SEQ ID NO:141 is the sequence of the PHM3171-5-U forward primer.

SEQ ID NO:142 is the sequence of the PHM3171-5-U reverse primer.

SEQ ID NO:143 is the sequence of PHM3171-5-U probe 1.

SEQ ID NO:144 is the sequence of PHM3171-5-U probe 2.

SEQ ID NO:145 is the sequence of the PHM3860-43-U forward primer.

SEQ ID NO:146 is the sequence of the PHM3860-43-U reverse primer.

SEQ ID NO:147 is the sequence of PHM3860-43-U probe 1.

SEQ ID NO:148 is the sequence of PHM3860-43-U probe 2.

SEQ ID NO:149 is the sequence of the PHM7942-12-U forward primer.

SEQ ID NO:150 is the sequence of the PHM7942-12-U reverse primer.

SEQ ID NO:151 is the sequence of PHM7942-12-U probe 1.

SEQ ID NO:152 is the sequence of PHM7942-12-U probe 2.

SEQ ID NO:153 is the sequence of the PHM678-22-U forward primer.

SEQ ID NO:154 is the sequence of the PHM678-22-U reverse primer.

SEQ ID NO:155 is the sequence of PHM678-22-U probe 1.

SEQ ID NO:156 is the sequence of PHM678-22-U probe 2.

SEQ ID NO:157 is the sequence of the PHM8358-17-U forward primer.

SEQ ID NO:158 is the sequence of the PHM8358-17-U reverse primer.

SEQ ID NO:159 is the sequence of PHM8358-17-U probe 1.

SEQ ID NO:160 is the sequence of PHM8358-17-U probe 2.

SEQ ID NO:161 is the sequence of the PHM16415-8-U forward primer.

SEQ ID NO:162 is the sequence of the PHM16415-8-U reverse primer.

SEQ ID NO:163 is the sequence of PHM16415-8-U probe 1.

SEQ ID NO:164 is the sequence of PHM16415-8-U probe 2.

SEQ ID NO:165 is the sequence of the PHM737-215-U forward primer.

SEQ ID NO:166 is the sequence of the PHM737-215-U reverse primer.

SEQ ID NO:167 is the sequence of PHM737-215-U probe 1.

SEQ ID NO:168 is the sequence of PHM737-215-U probe 2.

SEQ ID NO:169 is the sequence of the PHM9092-11-U forward primer.

SEQ ID NO:170 is the sequence of the PHM9092-11-U reverse primer.

SEQ ID NO:171 is the sequence of PHM9092-11-U probe 1.

SEQ ID NO:172 is the sequence of PHM9092-11-U probe 2.

SEQ ID NO:173 is the reference sequence of PHM10054.
SEQ ID NO:174 is the reference sequence of PHM10721.
SEQ ID NO:175 is the reference sequence of PHM15661.
SEQ ID NO:176 is the reference sequence of PHM12872.
SEQ ID NO:177 is the sequence of the PHM8711-17-U forward primer.

SEQ ID NO:178 is the sequence of the PHM8711-17-U reverse primer.

SEQ ID NO:179 is the sequence of PHM8711-17-U probe 1.

SEQ ID NO:180 is the sequence of PHM8711-17-U probe 2.

SEQ ID NO:181 is the sequence of the PHM10054-14-U forward primer.

SEQ ID NO:182 is the sequence of the PHM10054-14-U reverse primer.

SEQ ID NO:183 is the sequence of PHM10054-14-U probe 1.

SEQ ID NO:184 is the sequence of PHM10054-14-U probe 2.

SEQ ID NO:185 is the sequence of the PHM10721-9-U forward primer.

SEQ ID NO:186 is the sequence of the PHM10721-9-U reverse primer.

SEQ ID NO:187 is the sequence of PHM10721-9-U probe 1.

SEQ ID NO:188 is the sequence of PHM10721-9-U probe 2.

SEQ ID NO:189 is the sequence of the PHM10721-16-U forward primer.

SEQ ID NO:190 is the sequence of the PHM10721-16-U reverse primer.

SEQ ID NO:191 is the sequence of PHM10721-16-U probe 1.

SEQ ID NO:192 is the sequence of PHM10721-16-U probe 2.

SEQ ID NO:193 is the sequence of the PHM15661-21-U forward primer.

SEQ ID NO:194 is the sequence of the PHM15661-21-U reverse primer.

SEQ ID NO:195 is the sequence of PHM15661-21-U probe 1.

SEQ ID NO:196 is the sequence of PHM15661-21-U probe 2.

DETAILED DESCRIPTION

The present invention provides allelic compositions in maize and methods for identifying and selecting maize plants with enhanced resistance to *Fusarium* ear mold. The following definitions are provided as an aid to understand this invention.

The term "allele" refers to one of two or more different nucleotide sequences that occur at a specific locus.

"Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Maize Genome Browser, which is publicly available on the internet.

An allele is "associated with" a trait when it is linked to it and when the presence of the allele is an indicator that the desired trait or trait form will occur in a plant comprising the allele.

A "BAC", or bacterial artificial chromosome, is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or "contiguous DNA").

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" can also be referred to as a "linkage group".

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic resistance). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "complement" refers to a nucleotide sequence that is complementary to a given nucleotide sequence, i.e. the sequences are related by the base-pairing rules.

The term "contiguous DNA" refers to overlapping contiguous genetic fragments.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A plant referred to herein as "diploid" has two sets (genomes) of chromosomes.

"Disease resistance" is a characteristic of a plant, wherein the plant avoids the disease symptoms that are the outcome of plant-pathogen interactions, such as interactions between maize and the *fusarium* species *F. verticillioides, F. proliferatum*, and/or *F. subglutinans*. That is, pathogens are prevented from causing plant diseases and the associated disease symptoms, or alternatively, the disease symptoms caused by the pathogen are minimized or lessened. One of skill in the art will appreciate that the compositions and methods disclosed herein can be used with other compositions and methods available in the art for protecting plants from pathogen attack.

A plant referred to herein as a "doubled haploid" is developed by doubling the haploid set of chromosomes. A doubled haploid plant is considered a homozygous plant.

An "elite line" or "elite strain" is any line that has resulted from breeding and selection for superior agronomic performance.

"Enhanced resistance" refers to an increased level of resistance against a particular pathogen, a wide spectrum of pathogens, or an infection caused by the pathogen(s). An increased level of resistance against the fungal pathogens *Fusarium verticillioides* (Fv), *Fusarium proliferatum* (Fp), and *Fusarium subglutinans* (Fs), for example, constitutes "enhanced" or improved fungal resistance. The embodiments of the invention will enhance or improve fungal plant pathogen resistance, such that the resistance of the plant to a fungal pathogen or pathogens will increase, which in turn, will increase resistance to the disease caused by the fungal pathogen. The term "enhance" refers to improve, increase, amplify, multiply, elevate, raise, and the like. Herein, plants of the invention are described as having "enhanced resistance" to the *Fusarium* species *F. verticillioides, F. proliferatum*, and *F. subglutinans* and/or the ear mold caused by these pathogens, as a result of specific alleles at the locus of the invention.

An "exotic maize strain" or an "exotic maize germplasm" is a strain or germplasm derived from a maize not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

*F. verticillioides, F. proliferatum*, and *F. subglutinans* are the fungal pathogens that induce *Fusarium* ear mold (or ear rot) in maize. The fungal pathogens are also referred to collectively herein as *Fusarium*.

A "favorable allele" is the allele at a particular locus that confers, or contributes to, an agronomically desirable phenotype, e.g., enhanced resistance to *Fusarium* ear mold. A favorable allele of a marker is a marker allele that segregates with the favorable phenotype.

"Fragment" is intended to mean a portion of a nucleotide sequence. Fragments can be used as hybridization probes or PCR primers using methods disclosed herein.

As used herein, "fungal resistance" refers to enhanced resistance or tolerance to a fungal pathogen when compared to that of a wild type plant. Effects may vary from a slight increase in tolerance to the effects of the fungal pathogen (e.g., partial inhibition) to total resistance such that the plant is unaffected by the presence of the fungal pathogen.

"*Fusarium* ear mold", sometimes referred to as *Fusarium* ear rot, is the disease caused by species of the *Gibberella fuijkuroi* complex, namely *F. verticillioides, F. proliferatum*, and/or *F. subglutinans*.

A "genetic map" is a description of genetic linkage relationships among loci on one or more chromosomes within a given species, generally depicted in a diagrammatic or tabular form. For each genetic map, distances between loci are measured by the recombination frequencies between them, and recombinations between loci can be detected using a variety of molecular genetic markers (also called molecular markers). A genetic map is a product of the mapping population, types of markers used, and the polymorphic potential of each marker between different populations. The order and genetic distances between loci can differ from one genetic map to another. For example, 10 cM on the internally derived genetic map (also referred to herein as "PHB" for Pioneer Hi-Bred) is roughly equivalent to 25-30 cM on the IBM2 2005 neighbors frame map (a high resolution map available on maizeGDB). However, information can be correlated from one map to another using a general framework of common markers. One of ordinary skill in the art can use the framework of common markers to identify the positions of markers and other loci of interest on each individual genetic map.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to polymorphisms at a particular locus, such as a single marker locus, or polymorphisms at multiple loci along a chromosomal segment.

The term "heterogeneity" is used to indicate that individuals within the group differ in genotype at one or more specific loci.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (BSSS) and "Lancaster" or "Lancaster Sure Crop" (sometimes referred to as NSS, or non-Stiff Stalk).

The term "heterozygous" means a genetic condition wherein different alleles reside at corresponding loci on homologous chromosomes.

The term "homogeneity" indicates that members of a group have the same genotype at one or more specific loci.

The term "homozygous" means a genetic condition wherein identical alleles reside at corresponding loci on homologous chromosomes.

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" refers to any of following maps: IBM, IBM2, IBM2 neighbors, IBM2 FPC0507, IBM2 2004 neighbors, IBM2 2005 neighbors, or IBM2 2005 neighbors frame. IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic maps.

The term "inbred" refers to a line that has been bred for genetic homogeneity.

The term "indel" refers to an insertion or deletion, wherein one line may be referred to as having an insertion relative to a second line, or the second line may be referred to as having a deletion relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background. For example, the chromosome 1 locus and/or the chromosome 6 locus described herein may be introgressed into a recurrent parent that is not resistant or only partially resistant to the *Fusarium* species that cause ear mold and/or the ear mold itself. The recurrent parent line with the introgressed gene or locus then has enhanced resistance to the *Fusarium* species that cause ear mold and/or the ear mold itself.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

As used herein, the term "linkage" is used to describe the degree with which one marker locus is associated with another marker locus or some other locus (for example, a *Fusarium* ear mold resistance locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait, e.g., *Fusarium* ear mold resistance. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill, W. G. and Robertson, A, *Theor. Appl. Genet.* 38:226-231 (1968). When $r^2=1$, complete LD exists between the two marker loci, meaning that the markers have not been separated by recombination and have the same allele frequency. Values for $r^2$ above ⅓ indicate sufficiently strong LD to be useful for mapping (Ardlie et al., *Nature Reviews Genetics* 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome where a gene or marker is located.

The "logarithm of odds (LOD) value" or "LOD score" (Risch, Science 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

"Maize" refers to a plant of the *Zea mays* L. ssp. *mays* and is also known as "corn".

The term "maize plant" includes: whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of maize molecular markers are known in the art, and are published or available from various sources, such as the Maize GDB internet resource and the Arizona Genomics Institute internet resource run by the University of Arizona.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus.

"Marker assisted selection" (of MAS) is a process by which phenotypes are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype", or "phenotypic trait" or "trait" refers to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

A marker with the designation "PHM" followed by a number (e.g. PHM6929) represents two sets of primers (external and internal) that when used in a nested PCR, amplify a specific piece of DNA. The external set is used in the first round of PCR, after which the internal sequences are used for a second round of PCR on the products of the first round. This increases the specificity of the reaction. The annealing temperature for the PHM markers (consisting of two sets of primers) is 55° C. SNPs are identified and given the designation as "PHM" followed by the marker number, a dash, and a SNP identifier number. High throughput markers can be developed for useful SNP polymorphisms using any high-throughput platform, including, but not limited to, the Invader®. (Third Wave Technologies) platform, Invader Plus®, or Illumina sequencing technologies. High-throughput SNP markers described herein are given the designation PHM followed by: the number of the PHM marker, a dash, the SNP identifier number, another dash, and then a letter indicating the technology used.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

An allele "positively" correlates with a trait when it is linked to it and when presence of the allele is an indictor that the desired trait or trait form will occur in a plant comprising the allele.

A "polymorphism" is a variation in the DNA that is too common to be due merely to new mutation. A polymorphism must have a frequency of at least 1% in a population. A polymorphism can be a single nucleotide polymorphism, or SNP, or an insertion/deletion polymorphism, also referred to herein as an "indel".

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

The term "progeny" refers to the offspring generated from a cross.

A "progeny plant" is generated from a cross between two plants.

The term "quantitative trait locus" or "QTL" refers to a polymorphic genetic locus with at least one allele that correlates with the differential expression of a phenotypic trait in at least one genetic background, e.g., in at least one breeding population or progeny. A QTL can act through a single gene mechanism or by a polygenic mechanism.

The QTLs on chromosome 1 and chromosome 6 are referred to herein as "QTL1" and "QTL6", respectively.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment. An example of a reference sequence is the PHM6929 reference sequence. The PHM6929 marker was genotyped in a number of lines, and the sequences were aligned to obtain the consensus sequence of the alignment, referred to herein as the "reference sequence".

In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

A "topcross test" is a progeny test derived by crossing each parent with the same tester, usually a homozygous line. The parent being tested can be an open-pollinated variety, a cross, or an inbred line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances.

Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium).

Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151 153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J. Fritsch, E. F. and Maniatis, T. Molecular Cloning: A Laboratory Manual; Cold Spring Harbor Laboratory Press: Cold Spring Harbor, 1989 (hereinafter "Sambrook").

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Turning now to the embodiments:

Fusarium Ear Mold Resistance

Fusarium ear mold (also referred to as Fusarium ear rot) is a devastating disease of maize caused by species of the Gibberella fuijkuroi complex, namely F. verticillioides, F. proliferatum, and/or F. subglutinans. The identification of molecular markers and alleles of molecular markers that are associated with Fusarium ear mold resistance allows selection for resistance based solely on the genetic composition of the progeny. Methods for identifying and selecting maize plants with enhanced resistance to Fusarium ear mold through the evaluation of genetic composition (as assessed using molecular markers and their alleles) are presented herein.

Genetic Mapping

It has been recognized for quite some time that specific genetic loci correlating with particular phenotypes, such as resistance to Fusarium ear mold, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as resistance to Fusarium ear mold. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

The present invention provides maize marker loci that demonstrate statistically significant co-segregation with resistance to *Fusarium* ear mold, as determined by traditional linkage analysis. Detection of these loci or additional linked loci can be used in marker assisted maize breeding programs to produce plants with enhanced resistance to *Fusarium* ear mold.

Marker Compositions

Markers associated with resistance to *Fusarium* ear mold are identified herein. The methods involve detecting the presence of one or more marker alleles associated with the enhanced resistance in the germplasm of a maize plant. The maize plant can be a hybrid or inbred.

For the QTL identified on chromosome 1, the marker locus can be selected from any of the marker loci provided in FIGS. 1A, 1B, and 1C, Table 2A, or Table 3, including the PHM and SSR markers PHM6929, bnlg1007, PHM8711, bnlg1083, PHM8211, PHM14506, PHM1754, PHM3951, PHM1934, PHM10054, PHM10721, and PHM15661; and the SNP markers PHM8211-16-I, PHM8711-14-U, PHM14506-7-U, PHM1934-37-U, PHM8711-17-U, PHM1754-20-U, PHM3951-25-U, PHM6929-3-U, PHM10054-14-U, PHM10721-9-U, PHM10721-16-U, and PHM15661-21-U; as well as any other marker linked to these markers (linked markers can be determined from the MaizeGDB resource).

For the QTL identified on chromosome 6, the marker locus can be selected from any of the marker loci provided in FIGS. 2A and 2B or Table 2B, including the PHM and SSR markers PHM4423, bnlg1732, PHM9362, PHI445613, PHM1147, PHM11850, PHM9301, umc1762, PHM5280, PHM13773, and PHM16422; and the SNP markers PHM9362-8-U, PHM1147-16-U, PHM11850-3-U, PHM11850-6-U, PHM13773-6-U, PHM13773-11-U, PHM16422-11-U, PHM1147-19-U, PHM5280-41-U, PHM9301-37-U, and PHM4423-4-U; as well as any other marker linked to these markers (linked markers can be determined from the MaizeGDB resource).

Physical Map Locations of QTLs

The genetic elements or genes located on a contiguous linear span of genomic DNA on a single chromosome are physically linked.

In the linkage mapping analysis, PHM8211 and PHM1934 were found to delineate a *Fusarium* ear mold resistance locus on chromosome 1. However, PHM6929-3 also co-segregates with the enhanced resistance in a number of lines, and PHM6929-3 lies outside of the PHM8211-PHM1934 interval. Thus, the chromosome 1 QTL interval can be expanded to include any marker that lies between the interval comprising and flanked by PHM6929 and PHM1934 (FIGS. 1A, 1B, and 1C). Any polynucleotide that assembles to the contiguous DNA between and including SEQ ID NO:41 (the reference sequence for PHM6929), or a nucleotide sequence that is 95% identical to SEQ ID NO:41 based on the Clustal V method of alignment, and SEQ ID NO:47 (the reference sequence for PHM1934), or a nucleotide sequence that is 95% identical to SEQ ID NO:47 based on the Clustal V method of alignment, can house marker loci that are associated with the *Fusarium* ear mold resistance trait. FIGS. 1A, 1B, and 1C show the physical map arrangement of the sequenced BACs that make up the contiguous stretch of DNA between and including PHM6929 and PHM1934. The gaps (represented by dotted lines) are not gaps in the contiguous stretch of DNA per se but are areas where BACs that have not been sequenced assemble to the physical map.

In the linkage mapping analysis, bnlg1732 and umc1762 were found to delineate a *Fusarium* ear mold resistance locus on chromosome 6. However, PHM4423-4 and PHM13773-6 also co-segregate with the enhanced resistance in a number of lines, and PHM4423-4 and PHM13773-6 lie outside of the bnlg1732-umc1762 interval. In addition, PHM16422 and PHM13773 are closely linked. Thus, the chromosome 6 QTL interval can be expanded to include any marker that lies in the interval comprising and flanked by PHM4423 and PHM16422. Any polynucleotide that assembles to the contiguous DNA between and including SEQ ID NO:48 (the reference sequence for PHM4423), or a nucleotide sequence that is 95% identical to SEQ ID NO:48 based on the Clustal V method of alignment, and SEQ ID NO:55 (the reference sequence for PHM16422), or a nucleotide sequence that is 95% identical to SEQ ID NO:55 based on the Clustal V method of alignment, can house marker loci that are associated with the *Fusarium* ear mold resistance trait. FIGS. 2A and 2B show the physical map arrangement of the sequenced BACs that make up the contiguous stretch of DNA between and including PHM4423 and PHM16422. The gaps (represented by dotted lines) are not gaps in the contiguous stretch of DNA per se but are areas where BACs that have not been sequenced assemble to the physical map.

Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can show co-segregation with the *Fusarium* ear mold resistance phenotype, it is important to note that the marker locus is not necessarily responsible for the expression of the *Fusarium* ear mold resistance phenotype. For example, it is not a requirement that the marker polynucleotide sequence be part of a gene that imparts enhanced *Fusarium* ear mold resistance (for example, be part of the gene open reading frame). The association between a specific marker allele and the enhanced *Fusarium* ear mold resistance phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

For the QTL on chromosome 1, markers listed in FIGS. 1A, 1B, and 1C, Table 2A, or Table 3 can be used to predict the state of the *Fusarium* ear mold resistance trait in a maize plant. This includes any marker within 50 cM of the PHM and SSR markers PHM6929, bnlg1007, PHM8711, bnlg1083, PHM8211, PHM14506, PHM1754, PHM3951, PHM1934, PHM10054, PHM10721, and PHM15661; as well as the SNP markers PHM8211-16-I, PHM8711-14-U, PHM14506-7-U, PHM1934-37-U, PHM8711-17-U, PHM1754-20-U, PHM3951-25-U, PHM6929-3-U, PHM10054-14-U, PHM10721-9-U, PHM10721-16-U, and PHM15661-21-U.

For the QTL on chromosome 6, markers listed in FIGS. 2A and 2B or Table 2B can be used to predict the state of the *Fusarium* ear mold resistance trait in a maize plant. This includes any marker within 50 cM of the PHM and SSR markers PHM4423, bnlg1732, PHM9362, PHI445613, PHM1147, PHM11850, PHM9301, umc1762, PHM5280, PHM13773, and PHM16422; and the SNP markers PHM9362-8-U, PHM1147-16-U, PHM11850-3-U, PHM11850-6-U, PHM13773-6-U, PHM13773-11-U, PHM16422-11-U, PHM1147-19-U, PHM5280-41-U, PHM9301-37-U, and PHM4423-4-U.

Chromosomal Intervals

Chromosomal intervals that correlate with *Fusarium* ear mold resistance are provided. A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for *Fusarium* ear mold resistance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

The intervals described below show a clustering of markers that co-segregate with *Fusarium* ear mold resistance. This clustering of markers occurs in relatively small domains on the chromosomes, indicating the presence of one or more QTL in those chromosome regions. The interval was drawn to encompass markers that co-segregate with *Fusarium* ear mold resistance. The intervals are defined by the markers on their termini, where the interval encompasses markers that map within the interval as well as the markers that define the termini. An interval described by the terminal markers that define the endpoints of the interval will include the terminal markers and any marker localizing within that chromosomal domain, whether those markers are currently known or unknown.

For the QTL on chromosome 1, an interval may be defined by and includes markers a) PHM6929 and PHM1934; or b) PHM6929 and PHM14506. For the QTL on chromosome 6, an interval may be defined by and includes PHM4423 and PHM16422. Any marker located within these intervals finds use as a marker for *Fusarium* ear mold resistance.

Chromosomal intervals can also be defined by markers that are linked to (show linkage disequilibrium with) a QTL marker, and $r^2$ is a common measure of linkage disequilibrium (LD) in the context of association studies. If the $r^2$ value of LD between a chromosome 1 marker locus lying within the interval of PHM6929 and PHM1934, for example, and another chromosome 1 marker locus in close proximity is greater than ⅓ (Ardlie et al., Nature Reviews Genetics 3:299-309 (2002)), the loci are in linkage disequilibrium with one another.

Marker Alleles and Haplotypic Combinations

A marker of the invention can also be a combination of alleles at one or more marker loci. The alleles described below could be used alone or in combination to identify and select maize plants with enhanced *Fusarium* ear mold resistance.

Favorable SNP alleles (i.e., associated with enhanced *Fusarium* ear mold resistance) at the QTL on chromosome 1 have been identified herein and include: a "T" at PHM8211-16, a "C" at PHM8711-14, a "T" at PHM14506-7, a "C" at PHM1934-37, a "C" at PHM8711-17, a "C" at PHM1754-20, a "T" at PHM3951-25, a "C" at PHM6929-3, an "A" at PHM10054-14, an "A" at PHM10721-9, an "A" at PHM10721-16, and a "G" at PHM15661-21.

Favorable SNP alleles (i.e., associated with enhanced *Fusarium* ear mold resistance) at the QTL on chromosome 6 have been identified herein and include: a "G" at PHM9362-8, a "G" at PHM1147-16, a "T" at PHM11850-3, a "C" at PHM11850-6, an "A" at PHM13773-6, a "C" at PHM13773-11, an "A" at PHM16422-11, a "T" at PHM1147-19, a "G" at PHM5280-41, a "T" at PHM9301-37, and a "T" at PHM4423-4.

While a haplotype associated with enhanced *Fusarium* ear mold resistance may comprise any of the alleles described above, the following haplotypes are linked to enhanced *Fusarium* ear mold resistance and can be used in marker assisted selection to select for maize plants with enhanced *Fusarium* ear mold resistance:

a) a "C" at PHM6929-3, a "T" at PHM8211-16, and a "T" at PHM 14506-7;

b) a "T" at PHM4423-4, a "T" at PHM11850-3, and an "A" at PHM 13773-6;

c) an "A" at PHM10054-14 and an "A" at PHM10721-9;

d) an "A" at PHM10054-14, a "T" at PHM8211-16, and an "A" at PHM 10721-9;

e) a "G" at PHM9362-8 and an "A" at PHM13773-6.

The skilled artisan would expect that there might be additional polymorphic sites at marker loci in and around the chromosome 1 and chromosome 6 markers identified herein, wherein one or more polymorphic sites is in linkage disequilibrium (LD) with an allele at one or more of the polymorphic sites in the haplotype. Two particular alleles at different polymorphic sites are said to be in LD if the presence of the allele at one of the sites tends to predict the presence of the allele at the other site on the same chromosome (Stevens, *Mol. Diag.* 4:309-17 (1999)).

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. kernel characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide*. Academic press. pp 75-135).

Various types of SSR markers can be generated, and SSR profiles from resistant lines can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode.™. (Qiagen), Invader®. (Third Wave Technologies) and Invader Plus®, SnapShot®. (Applied Biosystems), Taqman®. (Applied Biosystems) and Beadarrays®. (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele 'T' for a specific line or variety with resistance to *Fusarium* ear mold, but the allele 'T' might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Many of the PHM markers can readily be used as FLP markers to select for the gene loci on chromosomes 1 and 6, owing to the presence of insertions/deletion polymorphisms. Primers for the PHM markers can also be used to convert these markers to SNP or other structurally similar or functionally equivalent markers (SSRs, CAPs, indels, etc), in the same regions. One very productive approach for SNP conversion is described by Rafalski (2002a) *Current opinion in plant biology* 5 (2): 94-100 and also Rafalski (2002b) *Plant Science* 162: 329-333. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically with respect to the fine map information described herein, one can readily use the information provided herein to obtain additional polymorphic SNPs (and other markers) within the region amplified by the primers listed in this disclosure. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

In general, MAS uses polymorphic markers that have been identified as having a significant likelihood of co-segregation with a phenotype, such as *Fusarium* ear mold resistance. Such markers are presumed to map near a gene or genes that give the plant its *Fusarium* ear mold resistance phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. The means to identify maize plants that have enhanced resistance to *Fusarium* ear mold by identifying plants that have an allele associated with enhanced resistance to *Fusarium* ear mold at any one of the chromosome 1 marker loci described herein, including the PHM and SSR markers PHM6929, bnlg1007, PHM8711, bnlg1083, PHM8211, PHM14506, PHM1754, PHM3951, PHM1934, PHM10054, PHM10721, and PHM15661; and the SNP markers PHM8211-16-I, PHM8711-14-U, PHM14506-7-U, PHM1934-37-U, PHM8711-17-U, PHM1754-20-U, PHM3951-25-U, PHM6929-3-U, PHM10054-14-U, PHM10721-9-U, PHM10721-16-U, and PHM15661-21-U, and/or at any one of the chromosome 6 marker loci described herein, including the PHM and SSR markers PHM4423, bnlg1732, PHM9362, PHI445613, PHM1147, PHM11850, PHM9301, umc1762, PHM5280, PHM13773, and PHM16422; and the SNP markers PHM9362-8-U, PHM1147-16-U, PHM11850-3-U, PHM11850-6-U, PHM13773-6-U, PHM13773-11-U, PHM16422-11-U, PHM1147-19-U, PHM5280-41-U, PHM9301-37-U, and PHM4423-4-U; are presented herein.

The intervals presented herein find use in MAS to select plants that demonstrate enhanced resistance to *Fusarium* ear mold. Any marker that maps within the chromosome 1 interval defined by and including:
  i. PHM6929 and PHM1934, or
  ii. PHM6929 and PHM14506
can be used for this purpose. Similarly, any marker that maps within the chromosome 6 interval defined by and including PHM4423 and PHM16422 can be used for this purpose.

Haplotypes can also be used in MAS to introduce enhanced resistance to *Fusarium* ear mold into susceptible maize lines or varieties. A haplotype can comprise at least one of the following marker alleles: a "T" at PHM8211-16, a "C" at PHM8711-14, a "T" at PHM14506-7, a "C" at PHM1934-37, a "C" at PHM8711-17, a "C" at PHM1754-20, a "T" at PHM3951-25, a "C" at PHM6929-3, an "A" at PHM10054-14, an "A" at PHM10721-9, an "A" at PHM10721-16, a "G" at PHM15661-21, a "G" at PHM9362-8, a "G" at PHM1147-16, a "T" at PHM11850-3, a "C" at PHM11850-6, an "A" at PHM13773-6, a "C" at PHM13773-11, an "A" at PHM16422-11, a "T" at PHM1147-19, a "G" at PHM5280-41, a "T" at PHM9301-37, and a "T" at PHM4423-4. In addition, the following haplotypes can be used in marker assisted selection to select for maize plants with enhanced *Fusarium* ear mold resistance:

a) a "C" at PHM6929-3, a "T" at PHM8211-16, and a "T" at PHM14506-7;
  b) a "T" at PHM4423-4, a "T" at PHM11850-3, and an "A" at PHM 13773-6;
  c) an "A" at PHM10054-14 and an "A" at PHM10721-9;
  d) an "A" at PHM10054-14, a "T" at PHM8211-16, and an "A" at PHM10721-9;
  e) an "A" at PHM9362-8 and an "A" at PHM13773-6.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

Mapping of Large Effect QTLs for *Fusarium* Ear Mold Resistance

Mapping Population

A mapping population consisting of 360 $F_{7:8}$ recombinant inbred lines (RILs) was derived from a cross between PHG61, a highly resistant line in the non-stiff stalk group, and 1047, a susceptible stiff stalk inbred. (FIG. 3 shows a comparison between ears from resistant line PHG61 and ears from susceptible line 1047). Sequential selfing of the families was done in non-selective environments. Usually the first five plants in each row were selfed and ears from the two plants closest to the center of the row were harvested. Naturally, some lines producing barren ears were lost.

Genotyping

DNA was extracted from lyophilized leaf samples of $F_{7:8}$ seedlings, and genotypic data was collected at each of 533 AFLP markers, covering a total of 1380.6 cM, with an average distance between markers of 2.6 cM.

Phenotyping

Lines in the RIL population were evaluated for visual ear mold under natural infection conditions at two testing sites in the United States, Winterville (WT), Pitt County, North Carolina, and Walnut Grove (Calif.), San Joaquin County, California, in both 1998 and 1999. Fungal growth and starbursting (white streaks on the pericarp, running parallel to the long axis of the kernel) were considered as signs and symptoms of ear mold. Ear piles were scored for visual ear mold according to the 1-9 scale shown in FIG. 4.

QTL Mapping

QTL analysis was performed on untransformed data using the software package PLABQTL (Utz and Melchinger (1996) *J. Quant. Trait Loci* 2(1)) version 1.1 released in 1999. Composite interval mapping (cov SEL command) was used to detect putative QTLs. A QTL was declared real if it was detected at both locations and if it was significant in at least one location. QTL analysis identified major QTLs for *Fusarium* ear mold resistance on chromosomes 1, 5, 6, 7, and 8. The QTL on chromosome 1 is referred to herein as QTL1 and lies between the AFLP markers 177 and T292. The QTL on chromosome 6 is referred to herein as QTL6 and lies between the AFLP markers D166 and C116. SEQ ID NOs:1-8 are the primer sequences for the AFLP markers that delineate QTL1 and QTL6.

Example 2

Validation and Fine Mapping of QTL1 and QTL6

In order to test the effect and utility of the QTLs identified, near isogenic lines (NILs) were developed in three susceptible genetic backgrounds: 1047 (described above), PH24E, and PH1BC. PHG61 has a historical *Fusarium* ear mold score of 8-9 (based on the 1-9 scale); while 1047, PH24E, and PH1BC have historical scores of 3-4, 4.0, and 5.0.

RILs from Example 1 that carried QTL1 or QTL6 were crossed back to the original susceptible parent 1047 twice, followed by sequential selfing for 3 generations, thereby creating BC3S3 lines.

NILs were also generated by crossing the resistant parent PHG61 to two other susceptible inbreds (PH24E and PH1BC). For each cross, individuals of the F1 population were backcrossed to the respective recurrent parent to generate a BC2 population, and sequential selfing of the BC2 families was then performed for 3 generations.

Marker assisted selection (MAS) was used in the development of the NILs to select for the respective QTL region in each generation. A set of 76 SSRs was used for MAS. Four of the SSRs were used to select for either QTL1 or QTL6 (derived from PHG61), while the remaining 72 were used to select against PHG61. Specifically, bnlg1953 was used for selection of QTL1, while LGI112958, PHI445613, and PHI364545 were used for selection of QTL6. The positions of these markers on the latest IBM2 map, along with their respective primer sequences, are found in Table 1.

TABLE 1

SSRs used to select for QTL1 and QTL6 regions of PHG61

| Marker | Chromosome | IBM2 2008 | Primers |
|---|---|---|---|
| bnlg1953 | 1 | 170 | SEQ ID NOs: 9 and 10 |
| LGI112958 | 6 | n/a | SEQ ID NOs: 11 and 12 |
| PHI445613 | 6 | 375.8 | SEQ ID NOs: 13 and 14 |
| PHI364545 | 6 | 428.4 | SEQ ID NOs: 15 and 16 |

Homozygous BC3S3 (for the NILs developed in 1047 background) and BC2S3 (for the NILs developed in PH24E and PH1BC backgrounds) recombinants were then identified. The homozygous recombinants were scored for visual ear mold under natural infection conditions at four testing sites in the United States: Camden, Camden County, N.C.; Cairo, Grady County, Georgia; Woodland, San Joaquin County, California; and Waimea, Kauai, Hi., using the scale in FIG. 4. When compared to the recurrent parents 1047, PH24E, and PH1BC, NILs containing QTL1 increased *Fusarium* ear mold scores by 1-2 points (on a scale of 1 to 9; FIG. 4), while NILs containing QTL6 increased *Fusarium* ear mold scores by 2-4 points.

An integrated genetic and physical map of maize was used to identify all BAC contigs located in both the QTL1 and QTL6 regions. Low-copy BAC end sequences and PHM markers from these contigs were used to develop CAPS markers and/or SNP markers for use with the Invader® or Invader Plus® Technology. The homozygous recombinants were assessed at a number of the marker positions in both of the regions. For QTL1, recombination data placed QTL1 in the region defined by and including markers PHM8211 (SEQ ID NOs:33-36) and PHM1934 (SEQ ID NOs:37-40), while QTL6 was placed in the region of chromosome 6 defined by and including markers bnlg1732 (SEQ ID NOs: 17 and 18) and umc1762 (SEQ ID NOs: 19 and 20).

Example 3

Elite Inbred Conversions

Despite housing resistance alleles for *Fusarium* ear mold, PHG61 is a poor performer agronomically. As a result, a number of elite inbreds were "converted" to have enhanced resistance to *Fusarium* ear mold through the introgression of QTL1 and/or QTL6 from PHG61. The conversions could then be used by breeders to move the QTL(s) from PHG61 into their breeding germplasm. Conversions were made of the elite inbreds PHCA5, PH51H, PH70R, PH87H, PHFCJ, PH890, and PHB1V by crossing PHG61 (the donor parent) to each respective inbred (the recurrent parents). The progeny were then backcrossed to the recurrent parent five times and then selfed for three generations. In each BC population, SSR markers were used to select for the QTL regions. Selections for QTL1 were made using bnlg1007 (SEQ ID NOs:21 and 22), bnlg1083 (SEQ ID NOs:23 and 24) and PHI256546 (SEQ ID NOs:25 and 26), and selections for QTL6 were made using bnlg1174 (SEQ ID NOs:27 and 28) and umc1805 (SEQ ID NOs:29 and 30). However, in the BC5 population and BC5F2 populations, selections for QTL6 were made using umc1462 (SEQ ID NOs:31 and 32) and PHI445613 (SEQ ID NOs:13 and 14). BC5F3 individuals were then selected using SNP markers instead of SSRs. For QTL1, the alleles selected for were: a "T" at PHM8211-16, a "C" at PHM8711-14, a "T" at PHM14506-7, and a "C" at PHM1934-37. For QTL6, the alleles selected for were: a "G" at PHM9362-8, a "G" at PHM1147-16, a "C" at PHM11850-6, a "C" at PHM13773-11, and an "A" at PHM16422-11. See FIGS. 5A and 5B (for QTL1) and FIGS. 6A and 6B (for QTL6) for the marker information for each of these SNPs.

Seeds from the selected BC5F3 individuals and the corresponding non-converted inbreds were planted in split plots with genotypes (QTL) nested within inbreds. There were 3 replications in each of 3 locations (Cremona, Italy; Cairo, Ga.; and Woodland, Calif.); however, the Cairo, Ga. and Cremona, Italy locations had no disease pressure and could not be scored. In Woodland, Calif., the disease pressure was good across the fields, but several inbreds were either barren or had scattered grain. Ideally, the phenotype would be measured by evaluating scores of ear piles having 6 or more ears with a grain fill score of 3 or higher. However, due to the scattered grain issues, scores were taken on very poor ear piles, and many entries were not scorable at all. PHB1V had good ear piles, and scoring was sufficient. Phenotypic scoring was performed using the scale provided in FIG. 4, and genotyping was performed at markers PHM8711-17, PHM8211-16, PHM1754-20, and PHM3951-25 for QTL1 and at markers PHM9362-8, PHM1147-16, PHM1147-19, PHM11850-6, PHM5280-41, and PHM9301-37 for QTL6. See FIGS. 5A, 5B, 6A, and 6B for the SNP marker information; specifically, the figures list the SEQ ID identifiers for each of the primer and probe sequences. A number of other markers were assessed to determine if the other identified QTLs (see example 1) conflicted the phenotypic results. These markers were: PHM9009-13, PHM3171-5, and PHM3860-43 for QTLS; PHM7942-12, PHM678-22, and PHM8358-17 for QTL7; and PHM16415-8, PHM737-215, and PHM9092-11 for QTL8. See FIGS. 7A-7C for the primer and probe sequences for use with the Invader Plus® platform. FIGS. 8-14 show the results for the elite inbred conversions. In each table, "corr_yearmold" is a corrected score of ear piles having 6 or more ears with sufficient grain fill. "stddev" indicates standard deviation. Cells highlighted in dark gray indicate the PHG61 allele, and cells highlighted in light gray indicate that either the marker locus is segregating at that allele or that the technology used to detect the SNP could not determine which allele was present. Only those SI_IDs (Seed Inventory_Identification Numbers; indicates the seed source) for which phenotypic data was obtained are shown. "EQV" means that the polymorphism could not be called; "NF" means that the data was not found.

PHCA5, PH51H, PH70R, and their respective conversions had severe issues with scattered grain, making it extremely difficult to score PHCA5 has a historical *Fusarium* ear mold score of 4.0; however, in this experiment, it was unscorable. PHG61 and PHCA5 are not polymorphic at PHM8711-17, PHM1754-20, PHM1147-16, PHM3171-5, PHM678-22, and PHM9092-11. 11510073 and 11710277 appeared to be segregating at QTL1 and possibly had the PHG61-derived QTL6. 11510073 and 11710277 had scores of 4.0 and 5.5, respectively. 11510074 and 11710275, both with scores of 4, had PHG61-derived QTL1 but not QTL6. 11510082, with a score of 4.0, did not have PHG61-derived QTL1 and possibly had QTL6. FIG. 8 shows the PHCA5 conversion data.

PH51H has a historical *Fusarium* ear mold score of 3.6; however, in this experiment, it had a score of 4.7. PHG61 and PH51H are not polymorphic at PHM5280-41, PHM3171-5, PHM3860-43, PHM678-22, and PHM737-215. 11066837, 11066811, 11066836, and 11066839 appeared to have conflicting phenotypic data, owing to the interference of QTL7. 11066837, with a score of 5.0, was likely segregating for QTL1, possibly had QTL6, and appeared to have QTL7. 11066809, with a score of 5.5, was likely segregating for QTL1 and possibly had the PHG61-derived QTL6. 11066839, with a score of 6.0, appeared to be segregating for QTL1, did not have QTL6, and appeared to have QTL7. 11066838, with a score of 6.3, was segregating for both QTL1 and QTL7 and possibly had the PHG61-derived QTL6. 11066841, with a score of 6.7, and 11066811, with a score of 7.5, did not have QTL1, and appeared to be segregating for QTL6 and QTL7. The scores of the conversions, as compared to PH51H, were significantly increased as a result of the presence of QTL1, QTL6, and/or QTL7. FIG. 9 shows the PH51H conversion data.

PH70R has a historical *Fusarium* ear mold score of 3.6; however, in this experiment, it had a score of 3.0. PHG61 and PH70R are not polymorphic at PHM8711-17, PHM1754-20, PHM3951-25, PHM11850-6, PHM5280-41, PHM9301-37, PHM3171-5, PHM3860-43, PHM678-22, PHM16415-8, PHM737-215, and PHM9092-11. 11067135, with a score of 3.0, did not have QTL1 and likely had the PHG61-derived QTL6. 11067046 had a score of 3.0 and appeared to have PHG61-derived QTL1. 11067168, with a score of 4.0, appeared to be segregating at both QTL1 and QTL6. 11067139, 11067095, and 11062329 had scores of 3.5, 4.7, and 5.0, respectively, and all appeared to have PHG61-derived QTL1 and were segregating for QTL6. 11067060, 11067174, and 11067126 had scores of 5.0, 5.0, and 5.5, respectively, and appeared to have PHG61-derived QTL1 and possibly QTL6. FIG. 10 shows the PH70R conversion data.

PH87H, PHFCJ, PH890, and their respective conversions had scattered grain problems, although less severe.

PH87H has a historical *Fusarium* ear mold score of 5.0; however, in this experiment, it had a score of 5.5. PHG61 and PH87H are not polymorphic at PHM8711-17, PHM1147-16, PHM678-22, and PHM9092-11. 11066328, with a score of 3.7, had PHG61-derived QTL1 and QTL5, and appeared to be segregating for QTL6 and QTL8. 11066329, with a score of 4.0, appeared to be segregating at QTL1 and QTL8 and possibly had PHG61-derived QTL6. 11066314, with a score of 4.0, had PHG61-derived QTL1 and QTL5 and possibly QTL6 and QTL8. 11066230, with a score of 4.3, did not have PHG61-derived QTL1 or QTL6 but possibly had QTL5. 11066235 and 11066277, both with scores of 6.0, did not have PHG61-derived QTL6 but possibly had QTL1 and QTL8. 11066377, with a score of 6.0, appeared to be segregating at QTL1 and QTL5 and possibly had PHG61-derived QTL6. 11062279, with a score of 6.0, had PHG61-derived QTL1 and QTL5 and possibly QTL6. 11066321, with a score of 6.0, had PHG61-derived QTL1, and appeared to be segregating at QTL5, QTL6, and QTL8. FIG. 11 shows the PH87H conversion data.

PHFCJ has a historical *Fusarium* ear mold score of 4.0; however, in this experiment, it had a score of 5.3. PHG61 and PHFCJ are not polymorphic at PHM8211-16, PHM9362-8, PHM1147-16, PHM9301-37, PHM8358-17, PHM16415-8, and PHM737-215. 11066486, with a score of 3.7, appeared to be segregating at QTL1 and had the PHG61-derived QTL6. 11066514, with a score of 4.0, had PHG61-derived QTL6 and possibly QTL1. 110665522, with a score of 4.0, appeared to be segregating at QTL1 and QTL6. FIG. 12 shows the PHFCJ conversion data.

PH890 has a historical *Fusarium* ear mold score of 4.5; however, in this experiment it had a score of 3.5. PHG61 and PH890 are not polymorphic at PHM8711-17, PHM1754-20, PHM1147-16, and PHM9092-11. 11066544, with a score of 4.4, did not have PHG61-derived QTL6 and possibly had QTL1. 11062297, with a score of 4.0, did not have PHG61-derived QTL1 and appeared to be segregating at QTL6. 11066659 and 11066639 had scores of 3.0 and 4.0, respectively, and did not have PHG61-derived QTL1 but had QTL6. 11062294 had a score of 5.0 and had PHG61-derived QTL6 and QTL1. 11066672 had a score of 3.7 and appeared to be segregating at QTL1. 11066707, 11066601, 11066680, and 11066565 with scores of 2.5 4.0, 4.0, and 5.0 respectively, had PHG61-derived QTL1 and appeared to be segregating at QTL6. 11066600, with a score of 4.5, had PHG61-derived QTL1 and QTL6. FIG. 13 shows the PH890 conversion data.

PHB1V has a historical *Fusarium* ear mold score of 4.0; however, in this experiment it had a score of 4.2. PHG61 and PHB1V are not polymorphic at PHM11850-6, PHM5280-41, PHM9301-37, PHM3171-5, PHM3860-43, PHM8358-17, PHM16415-8, and PHM737-215. 11066911 and 11066896 had scores of 4.0 and 4.4, respectively, and neither had PHG61-derived QTL1 or QTL6. 11066988, with a score of 6.0, did not have QTL1-derived QTL1 and possibly had QTL6. 11066895, 11066923, 11067017, and 11067023 had scores of 4.0, 5.3, 6.6, and 6.8, respectively, and had PHG61-derived QTL1 but not QTL6. 11066930 had a score of 5.0 and had PHG61-derived QTL1. 11066981 had a score of 7.0, appeared to be segregating at QTL1, and possibly had PHG61-derived QTL6. 11067002 had a score of 8.0, PHG61-derived QTL1, and it was possibly segregating at QTL6. FIG. 14 shows the PHB1V conversion data.

Example 4

Efficacy in Hybrids

Conversions of PHFCJ, PH70R, PH890, and PH51H were crossed to inbred lines to create hybrids and then compared to similar crosses in which the non-converted PHFCJ, PH70R, PH890, and PH51H inbred lines were used as parents. See FIGS. 15A and 15B for a comparison of *Fusarium* ear mold scores between those lines having the "good" resistance haplotype (similar to PHG61) and those lines not having the "good" resistance haplotype. The markers that were assessed for QTL1 include: PHM6929-3, PHM8211-16, and PHM14506-7. The markers that were assessed for QTL6 include: PHM4423-4, PHM9362-8, PHM1147-19, and PHM11850-6.

When a non-converted PHFCJ line was crossed to PH1JC, the resulting hybrid had an average *Fusarium* ear mold score of 2.8. For plants arising from the crosses between the PHFCJ conversion lines and PH1JC, PHM9362-8 and PHM1147-19 gave unexpected allelic results, and PHM8211-16 was not informative. However, 12022402 and 12022385, with scores of 3.2 and 3.5, respectively, had QTL6, while 12022384 had a score of 3.3 and appeared to have QTL1.

When a non-converted PH70R line was crossed to PH3RC, the resulting hybrid had an average *Fusarium* ear mold score of 5.5. In the crosses between PH70R conversion lines and PH3RC, average scores for all but one cross were equal or greater to 5.5 as a result of having one or both QTLs. 12022393 and 12022394 had scores of 5.5 and 6.2, respectively, presumably due to the presence of QTL1. 12022395, with a score of 7.2, had QTL6 and possibly QTL1. 12022396, 12022397, and 12022398 had scores of 5.0, 7.2, and 5.5, respectively, and all three had both QTL1 and QTL6.

When a non-converted PH890 line was crossed to PH4CN, the resulting hybrid had an average *Fusarium* ear mold score of 3.8. In the crosses between PH890 conversion lines and PH4CN, average scores for the crosses were equal or greater than 3.8. 12022391 only had QTL6 and had a score of 3.8. 12022387, 12022388, 12022389, and 12022390 had both QTL1 and QTL6, resulting in scores of 5.8, 4.7, 5.5, and 4.8, respectively.

When a non-converted PH51H line was crossed to PHEKJ, the resulting hybrid had an average *Fusarium* ear mold score of 2.0. In the crosses between PH51H conversion lines and PHEKJ, average scores for the crosses were greater than 2.0. One cross had a score of 3.3 and possibly had QTL6. The other two crosses had scores of 6.0 and 5.0, respectively, and appeared to have QTL1 and possibly QTL6.

When a non-converted PH51H line was crossed to PHF1J, the resulting hybrid had an average *Fusarium* ear mold score of 7.3, which indicates an already high level of resistance. In the crosses between PH51H conversion lines and PHF1J, one cross had an average score of 7.0 and possibly carried QTL1. Another cross had an average score of 7.3 and possibly both QTL1 and QTL6. A third cross also had an average score of 7.3 and had QTL1 and possibly QTL6.

When a non-converted PH51H line was crossed to PH1W2, the resulting hybrid had an average *Fusarium* ear mold score of 5.3. In the crosses between PH51H conversion lines and PH1W2, each cross had an average score greater than 5.3 and had QTL1 and possibly QTL6.

Example 5

Identification of High-Throughput Markers for Use in Marker Assisted Selection of *Fusarium* Ear Mold Resistant Plants Closely linked markers that have alleles in linkage disequilibrium with a resistance allele at QTL1 and/or QTL6 may be effectively used to select for progeny plants with enhanced resistance to *Fusarium* ear mold. The markers described herein, as well as other markers genetically or physically mapped to the same chromosomal segment, may be used to select for maize plants with enhanced resistance to *Fusarium* ear mold. Tables 2A and 2B show the markers described herein and their positions on both an internally derived genetic map (PHB) and an IBM2 map (regions in gray indicate where the QTLs are located). FIGS. 1A, 1B, and 1C and 2A-2B show the physical maps of the QTL1 region and the QTL6 region, respectively; the SEQ ID NOs for each of the PHM reference sequences are shown in the figures.

TABLE 2A

| QTL1 region in physical map order | | |
|---|---|---|
| Marker | PHB | IBM2 |
| bnlg1953 | 70.45 | 170 |
| PHM6929 | 76.12 | 183.8 |
| bnlg1007 | 76.93 | 139.7 |
| PHM8711 | 79.68 | 198.4 |
| bnlg1083 | 80.54 | 201.3 |
| PHM10054 | 80.33 | n/a |

TABLE 2A-continued

| QTL1 region in physical map order | | |
|---|---|---|
| Marker | PHB | IBM2 |
| PHM8211 | 78.3 | n/a |
| PHM12872 | 81.72 | n/a |
| PHM10721 | 80.77 | 198.4 |
| PHM15661 | 84.31 | n/a |
| PHM14506 | 81.88 | 201.5 |
| PHM1754 | 83.76 | 198.4 |
| PHM3951 | 84.39 | 226.4 |
| PHM1934 | 84.39 | 198.4 |
| PHI256546 | 90.98 | 226.4 |

TABLE 2B

| QTL6 region in physical map order | | |
|---|---|---|
| Marker | PHB | IBM2 |
| LGI112958 | 90.14 | n/a |
| bnlg1174 | 92.95 | 315.4 |
| umc1462 | 102.39 | 325.1 |
| umc1805 | 103.35 | 332.2 |
| PHM4423 | 106.52 | 342.7 |
| bnlg1732 | 116.22 | 373.8 |
| PHM9362 | 115.07 | 391.4 |
| PHI445613 | 117.71 | 375.8 |
| PHM1147 | 120.91 | 394.1 |
| PHM11850 | 122.52 | 388.7 |
| PHM9301 | 124.25 | 394.1 |
| umc1762 | 123.96 | 394.1 |
| PHM5280 | 123.6 | 394.1 |
| PHM13773 | 128.59 | 400.3 |
| PHM16422 | 128.28 | 400.3 |
| PHI364545 | 139.37 | 428.4 |

Typically, a set of these markers will be used, (e.g., 2 or more, 3 or more, 4 or more, 5 or more) in the flanking region above the gene and a similar set in the flanking region below the gene. Optionally, as described above, a marker within the actual gene and/or locus may also be used. The parents and their progeny are screened for these sets of markers, and the markers that are polymorphic between the two parents are used for selection. The most proximal polymorphic markers to the gene or locus are used to select for the gene or locus, and the more distal polymorphic markers are used to select against the gene or locus. In an introgression program, this allows for selection of the gene or locus genotype at the more proximal polymorphic markers and selection for the recurrent parent genotype at the more distal polymorphic markers.

Not all markers genetically and physically mapped to the same chromosomal segment as QTL1 or QTL6 may be used to select for maize plants with enhanced resistance to *Fusarium* ear mold because the marker may not be informative enough within a particular population.

Example 6

Germplasm Survey

Eight hundred eighty four inbred lines from two separate germplasm pools covering a wide range of maturities were screened for resistance to *Fusarium* ear mold between 2003 and 2005 in Cairo, Ga., and in Woodland, Calif.

The lines can be genotyped at QTL1 using PHM6929-3-U, PHM8211-16-1, and PHM14506-7-U, for example. Of the 884 lines, 542 have both phenotypic data and genotypic data for these QTL1 markers. Twenty four lines have a "C"

at PHM6929-3, a "T" at PHM8211-16, and a "T" at PHM14506-7 and an average FUSERS score of 5.3 versus an average score of 4.7 for lines that do not have this haplotype. PHM10054-14-U, PHM8211-16-1, and PHM10721-9-U can also be used to genotype the QTL on chromosome 1. Five hundred and five lines have genotypic data at PHM10054-14-U, PHM8211-16-I, and PHM10721-9-U as well as phenotypic data for FUSERS. Of the 505 lines, seven have an "A" at PHM10054-14, a "T" at PHM8211-16, and an "A" at PHM10721-9. These seven lines have an average FUSERS score of 6.1. The remaining lines (that do not have the "ATA" genotype) have an average score of 4.7.

The lines can be genotyped at QTL6 using PHM4423-4-U, PHM11850-3-U, and PHM13773-6-U, for example. For QTL6, only 125 of the 884 inbred lines have both phenotypic and genotypic data. Only 1 has a "T" at PHM4423-4, a "T" at PHM11850-3, and an "A" at PHM13773-6, and this line has an average FUSERS score of 8.4. Lines that do not have this haplotype have an average FUSERS score of 4.8. PHM9362-8 and PHM13773-6 can also be used to genotype the QTL on chromosome 6. Forty four lines have a "G" at PHM9362-8 and an "A" at PHM13773-6, and this set has an average score of 5.4. The remaining lines without this haplotype have an average score of 4.7.

Example 7

Detection of QTL1 Via Association Mapping Analysis

A collection of 489 maize lines was subjected to association mapping analysis. The lines encompassed elite proprietary Pioneer inbreds of mid to early maturity.

Phenotypic scores were obtained using a FUSERS scale similar to the one provided in FIG. 4. An average score for each line was assigned based on data collected over two years at three locations near Afumati, Romania, under conditions of natural infection.

A structure-based association analysis was conducted using standard association mapping methods, where the population structure is controlled using marker data. The model-based cluster analysis software, Structure, developed by Pritchard et al., (Genetics 155:945-959 (2000)) was used with SNP data at 200 markers to estimate admixture coefficients and assign the inbreds to two subpopulations. This reduces the occurrence of false positives that can arise due to the effect of population structure on association mapping statistics. Kuiper's statistic for testing whether two distributions are the same was used to test a given marker for association between haplotype and phenotype in a given subpopulation (Press et al., Numerical Recipes in C, second edition, Cambridge University Press, NY (2002)).

The two subpopulations identified corresponded to a stiff-stalk class which included 234 lines and a non-stiff stalk class which included 255 lines. Within this last subpopulation, 250 lines had enough data to be analyzed further.

A peak of highly significant marker-trait association was identified in chromosome 1 within the non-stiff stalk subpopulation. Table 3 provides a listing of the maize markers significantly associated with the *Fusarium* ear mold resistance phenotype at the p≤0.001 level, representing an interval of 3.6 cM on the internally derived genetic map. Positions are given in cM, with position zero being the first (most distal from the centromere) marker known at the beginning of the chromosome. The map positions in Table 3 are not absolute and represent an estimate of map position based on the internally derived genetic map (PHB).

TABLE 3

Chromosome 1 markers significantly associated with *Fusarium* ear mold resistance at p ≤ 0.001 in the non-stiff stalk subpopulation group

| Marker Name | Relative map position (cM) on PHB map | P-Value |
| --- | --- | --- |
| PHM8711-17-U | 79.68 | $2.28 \times 10^{-4}$ |
| PHM8711-14-U | 79.68 | $4.80 \times 10^{-5}$ |
| PHM10054-14-U | 80.33 | $4.60 \times 10^{-5}$ |
| PHM10721-9-U | 80.77 | $1.16 \times 10^{-7}$ |
| PHM10721-16-U | 80.77 | $3.80 \times 10^{-7}$ |
| PHM15661-21-U | 84.31 | $2.14 \times 10^{-4}$ |

There were two main haplotypes in the non-stiff stalk subpopulation as defined by markers PHM10054-14-U and PHM10721-9-U. Two hundred and two lines had an 'A' at PHM10054-14, an 'A' at PHM10721-9, and an average FUSERS score of 6.1. Eighteen lines had a 'G' at PHM10054-14, a 'G' at PHM10721-9, and an average FUSERS score of 4.5. Five lines had other haplotypes, and twenty five lines had missing data or had a heterozygous score at one of the markers and could not be assigned a haplotype. Table 4 provides a break down of haplotypes present in the subpopulation.

TABLE 4

Haplotypes present in the non-stiff stalk population and average *Fusarium* ear mold resistance scores for each haplotype class.

| | PHM10054-14 | PHM10721-9 | Number of lines with haplotype | Average FUSERS score |
| --- | --- | --- | --- | --- |
| Hap 1 | A | A | 202 | 6.1 |
| Hap 2 | G | G | 18 | 4.5 |
| Hap 3 | A | G | 1 | 5.3 |
| Hap 4 | G | A | 4 | 5.6 |
| unassigned | — | — | 25 | 6.0 |
| Total | | | 250 | |

What is claimed:

1. A method for producing a maize plant that displays enhanced resistance to *Fusarium* ear mold, the method comprising:
   a) obtaining a sample of nucleic acids from maize germplasm;
   b) detecting in said sample at least one allele of a marker locus located within a chromosomal interval comprising and flanked by PHM4423 and PHM16422, wherein the allele is associated with a haplotype comprising a "T" at PHM4423-4, a "T" at PHM11850-3, and an "A" at PHM13773-6;
   c) selecting said maize germplasm that has the allele that is associated with the haplotype comprising a "T" at PHM4423-4, a "T" at PHM11850-3, and an "A" at PHM13773-6;
   d) crossing said maize germplasm comprising said at least one allele with a second maize plant;
   e) obtaining progeny seeds from said cross; and
   f) growing at least one maize plant from said progeny seeds;
   wherein said maize plant grown from said seeds comprises said at least one allele, and has an enhanced resistance to *Fusarium* ear mold when compared with a maize plant which does not comprise said at least one allele.

2. A method of obtaining a maize plant that displays enhanced resistance to *Fusarium* ear mold, the method comprising:
   a. obtaining a first maize plant that comprises in its genome alleles "T" at PHM4423-4, "T" at PHM11850-3, and "A" at PHM13773-6;
   b. crossing said first maize plant to a second maize plant;
   c. obtaining seeds from said cross;
   d. growing progeny plants from said seeds;
   e. evaluating a sample of nucleic acids from the progeny plants for the alleles "T" at PHM4423-4, "T" at PHM11850-3, and "A" at PHM13773-6 of the first maize plant; and
   f. selecting progeny plants that possess the alleles "T" at PHM4423-4, "T" at PHM11850-3, and "A" at PHM13773-6 of the first maize plant.

* * * * *

SEQUENCE LISTING

<160> NUMBER OF SEQ ID NOS: 196

<210> SEQ ID NO 1
<211> LENGTH: 19
<212> TYPE: DNA
<213> ORGANISM: artificial
<220> FEATURE:
<223> OTHER INFORMATION: I77 forward primer

<400> SEQUENCE: 1
gactgcgtac caattcact                                               19

<210> SEQ ID NO 2
<211> LENGTH: 19
<212> TYPE: DNA
<213> ORGANISM: artificial
<220> FEATURE:
<223> OTHER INFORMATION: I77 reverse primer

<400> SEQUENCE: 2
gatgagtcct gagtaacca                                               19

<210> SEQ ID NO 3
<211> LENGTH: 19
<212> TYPE: DNA
<213> ORGANISM: artificial
<220> FEATURE:
<223> OTHER INFORMATION: T292 forward primer

<400> SEQUENCE: 3
gactgcgtac caattcatg                                               19

<210> SEQ ID NO 4
<211> LENGTH: 19
<212> TYPE: DNA
<213> ORGANISM: artificial
<220> FEATURE:
<223> OTHER INFORMATION: T292 reverse primer

<400> SEQUENCE: 4
gatgagtcct gagtaactc                                               19

<210> SEQ ID NO 5
<211> LENGTH: 19
<212> TYPE: DNA
<213> ORGANISM: artificial
<220> FEATURE:
<223> OTHER INFORMATION: D166 forward primer

<400> SEQUENCE: 5
gactgcgtac caattcaag                                               19

<210> SEQ ID NO 6
<211> LENGTH: 19
<212> TYPE: DNA
<213> ORGANISM: artificial
<220> FEATURE:
<223> OTHER INFORMATION: D166 reverse primer

<400> SEQUENCE: 6
gatgagtcct gagtaactg                                               19

<210> SEQ ID NO 7
<211> LENGTH: 19
<212> TYPE: DNA
<213> ORGANISM: artificial
<220> FEATURE:
<223> OTHER INFORMATION: C116 forward primer

<400> SEQUENCE: 7
gactgcgtac caattcaag                                               19

<210> SEQ ID NO 8

```
<211> LENGTH: 19
<212> TYPE: DNA
<213> ORGANISM: artificial
<220> FEATURE:
<223> OTHER INFORMATION: C116 reverse primer

<400> SEQUENCE: 8
gatgagtcct gagtaacca                                                   19

<210> SEQ ID NO 9
<211> LENGTH: 20
<212> TYPE: DNA
<213> ORGANISM: artificial
<220> FEATURE:
<223> OTHER INFORMATION: bnlg1953 forward primer

<400> SEQUENCE: 9
cctcggagct cgatttacac                                                  20

<210> SEQ ID NO 10
<211> LENGTH: 20
<212> TYPE: DNA
<213> ORGANISM: artificial
<220> FEATURE:
<223> OTHER INFORMATION: bnlg1953 reverse primer

<400> SEQUENCE: 10
aacatttaac cgccgtcatc                                                  20

<210> SEQ ID NO 11
<211> LENGTH: 19
<212> TYPE: DNA
<213> ORGANISM: artificial
<220> FEATURE:
<223> OTHER INFORMATION: LGI112958 forward primer

<400> SEQUENCE: 11
tcatcttcca cctcgttcg                                                   19

<210> SEQ ID NO 12
<211> LENGTH: 20
<212> TYPE: DNA
<213> ORGANISM: artificial
<220> FEATURE:
<223> OTHER INFORMATION: LGI112958 reverse primer

<400> SEQUENCE: 12
tgctcgctct gttatctccc                                                  20

<210> SEQ ID NO 13
<211> LENGTH: 18
<212> TYPE: DNA
<213> ORGANISM: artificial
<220> FEATURE:
<223> OTHER INFORMATION: PHI445613 forward primer

<400> SEQUENCE: 13
tgaccacaca cgagcgag                                                    18

<210> SEQ ID NO 14
<211> LENGTH: 21
<212> TYPE: DNA
<213> ORGANISM: artificial
<220> FEATURE:
<223> OTHER INFORMATION: PHI445613 reverse primer

<400> SEQUENCE: 14
```

```
gctcacaata tgtggcagag g                                              21

<210> SEQ ID NO 15
<211> LENGTH: 19
<212> TYPE: DNA
<213> ORGANISM: artificial
<220> FEATURE:
<223> OTHER INFORMATION: PHI364545 forward primer

<400> SEQUENCE: 15
taagcaaagc aaggcaacc                                                 19

<210> SEQ ID NO 16
<211> LENGTH: 20
<212> TYPE: DNA
<213> ORGANISM: artificial
<220> FEATURE:
<223> OTHER INFORMATION: PHI364545 reverse primer

<400> SEQUENCE: 16
tcgcctcact ctcacactcc                                                20

<210> SEQ ID NO 17
<211> LENGTH: 20
<212> TYPE: DNA
<213> ORGANISM: artificial
<220> FEATURE:
<223> OTHER INFORMATION: bnlg1732 forward primer

<400> SEQUENCE: 17 aactttggc attgcactgg                                                 20

<210> SEQ ID NO 18
<211> LENGTH: 20
<212> TYPE: DNA
<213> ORGANISM: artificial
<220> FEATURE:
<223> OTHER INFORMATION: bnlg1732 reverse primer

<400> SEQUENCE: 18
cgtaagtgca cacggcatta                                                20

<210> SEQ ID NO 19
<211> LENGTH: 24
<212> TYPE: DNA
<213> ORGANISM: artificial
<220> FEATURE:
<223> OTHER INFORMATION: umc1762 forward primer

<400> SEQUENCE: 19
cttactccag gcactccata ccat                                           24

<210> SEQ ID NO 20
<211> LENGTH: 24
<212> TYPE: DNA
<213> ORGANISM: artificial
<220> FEATURE:
<223> OTHER INFORMATION: umc1762 reverse primer

<400> SEQUENCE: 20
atccaggtga atggtgttta cgat                                           24

<210> SEQ ID NO 21
<211> LENGTH: 20
<212> TYPE: DNA
```

<213> ORGANISM: artificial
<220> FEATURE:
<223> OTHER INFORMATION: bnlg1007 forward primer

<400> SEQUENCE: 21
gatgcaataa aggttgccgt                                                    20

<210> SEQ ID NO 22
<211> LENGTH: 18
<212> TYPE: DNA
<213> ORGANISM: artificial
<220> FEATURE:
<223> OTHER INFORMATION: bnlg1007 reverse primer

<400> SEQUENCE: 22
atgtgctgtg cctgcctc                                                      18

<210> SEQ ID NO 23
<211> LENGTH: 20
<212> TYPE: DNA
<213> ORGANISM: artificial
<220> FEATURE:
<223> OTHER INFORMATION: bnlg1083 forward primer

<400> SEQUENCE: 23
acagtctgtt ggggaacagg                                                    20

<210> SEQ ID NO 24
<211> LENGTH: 20
<212> TYPE: DNA
<213> ORGANISM: artificial
<220> FEATURE:
<223> OTHER INFORMATION: bnlg1083 reverse primer

<400> SEQUENCE: 24
caacgctggt ttgtcgttta                                                    20

<210> SEQ ID NO 25
<211> LENGTH: 22
<212> TYPE: DNA
<213> ORGANISM: artificial
<220> FEATURE:
<223> OTHER INFORMATION: PHI256546 forward primer

<400> SEQUENCE: 25
cgtagtagtg ctcaagggga ga                                                 22

<210> SEQ ID NO 26
<211> LENGTH: 18
<212> TYPE: DNA
<213> ORGANISM: artificial
<220> FEATURE:
<223> OTHER INFORMATION: PHI256546 reverse primer

<400> SEQUENCE: 26
ccgagacgac gagaaacg                                                      18

<210> SEQ ID NO 27
<211> LENGTH: 20
<212> TYPE: DNA
<213> ORGANISM: artificial
<220> FEATURE:
<223> OTHER INFORMATION: bnlg1174 forward primer

<400> SEQUENCE: 27
cgcattccaa gaacaatgaa                                                    20

<210> SEQ ID NO 28
<211> LENGTH: 20
<212> TYPE: DNA
<213> ORGANISM: artificial
<220> FEATURE:
<223> OTHER INFORMATION: bnlg1174 reverse primer

<400> SEQUENCE: 28
ttcgattggt gggaagattc                                              20

<210> SEQ ID NO 29
<211> LENGTH: 24
<212> TYPE: DNA
<213> ORGANISM: artificial
<220> FEATURE:
<223> OTHER INFORMATION: umc1805 forward primer

<400> SEQUENCE: 29
agtgcaccag cttttaatca cctc                                         24

<210> SEQ ID NO 30
<211> LENGTH: 21
<212> TYPE: DNA
<213> ORGANISM: artificial
<220> FEATURE:
<223> OTHER INFORMATION: umc1805 reverse primer

<400> SEQUENCE: 30
tgtgacctgt gtggtctgtg g                                            21

<210> SEQ ID NO 31
<211> LENGTH: 24
<212> TYPE: DNA
<213> ORGANISM: artificial
<220> FEATURE:
<223> OTHER INFORMATION: umc1462 forward primer

<400> SEQUENCE: 31
gaacagcaag ccaacaaata atca                                         24

<210> SEQ ID NO 32
<211> LENGTH: 24
<212> TYPE: DNA
<213> ORGANISM: artificial
<220> FEATURE:
<223> OTHER INFORMATION: umc1462 reverse primer

<400> SEQUENCE: 32
gctgcattgc attacatgat agga                                         24

<210> SEQ ID NO 33
<211> LENGTH: 19
<212> TYPE: DNA
<213> ORGANISM: artificial
<220> FEATURE:
<223> OTHER INFORMATION: PHM8211 F ext primer

<400> SEQUENCE: 33
aggccaagga gctcgtcga                                               19

<210> SEQ ID NO 34
<211> LENGTH: 19
<212> TYPE: DNA
<213> ORGANISM: artificial
<220> FEATURE:

-continued

<223> OTHER INFORMATION: PHM8211 F int primer

<400> SEQUENCE: 34
agcctgtgtc ggtgaagac                                          19

<210> SEQ ID NO 35
<211> LENGTH: 19
<212> TYPE: DNA
<213> ORGANISM: artificial
<220> FEATURE:
<223> OTHER INFORMATION: PHM8211 R int primer

<400> SEQUENCE: 35
tccagccgag ccaacacaa                                          19

<210> SEQ ID NO 36
<211> LENGTH: 20
<212> TYPE: DNA
<213> ORGANISM: artificial
<220> FEATURE:
<223> OTHER INFORMATION: PHM8211 R ext primer

<400> SEQUENCE: 36
acacctaaac tactcggcga                                         20

<210> SEQ ID NO 37
<211> LENGTH: 19
<212> TYPE: DNA
<213> ORGANISM: artificial
<220> FEATURE:
<223> OTHER INFORMATION: PHM1934 F ext primer

<400> SEQUENCE: 37
ctgcagccca tgtgactgt                                          19

<210> SEQ ID NO 38
<211> LENGTH: 19
<212> TYPE: DNA
<213> ORGANISM: artificial
<220> FEATURE:
<223> OTHER INFORMATION: PHM1934 F int primer

<400> SEQUENCE: 38
caactctacg gcctctgtg                                          19

<210> SEQ ID NO 39
<211> LENGTH: 22
<212> TYPE: DNA
<213> ORGANISM: artificial
<220> FEATURE:
<223> OTHER INFORMATION: PHM1934 R int primer

<400> SEQUENCE: 39
gaaatgctct atgaatagac aa                                      22

<210> SEQ ID NO 40
<211> LENGTH: 22
<212> TYPE: DNA
<213> ORGANISM: artificial
<220> FEATURE:
<223> OTHER INFORMATION: PHM1934 R ext primer

<400> SEQUENCE: 40
tatcagatgc aatgcaagga ca                                      22

<210> SEQ ID NO 41
<211> LENGTH: 519
<212> TYPE: DNA
<213> ORGANISM: artificial
<220> FEATURE:
<223> OTHER INFORMATION: PHM6929 reference sequence

<400> SEQUENCE: 41

```
ttcattacgg gaggtccgag tcacgacatg ccagctttca tcaatctgtt ggccctttt      60 ccttgaggaa acctgttcct atcgggtcaa atcatcaggc tgaattacct gagtgcaggc     120
catttggtgg aagaactgaa gaagacgaaa gtgtcaagtg atcagaaac agtgttgtgc      180 caatgcctgg tactgatgca tcgtctttgg tgttggagcc tgttcactgc aaagcaggtt     240
gtgattgtct tgatgaaggt tcaatcaatt gtgtgaaaaa gcatgtgatg gaagcaagag     300
aaaatttgaa ggattctgtt ggtgcagacg ccttcaggga gttgggtttc tatgacatgg     360
gggaagaggt tgcctcaagg tggtcagaag aggaggaacg tttgttccag caagtggtct     420
cgtcaaaccg tgcttctctg cgcaggaact tttgggatga acttcctctt gccttccctt     480
ccaagtccag caaagagcta gggcacaact ttttataa                             519
```

<210> SEQ ID NO 42
<211> LENGTH: 732
<212> TYPE: DNA
<213> ORGANISM: artificial
<220> FEATURE:
<223> OTHER INFORMATION: PHM8711 reference sequence

<400> SEQUENCE: 42

```
taacgccaat ggtaatggtg gttttcggct cgattattga cggcccaatt tgaacaagat     60
cgaaggttta gattttcgtt agatctgatt acggccagac tattcttact tgatttaact    120
tctataggtt gccttgtatc gattactgaa ttagcctgtg aaccaatgtt acggtaccca    180
agtttatcca cttgagttag agtaatctgt tagaacatgc aataccggat cgagtttttt    240
tggttgtttc tgttagatga gcaccacttg aagtgttgaa tagctttgtt tgtacaattt    300
ggcaatgttc ccataggttg ttcattggat ttacaatata ttctagatgt aactacaaac    360
ttccatatct gctaacataa acatgaagtg gcatgtgcca cctgttagtt tttgcaatca    420
tattttgtct taccttcatg atcacttgtt gttcacctgt ttgtagatct taggagatgg    480
ggatgtatca gttaagttga atatcaaggc tggagcgttt tcagcttcag ctaaagagaa    540
gcttgaggca gctggttgtt ccctaactct gttacctaaa cgaaagaaat ggcttccaca    600
aaattatcta agaaccaag cccgagcaga agagtacttt gccaagaaaa aagctggtgc     660
tggtgaatct gatagcggct ctgcatagat tttaattggg tataagcctt cctggccawt    720 aagaattta aa                                                          732
```

<210> SEQ ID NO 43
<211> LENGTH: 815
<212> TYPE: DNA
<213> ORGANISM: artificial
<220> FEATURE:
<223> OTHER INFORMATION: PHM8211 reference sequence

<400> SEQUENCE: 43

```
ggggccaatc ccagtcacga ggagcctgtg tcggtgaaga ccacgcctca ctcagttgaa      60
gtgaaaccgc aggtgaagcc tcgatcctcc atctccccat cttctttgca ttgggcaaat    120
agaccaggcg acgagattgt tcgcttttgc agggcgtgag caagggcttg gtggctcggc    180
```

```
gcatgcttgt gtcgatgaag gagcggggcc agtgcccgga cttcgtcctg tgcatcggcg      240
acgacaagtc cgacgaggac atgttccagc tgatcgccac cgctgcctgc ggggactcgc      300
tggcgtccaa ggcggaggtg ttcgcgtgca ccgtcggccg caagcccagc aaggccaagt      360
actacctcga cgacgcggcg gaggtggtga ggctgatgca ggggctctcc tacgtctccg      420
aggagctggc gctggcgaac cagcgggatg aagacgagga ctcctctttg gacgacgtgt      480
gggaatagga aggagcgttc ccttcccgtg ctgctcctgc ggtaatgtct gtttgtgttg      540
ctcgttaatt gcttattact gtgtctaggg gggtgaatgt aaaaaaactc aagacacgta      600
tcttaacgaa gacacagtgt cttagctcta tgtttgagac aggagactag ctgattggtc      660
actttaattt attgaatgct ctgattggta caatgaatat cgtaagacac atgttttaga      720
catgaccact gtattatgtc gtgttttagt tgtatcttgt acttggagta ccgtgcagca      780
gtatcaggtt gtacatgccc taatgtctgt ttgtg                                 815

<210> SEQ ID NO 44
<211> LENGTH: 548
<212> TYPE: DNA
<213> ORGANISM: artificial
<220> FEATURE:
<223> OTHER INFORMATION: PHM14506 reference sequence

<400> SEQUENCE: 44
cagcacacac acttcctggt ggacgtaatc ttcgcgctct acgacgagga cctcaagggg       60
ggcccggagt ccgagcgctc cttcgggctg tacaagactg acctgacggc gaactacgac      120
gtcgggctcg caaaagacaa cggcacggcg gccccgacca gcttgactcc ggttccggca      180
caggtgcttc cagttcccag atcagtgctc gtcacctctg ctgctgccct tgattgaggg      240
aacgcggcgt tactgatgcc atatgaattt gcagggcacg ccgcagccga gcaaagggac      300
gatgccgacg gggtactgcg agaccacgtc cgccgtgccc ggcaccacgc aaggccaaca      360
gttgccgcag agcagctcgt gctacattcc cggcggagct gagtcgcggc acgccacatg      420
gcagcttgtt ttattgggtg ttttgctgtg cttggtcaag gtagccggca tctagttaca      480
acatctgtgt gcgacggaac gagtacaggg ttcgctctcc acagttgtat ggtcatagct      540
gcctaccc                                                              548

<210> SEQ ID NO 45
<211> LENGTH: 670
<212> TYPE: DNA
<213> ORGANISM: artificial
<220> FEATURE:
<223> OTHER INFORMATION: PHM1754 reference sequence

<400> SEQUENCE: 45
ctcaagtttg ttgtttcgaa aggataatgt cattgtttgg aactagcagg tttcagttgt       60
gtccttctga cactacttga agcgaaacca ttatcgtttg taaagtatct taaccttttc      120
tgttccttca gactgcagtg atcctgcagt gcttaatcta gaacggtaaa gtaggagtaa      180
tgtgtcattg ttctgttatg attgtagtaa ttagcatggg ttttgcagat gattgggtag      240
ttgtttcaga aacagagcag tgctggaatc tagcaatcgg gcaagaatca tacccatgct      300
tatctcatat gatctatgca ctcgcaggtt gacattgagc ttccagagga cttgccactt      360
aaggaggcac acgccattgg agaatctctc caaatcaaga ttgaggagct acctgaagtt      420
gagcgagcat tcgttcacct agatttcgaa tgtgaccata agccggagca ttcaattctc      480
aacaagcttc ccagcagcca gccttgatcc gaacgaatcc tgtgtggtag attgtcgtgc      540
```
agaatctgct gcagttcttg cattggcgtc ttgtgctgta tgacaaaact aagagttcaa    600
ttagttttgt ggcggtgagt ttaagatcag gcgcatctaa gactacgaga gatgaagtgc    660
cgaagcgggt                                                           670

<210> SEQ ID NO 46
<211> LENGTH: 614
<212> TYPE: DNA
<213> ORGANISM: artificial
<220> FEATURE:
<223> OTHER INFORMATION: PHM3951 reference sequence

<400> SEQUENCE: 46
grmcaagtga gtagtctggc aggatagaga gttgttttcg ggtcaaacct agtcctagaa     60
agacaagcag cttcaatagg aggaccagca accaccatcc aaacgcaaat ggcgctggat    120
tcatgactcc ggtgccacgc cgagtttcag ctggcagtgc caccccagag cttctgaccc    180
cacgctcgta ttctggccgg tacaacaact acttcaagga gaacaggcgc ctgacagctg    240
caccactgaa cttctcagtt ggttccaagg aggatagcat gtcatccttc gcatccatca    300
gtggctcgga acctgattcg ccattgtttt tgcactaagt gtgagatttt caggatttca    360
ttgcggtggt ttccaagatt tgtccttgaa gctgtgctga tcctggtttt taaccgtggc    420
tgtttcaggt tggttaggga ggagacttct tggtgaaaat ggtggatagc ctcaagatcg    480
gaccattgtg tgtgtgtgtg tgtgcatctg ttaacattgc tgattggtaa caacaggttt    540
tcacaagttt agatgcgatt gcttgtagat ataatatcta acattcatgg ttccgctgta    600
cccccaaatt gtca                                                      614

<210> SEQ ID NO 47
<211> LENGTH: 518
<212> TYPE: DNA
<213> ORGANISM: artificial
<220> FEATURE:
<223> OTHER INFORMATION: PHM1934 reference sequence

<400> SEQUENCE: 47
aataaaaaaa ggggaaggtc ccagtcacaa agcaacttta cggcctctgt ggagcctgcc     60
ctggctggga ctgccgataa agatggcagc aggagtcaag gcgcagtggg ccagtaacgg    120
taaagtcgtg cggtcgggac tgcgccatta aggtgggtc ctgcacgctc gctctgcaga    180
attgattaac cgggcgtgct gtaacagtat gggcttatcc gagtatagtg actactggta    240
gtgacagtgt tgtgtgaaaa actgaactct ggtgtttcta cttgcttgac tgtgtatgga    300
ggcaacagta cttgcttgcc actggcggac aggacacagg agcaacggaa agaaatggag    360
caacaggaca aagctatgaa aaacgagtac tgctagcttt ggtatttcta tgtggattat    420
ctgaattgtt ttatcgtcca cttgcattct ctcccgcata gtcgaagttt gtctatcatg    480
gcttattgtc atctagatca atttcctatt taaaatag                            518

<210> SEQ ID NO 48
<211> LENGTH: 637
<212> TYPE: DNA
<213> ORGANISM: artificial
<220> FEATURE:
<223> OTHER INFORMATION: PHM4423 reference sequence

<400> SEQUENCE: 48
ccaagtcaga cgatctgatg attgcagaca actcatttca cgtatctttg tcagcaatcc     60

| | |
|---|---|
| attaagggta atacaatgaa ccatctcaat tgtgatgtca ctgtgtctgc atggttattg | 120 |
| ggtctataag tggcttatct tttttttgcaa ttttgaattt cgcatagaga atcaccatga | 180 |
| gggaaataaa aagccatcca tggttcctaa agaacttgcc gagggagctc acagaggcgg | 240 |
| tgcagttatc ctacttcagg agggacaaca gtgtctctgc attttcagac caaacaaccg | 300 |
| aagaaatcat gaagattgtc aaggaggcaa gaaccttgcc aaaatcgtcg agatcaggct | 360 |
| atggctacag tgaagaatgc tcagatgagg aggaaaagga agtggagagc gaacccaaag | 420 |
| aggaggaaga agaagctgag tgtgataaga cagttaggga ggttcgcgag agcggggagc | 480 |
| tggatatgac ctcactgcac atctaaatgc tgcctgtgag gctgtgacgt gtctgtagat | 540 |
| aattggcttt attgtctgct gaatttggta gaacgtatgc aattctggcg tcagatatag | 600 |
| tgtctatata gccttcctcc taacccttat tttatta | 637 |

<210> SEQ ID NO 49
<211> LENGTH: 711
<212> TYPE: DNA
<213> ORGANISM: artificial
<220> FEATURE:
<223> OTHER INFORMATION: PHM9362 reference sequence

<400> SEQUENCE: 49

| | |
|---|---|
| cctttaaata aagtccccag gggtccccag gtgaaatggc tttcaacagt tctgttgatg | 60 |
| tgaagtctta aacgtcccta aatacccttg tcaatgacat gtttccacca acgactctgg | 120 |
| ttgagcaggt cagtttaatt catatctgct gaatagagtg gtattttgct tgtcttaggc | 180 |
| atcgactgga attatgtcct aatggaacaa tcgcatcggt tggatctgga agactttaat | 240 |
| ggctcctaac attccatcat ttcgtttttt agctacattt tgtctccaat acccatgatt | 300 |
| tgctagctac ataatatttt taattttttct aataattaga taataacttc atagtacatg | 360 |
| aatactgcaa tcagtccccg atccttgtgg catctatgtc aaacactcaa ctactcaaaa | 420 |
| catacattgg acaaatgcat gctcatataa tttccttgtg ctgaatgttg tgcaggaaga | 480 |
| ctacaacaac tggaattact ggaaggtgcc attaccagat gttgatttgt agtgtagttt | 540 |
| tgacagaaac agccgtagat accagtagat cctgcaaaag cctagcagta gagcttcctg | 600 |
| taccctaatt ttcagccacc acgacggttt taggtccaat ttgtgaaggt ctcaagaatt | 660 |
| cccggatgta tgttttctga agccaatgcc cagggaaaa ttggctaatt a | 711 |

<210> SEQ ID NO 50
<211> LENGTH: 703
<212> TYPE: DNA
<213> ORGANISM: artificial
<220> FEATURE:
<223> OTHER INFORMATION: PHM1147 reference sequence

<400> SEQUENCE: 50

| | |
|---|---|
| ccccccccta aggggaattt ggcggctccc ccggtaaagg aattgactga gatggaagag | 60 |
| agagaacaga gagaaatgga gatgaaacag caagctgatc atgatgcagg tgcaaccggt | 120 |
| ggcactgtgg atgggcatgg aaggtgattt atatatttta taactttgtc catataccct | 180 |
| cttgtttcaa ctttttaaag aactaggtag ctcatttcca gtatgttttcc tggcccatct | 240 |
| gtgccttttg ttccttaccc attcatgtat ctgaaaaata tctctactct tcacagctct | 300 |
| ggcaatgatc caatggatgt ggatgtagga tcaaatgatc agaatgtttc cgcagagagg | 360 |
| tcactacata acctgcaaat cttaacattc agcattgttg tgtttacgcc tgacccttg | 420 |
| ctgcccttgt ttttgcaaaa cctgcagaat tgaagcattt gaagcacttc tgggtcagca | 480 |

```
tgtgttggca aaccatatag atcaaatgtc aattgatgat atcgagcaga tggttaatag    540
ggagtcaact gcaccttaca ccagaagcca agtagagttt atttggagg tatgaaaaaa      600 acaatctact tttatttcag gcctttaaca tatagctaac catttcgatt gcattaacat    660
tctatttcct tgkgccctca aaggatccaa atccaaaca ggg                        703

<210> SEQ ID NO 51
<211> LENGTH: 473
<212> TYPE: DNA
<213> ORGANISM: artificial
<220> FEATURE:
<223> OTHER INFORMATION: PHM11850 reference sequence

<400> SEQUENCE: 51
cggccgctcc ccccgttttc tgctgggagt ttgatcagca ctccatgagt gctcatacga    60
gagctcgctt tcatgggtgg agaggtttga cataatcgtt ggcgtggccc gcgcacttgt   120
gcacttgcat cgctacggta taatccacta caatctgaag tccagcaatg tcttgctaga   180
cacgaatggt gagcccaggg ttggtgatta tggtcttgtg aacctgctgc cgatgctgga   240
tcgctatgtg ctcagcagta agatccagag cgtgctggga tacatggcac ctgagttcac   300
ttgcacaacg gtcaaggtca cggagaagtg cgacatatac agcttcggag tgctagtcct   360
tgagattttg tcaggcagaa ggcccgtaga atatctggaa gatagtgtgg ctgtgctttc   420
tgatctgtca atggtcatag cggtcccttc ccaggatgga tcgatccaac cgg          473

<210> SEQ ID NO 52
<211> LENGTH: 646
<212> TYPE: DNA
<213> ORGANISM: artificial
<220> FEATURE:
<223> OTHER INFORMATION: PHM9301 reference sequence

<400> SEQUENCE: 52
cccccttggg ttttcttaaa tgccagctaa atcgggtttc atctttcagg ggcttttaag    60
ggcaaatcat ttagctaaaa ccgtcgttgg tcgcctgatc acatagctca tgatgcatgt   120
ttcgttctga aatggatttt gttcagttcg aaaaattggt caattgtttt ggatggagtt   180
cactgtagtc tattcacttt ggtgtgatgt acataaaatg gcacatgcag catggtgctc   240
actactttga ttttttttta aaaaaaaact tacaaacata gtgcctagta tatcgccgga   300
acttgttttt aaaaattgcg tttgaagata aacagttgag catggaactg catttctcgt   360
gccggtgcct tagaaattta tcgaacgcta acacctcttt cctgtaacgc agctggctct   420
ataaacataa gcagcatact gtccgggaaa tgcctggcaa aaataaacac tggaaactcc   480
aatgcttgca aggaaagaaa gaaggcgtgg aagttccgga acacagtctc ggaggccctt   540
gaggacatca cggctctgta ctacgacgag gatcgcgacg agatctacac tgcaaccggc   600
acggccttgt ccatgtgtgt cgagctaatg ctaactttcc aaaaac                  646

<210> SEQ ID NO 53
<211> LENGTH: 707
<212> TYPE: DNA
<213> ORGANISM: artificial
<220> FEATURE:
<223> OTHER INFORMATION: PHM5280 reference sequence

<400> SEQUENCE: 53
attgtaggat cacaattgga ttcttgaagt atagcttgca gtcttgcact aatgcacttt    60
```

```
accactgttt ttaagtaaat tgctgttcat gttttcagat acaataaagg gtggttttac    120
cacaaagact accgtgtctg ctaacaaga gctcctaatt ccgcacctct tgtgaaaact    180
ccacttcatg aacgagggtc ctacatttgt tttgatccaa gcatctggga tactgttcat    240
aaggtttcgt tatctgaatc aaaccataca taatcattat ctactagcag agatgtgtat    300
ctgagcattc ttttactttc aggacaactt tgttctccat tacgaagcag tggagaagag    360
acctgtcctt ccttctgctg gccaaaatat taggcgagaa ctataaggta gcatgcttct    420
atcatatata aaggaatgt atagttatgt gtacgtttga ctaattgact tccttccctg     480
atgcacacat atttgccctt gctgcttgcc ctaggttctc ctgcatttga agttagtttg    540
gtttgatcag tagctgttgt catggatggg atgagttcat acaaaatgat tctataagaa    600
cttatgaccc ccaggtggca gtttgtagaa atgtagctga gatttagatt ttcttcataa    660
tttgttgcat tattagtagg cgtttagtag gccatggtga ccagaga                 707

<210> SEQ ID NO 54
<211> LENGTH: 438
<212> TYPE: DNA
<213> ORGANISM: artificial
<220> FEATURE:
<223> OTHER INFORMATION: PHM13773 reference sequence

<400> SEQUENCE: 54
ggggcggttc ccagtcacga cgagagcttt agcaacgaac agcaagccca acaaaagaac     60
ccagacgcag tgacaaacag tgttccgagc caaggccagg agcccttgaa cacgtttcca    120
gattcagacg atggaaacac gaacaccggt ccgttgaatg ccacgcagc agctcatgtg     180 aacatggaag ctgccatctc cacggaggac gtcatacggg ctggcgggtt cggagcgaag    240
gacgacatcg gcagcctcct cccgacggca attgattcca ccgattttga ggcctcgctg    300
cgggatgccc gtggtttcga gggcgagaaa gcggcgccgt cgcatcctgg actagggtgg    360
aagggggaga agctgatgg tgaaccaaac tggcagatgt ggcgagcagt atcacgcaag    420
gtaagggaaa cttaaggg                                                  438

<210> SEQ ID NO 55
<211> LENGTH: 585
<212> TYPE: DNA
<213> ORGANISM: artificial
<220> FEATURE:
<223> OTHER INFORMATION: PHM16422 reference sequence

<400> SEQUENCE: 55
acgtgagaat gatgctgcgt tgggtaagtc tcgagaccca tttttttaaaa taatgtctga     60 tttcaagaga ttgatgcatt tatcccttat agactttaag aacgtatcaa ttgtgggaca    120
ctatgtgaaa gataggacca agatgcgca attcatcatt ataaggtatt actatcagct     180
cagattcaat aatatttct ttgcctatac ttcacaccat ctctagaaag gtgtggtact     240
agtacaaaga agcatccata tctgagatgg ccatgggcca tggctcatgt aaactcacgt    300
gttattttac agtctgagga acaacatgtt tgaactagcc gacaggttgg ttggtattta    360
caagacggac aattgcacca agagcataac gataaaccca ggaagctttg ccgagagcat    420
gaaagtagtg tagcgtgctc accatggatc cttccgctaa atgtaacctc cctagtgtcc    480
taagcgaaac taaccactct ggtgtccttc agctaaatgt aaccgttgta gtgtcctcgt    540
gaaccgagtt cctcggcatt tgttgccgga ggaaggtaaa aaaaa                    585
```

```
<210> SEQ ID NO 56
<211> LENGTH: 481
<212> TYPE: DNA
<213> ORGANISM: artificial
<220> FEATURE:
<223> OTHER INFORMATION: PHM9009 reference sequence

<400> SEQUENCE: 56
tagtggcccc ccatttgggt ggttcccgga taaatgcagg ctatggaagt ggtggtgcaa      60
ctctggctat tcaagtgctt ggagtgatcc ttcgcaaggt ggtggatttg gcggttcggt     120
caatggaggt gctgaaggac agtcaactta tggcactggc tatggcagtg tgcagcccag     180
ggttgctcag taaagagagg cattttgagt gtgcgaaatg aaccagtgca tctgggcagt     240
ctatgtattg atttgtcatt ccagtctctc tggttgctct cagcattttg aagattgccc     300
atttgctgct taaatcagta tttatccggg ttggaatgct tgatccttta gcggcttact     360
actagaacgt ctagtcaata agtagctaaa atgtggagta gcagtatctt gcggaatgct     420
tttattaatt tttacattta gctttatcca tcatggtcat agctgtcctt ccccctcaggg    480
g                                                                    481

<210> SEQ ID NO 57
<211> LENGTH: 662
<212> TYPE: DNA
<213> ORGANISM: artificial
<220> FEATURE:
<223> OTHER INFORMATION: PHM3171 reference sequence

<400> SEQUENCE: 57
ggggttttga acaggaagcc atggatataa ataaaaggtg ttttcaggcg aatggatcca      60
tctctgtaac ccatgccaaa gatgctttcc tcccttgggc ttttttaaca acaaacgtgt     120
tgttttaccc cctcgacagg aacaaggtct tcagatgttt ctggcaagcg gatgcgggag     180
gtcgcatgcc caacctgcac ggtccatctt caggtgtcta ttttttttcc gcaacaatat     240
acgcctcttc cgaattccga tgcctagtgg cccggttgac aatctgacac atctggacat     300
ggcacaacga atttgctttg atccaggtcg aggttccagc ttctggttcg agacgatag      360
agtgcggcgt atgtcagaac cctttcctcg tcagcgcccg ttgaaccgag ttcagcggct     420
tcaggcgccg tgcggcggag tcttctcgga ttcgcaagcg aagagtcggt cctgttcaat     480
cgagcctggc gcttgaattc cggctatccc tgtctgtctg taccctaatt ctgcacggaa     540
gtctgtcact gcaagttgtt agtaagttat atggatgagt aatgagttga gtcgtttgca     600
agttgttagt acagttgtga gttgctttga gaagcaagct ggtcatgttt aatttktttt     660
tt                                                                   662

<210> SEQ ID NO 58
<211> LENGTH: 664
<212> TYPE: DNA
<213> ORGANISM: artificial
<220> FEATURE:
<223> OTHER INFORMATION: PHM3860 reference sequence

<400> SEQUENCE: 58
aagtactgca gtttgaccat gtttatgatg ctttaacat tctctgtagg ttatgtattg       60
gagaagagtc gcggacagaa ttcagatgct gaagtcagca attttacatc ccgagctgaa     120
ttccagagca taacctactg gaatcacgat acagcgccat cagcagagga ttccctcccg     180
aggtgcttcc attggctaac cgtcgctaat gcggtgagca ttatttcttc acctaacgat     240
```

```
ctgtttgttt tccaattacg caaatttgtt ttgcttccgc cgcatcaact tgttgtggtt    300
agctatatgc agtaggccac ataaatcaat aatcactgaa acaaaggaag tgtcatcaca    360
tagactgaca gacatgatcc taatttcggc ttcctgtttg tacagatgca tagagcagtg    420
actgctgaag acctggctaa catggcagca atgcagaatc agggcaagta gattcgttct    480
ataacgtagc cgtgcaattt cgatttggtg aaccatctcg acaagggatc ttcctgtaac    540
aagcaacatg ttatttgaac gcatccagta ggtaatgttt aggctttggg gtaagatgct    600
tcaggagatc cttgttcagt agcatctgaa aatgtctggt aattagttgt agaatgttta    660
tgta                                                                 664
```

<210> SEQ ID NO 59
<211> LENGTH: 731
<212> TYPE: DNA
<213> ORGANISM: artificial
<220> FEATURE:
<223> OTHER INFORMATION: PHM7942 reference sequence

<400> SEQUENCE: 59

```
actgatgagc kgggatccca gcagaaaagc ccccattgac caattcaccc ctttgggccg     60
aatgctttac aaggcaccat ctgatgggaa atgggggggg catgagcgta agtttctacc    120
acctatctcc tcatctactt gcatccagat agtttgactt gccaattggt cgatggtatg    180
gaatagactg ttgacacact agtatagaat cctccacaca gattcactg aacattgttg     240 ctggaagatg tttcgctgag acttccgact gttaatgcta gttgctcttt cgtctttcct    300
taccatcagt tgactacctg ctgttcatcg tccgggacgt gaaggtgcag ccgaacccag    360
atgaagtcgc tgacgtgaag tacgtgaacc gcgaggagct caaggagctc atccggaagg    420
ctgacgctgg cgaggatggg gtgaagatct ccccctggtt caggctggtg gtggacaact    480
tcctcatggg ctggtgggac catgtcgaga aaggcaccct cggcgaggcc gtggacatgg    540
agaccatcca taagctgaag gagtgagggg acgccggccg ccgtctccg atgacctcac      600 cgcctgttga tgttgctgct gctgctgcac tgcatgttta tcaaaagtta tcgctcctgc    660
tcgcggaaag tgagcttgac tgttgccggg gtggaagtat cgttttgact atgcatgaaa    720
ctgggtaata a                                                         731
```

<210> SEQ ID NO 60
<211> LENGTH: 465
<212> TYPE: DNA
<213> ORGANISM: artificial
<220> FEATURE:
<223> OTHER INFORMATION: PHM678 reference sequence

<400> SEQUENCE: 60

```
tttcatcccg tcaggaggtc cggcggcgaa ctcaccggcg ccgcgtcgga ggccgccgtg     60
gacagccggt gatcagcgtc aacatcgagc aggaggtgaa ggtggacggg aaccagatca    120
tggacatgta catgaagagc atgcagcaat tcacggattc cctggctaaa atgaagctcc    180
ctgccttgga cttggacata gacaatggta gcagcgggag gagtagtcct gcagcagcca    240
caaccgacgc agactccact ggtgccgact cgatcgcgt gaagaagcca gccgccgccg     300
ggaagcagga taagccatct cccaaggtgt tctatggcag ccgggcgttc ttctgatctc    360
ctgtccgctt gagcactgga agcacagcgc tccagccgcc gagtaacgaa gcaaagagac    420
ggcatttgca gtcgcctcag ctgaatctta atggtttatag ctggt                   465
```

<210> SEQ ID NO 61
<211> LENGTH: 564
<212> TYPE: DNA
<213> ORGANISM: artificial
<220> FEATURE:
<223> OTHER INFORMATION: PHM8358 reference sequence

<400> SEQUENCE: 61

```
gcgccccccc aaactcccga ggtcttagct tcggctacaa gcccgtcgtc tcctatggat        60
ccatcagtaa ctctctttct ctttctcttc tctctctccg tgatcgatcg tatcacgcga       120
ctctatcaac gcgaccacgc ctgatgatgt tggttctctt cgtgtcgtgc gtgcagatga       180
cacggccatg ttctacgggc tcaagtactt caacgaccac ctgatgcagg cggggccgta       240
cgggaacgtg cagtcggagg tgctcatgcg caaggacgcc agcaccttca ccttcaggca       300
gggctgggcc ttcccgcgca aggtctactt caacggcgac gagtgccaga tgccgccgcc       360
ggacgcctac ccctacttgc ccaactccgc gccgccgaca gccgcggcgt cgctgggcgc       420
cgcagcggca gcggccgtcg tggtgctctt gggcatgatc gtggcatgag aaaacacggg       480
acatcgatcg acctatagtg ctagaatcgg cacaggggaa tggaaaaaag acgttgcttt       540
cttctgtaga tggttatggc tgtg                                              564
```

<210> SEQ ID NO 62
<211> LENGTH: 587
<212> TYPE: DNA
<213> ORGANISM: artificial
<220> FEATURE:
<223> OTHER INFORMATION: PHM16415 reference sequence

<400> SEQUENCE: 62

```
cccacgacac accattcctt tgggagctc attaggaagg agggactcaa ggacagcaaa         60
catgaagcta gcaaacaaga accttcctcc accaaacgca acactgcacc gtctcatcaa       120
gttcttccga aggcaagggc tggacaaggt ggaccttgtg gcactatcag gaagccacac       180
cattggaagt gccagatgcg tgagtttcaa gcaacggctc tacaaccagc acagagataa       240
caggccggac agcacgctag agacgagttt ctaccacacg ttggcgtcgg cgtgcccacg       300
cgccggtggc gacggcgaga tacggccact ggatctcgtc agcccttcgc gatttgacaa       360
cagctattat aagctggtac tggaggggaa agggcttctc aattcggacg aggttctgtg       420
gacaggaaga gaccccgaaa ttgcaggcct agtcaagagt tatgccgaaa acgaggcgct       480
gttctttgag cactacgtga gttcagtaac caaaatgggg aacataaatc ccctcacggg       540
tcacgaygga gaaatccgca agaactgcca tggtcatagc tgtttttt                    587
```

<210> SEQ ID NO 63
<211> LENGTH: 695
<212> TYPE: DNA
<213> ORGANISM: artificial
<220> FEATURE:
<223> OTHER INFORMATION: PHM737 reference sequence

<400> SEQUENCE: 63

```
aggggttatt gaaagttagt attttcttag gggttaactt ggacaaacct gatcttttgt        60
tcttaaaggg ttttggtcaa ttttcactgt tatattaaaa caaacgcaaa gtagaacagt       120
tggaattggc tagcaagatc tgtgacagta tatgaactta ggaactaaca aaaccatatt       180
caagcagtgt cgcgcttggt agttttgttt gatctacggc caagagcatc attttttttc       240
cttttgaaat gaaactgaga attctcatgc catataaaga tgagtgaata ttgtgtaggt       300
```

```
tggaatctcc tctggagcag ccgccgccgc tgccataaag gttgccaaaa gaccagagaa    360
tgctggaaag ctgatagtgg tacgtgcaga aatgccatct ctgctataac ccttttgcgg    420
ataccgttac attacatgaa gtgtggatgt tgagtgcacc tagattatta acttatatta    480
tcatattgtt tctgttcagg ttgtgttttcc gagcttcggc gagaggtacc tttcatctgt    540
cctctatcag tccataagag aagaatgtga gaacatgcaa cctgagccat gagggagccg    600
tcactttaag cgggcatagt aaatgttttct gaaataagac gcgtagccag catcagttgc    660
tccacttgaa tcattgccag gaaaaaaaaa tgaya                                695
```

<210> SEQ ID NO 64
<211> LENGTH: 744
<212> TYPE: DNA
<213> ORGANISM: artificial
<220> FEATURE:
<223> OTHER INFORMATION: PHM9092 reference sequence

<400> SEQUENCE: 64

```
ggggccaatt caaaaaaagg ctttatgtgg ggggaacata ttgcaattgg caacgcaatc     60
aatgtactat attgaatctt cattacttca aaacctttct gtttgttatc gtttccatca    120
ctaagttttt ctcatgggaa aattatcgcc agtaaaactt gccctgggcc ctggttagag    180
tcaatctcgc atggaatatg aactcccagt ctcatgatga cagttctgcc atgatatagt    240
tatttcagta tctggttatt ccctatagtt tatagttatt tcagtgtctg ttattccct    300 atagtttgtt gctgccgtca agaaatgact taggatctgt gtcgcccaac aatttgggta    360
actctgcagt ctatatgatc caccgagatt aacacttgtt atctatgaat gttaaaatcg    420
cgtctcactt cgttgcccta gtttgagctg atgctcgtcg cacatcgttt cgttacattg    480
ctggctggct cacaatggta actgaaaacc catcttaatt tctgttgttt gtttaggtgg    540
gtatttcgat tcagttatat gagctaaatt gtaaaagat ttagccactt taccaattac    600
catctgattt gtctactcac ccattgttga tctggttctc tttgcagtat atctggagtc    660
aaagcgaggc cgcgtttttct gcatagtatc tgagaccccca gcattatgac gagccgagca    720
ttggaaagag ggtaaaactw cyta                                            744
```

<210> SEQ ID NO 65
<211> LENGTH: 25
<212> TYPE: DNA
<213> ORGANISM: artificial
<220> FEATURE:
<223> OTHER INFORMATION: PHM6929-3-U forward primer

<400> SEQUENCE: 65

```
tctttggtgt tggagcctgt tcact                                            25
```

<210> SEQ ID NO 66
<211> LENGTH: 34
<212> TYPE: DNA
<213> ORGANISM: artificial
<220> FEATURE:
<223> OTHER INFORMATION: PHM6929-3-U reverse primer

<400> SEQUENCE: 66

```
aaattttctc ttgcttccat cacatgcttt ttca                                  34
```

<210> SEQ ID NO 67
<211> LENGTH: 29
<212> TYPE: DNA
<213> ORGANISM: artificial

```
<220> FEATURE:
<223> OTHER INFORMATION: PHM6929-3-U probe 1

<400> SEQUENCE: 67
cgcgccgagg atcaagacaa tcacaacct                                    29

<210> SEQ ID NO 68
<211> LENGTH: 31
<212> TYPE: DNA
<213> ORGANISM: artificial
<220> FEATURE:
<223> OTHER INFORMATION: PHM6929-3-U probe 2

<400> SEQUENCE: 68
acggacgcgg aggtcaagac aatcacaacc t                                 31

<210> SEQ ID NO 69
<211> LENGTH: 34
<212> TYPE: DNA
<213> ORGANISM: artificial
<220> FEATURE:
<223> OTHER INFORMATION: PHM8711-14-U forward primer

<400> SEQUENCE: 69
gcaatgttcc crtaggttgt tcattggatt taca                              34

<210> SEQ ID NO 70
<211> LENGTH: 29
<212> TYPE: DNA
<213> ORGANISM: artificial
<220> FEATURE:
<223> OTHER INFORMATION: PHM8711-14-U reverse primer

<400> SEQUENCE: 70
acaggtgaac aacaagtgat catgaaggt                                    29

<210> SEQ ID NO 71
<211> LENGTH: 31
<212> TYPE: DNA
<213> ORGANISM: artificial
<220> FEATURE:
<223> OTHER INFORMATION: PHM8711-14-U probe 1

<400> SEQUENCE: 71
cgcgccgagg agcagatatg gaagtttgta g                                 31

<210> SEQ ID NO 72
<211> LENGTH: 31
<212> TYPE: DNA
<213> ORGANISM: artificial
<220> FEATURE:
<223> OTHER INFORMATION: PHM8711-14-U probe 2

<400> SEQUENCE: 72
acggacgcgg agggcagata tggaagtttg t                                 31

<210> SEQ ID NO 73
<211> LENGTH: 21
<212> TYPE: DNA
<213> ORGANISM: artificial
<220> FEATURE:
<223> OTHER INFORMATION: PHM8211-16-I forward primer

<400> SEQUENCE: 73
gcccagcaag gccaagtact a                                            21
```

<210> SEQ ID NO 74
<211> LENGTH: 16
<212> TYPE: DNA
<213> ORGANISM: artificial
<220> FEATURE:
<223> OTHER INFORMATION: PHM8211-16-I reverse primer

<400> SEQUENCE: 74
ccgctggttc gccagc                                              16

<210> SEQ ID NO 75
<211> LENGTH: 23
<212> TYPE: DNA
<213> ORGANISM: artificial
<220> FEATURE:
<223> OTHER INFORMATION: PHM8211-16-I probe 1

<400> SEQUENCE: 75
cgcgccgagg aaccacctcc gcc                                      23

<210> SEQ ID NO 76
<211> LENGTH: 25
<212> TYPE: DNA
<213> ORGANISM: artificial
<220> FEATURE:
<223> OTHER INFORMATION: PHM8211-16-I probe 2

<400> SEQUENCE: 76
acggacgcgg agcaccacct ccgcc                                    25

<210> SEQ ID NO 77
<211> LENGTH: 19
<212> TYPE: DNA
<213> ORGANISM: artificial
<220> FEATURE:
<223> OTHER INFORMATION: PHM14506-7-U forward primer

<400> SEQUENCE: 77
cggcgaacta cgacgtcgg                                           19

<210> SEQ ID NO 78
<211> LENGTH: 23
<212> TYPE: DNA
<213> ORGANISM: artificial
<220> FEATURE:
<223> OTHER INFORMATION: PHM14506-7-U reverse primer

<400> SEQUENCE: 78
cggaaccgga gtcaarctgg tcg                                      23

<210> SEQ ID NO 79
<211> LENGTH: 21
<212> TYPE: DNA
<213> ORGANISM: artificial
<220> FEATURE:
<223> OTHER INFORMATION: PHM14506-7-U probe 1

<400> SEQUENCE: 79
cgcgccgagg cggcacggcg g                                        21

<210> SEQ ID NO 80
<211> LENGTH: 23
<212> TYPE: DNA
<213> ORGANISM: artificial
<220> FEATURE:
<223> OTHER INFORMATION: PHM14506-7-U probe 2

```
<400> SEQUENCE: 80
acggacgcgg agtggcacgg cgg                                           23

<210> SEQ ID NO 81
<211> LENGTH: 26
<212> TYPE: DNA
<213> ORGANISM: artificial
<220> FEATURE:
<223> OTHER INFORMATION: PHM1754-20-U forward primer

<400> SEQUENCE: 81
tgaagtygag cgagcattcg ttcacc                                        26

<210> SEQ ID NO 82
<211> LENGTH: 20
<212> TYPE: DNA
<213> ORGANISM: artificial
<220> FEATURE:
<223> OTHER INFORMATION: PHM1754-20-U reverse primer

<400> SEQUENCE: 82
ctggctgctg ggaagcttgt                                               20

<210> SEQ ID NO 83
<211> LENGTH: 25
<212> TYPE: DNA
<213> ORGANISM: artificial
<220> FEATURE:
<223> OTHER INFORMATION: PHM1754-20-U probe 1

<400> SEQUENCE: 83
cgcgccgagg caagccggag cattc                                         25

<210> SEQ ID NO 84
<211> LENGTH: 28
<212> TYPE: DNA
<213> ORGANISM: artificial
<220> FEATURE:
<223> OTHER INFORMATION: PHM1754-20-U probe 2

<400> SEQUENCE: 84
acggacgcgg agtaagccgg agcattca                                      28

<210> SEQ ID NO 85
<211> LENGTH: 20
<212> TYPE: DNA
<213> ORGANISM: artificial
<220> FEATURE:
<223> OTHER INFORMATION: PHM3951-25-U forward primer

<400> SEQUENCE: 85
aggaggacca gcaaccacca                                               20

<210> SEQ ID NO 86
<211> LENGTH: 19
<212> TYPE: DNA
<213> ORGANISM: artificial
<220> FEATURE:
<223> OTHER INFORMATION: PHM3951-25-U reverse primer

<400> SEQUENCE: 86
agctgaaact cggcgtggc                                                19

<210> SEQ ID NO 87
```

```
<210> SEQ ID NO 87
<211> LENGTH: 25
<212> TYPE: DNA
<213> ORGANISM: artificial
<220> FEATURE:
<223> OTHER INFORMATION: PHM3951-25-U probe 1

<400> SEQUENCE: 87
cgcgccgagg gccatttgcg tttgg                                              25

<210> SEQ ID NO 88
<211> LENGTH: 28
<212> TYPE: DNA
<213> ORGANISM: artificial
<220> FEATURE:
<223> OTHER INFORMATION: PHM3951-25-U probe 2

<400> SEQUENCE: 88
acggacgcgg agaccatttg cgtttgga                                           28

<210> SEQ ID NO 89
<211> LENGTH: 28
<212> TYPE: DNA
<213> ORGANISM: artificial
<220> FEATURE:
<223> OTHER INFORMATION: PHM1934-37-U forward primer

<400> SEQUENCE: 89
cttgactgtg tatggaggca acagtact                                           28

<210> SEQ ID NO 90
<211> LENGTH: 29
<212> TYPE: DNA
<213> ORGANISM: artificial
<220> FEATURE:
<223> OTHER INFORMATION: PHM1934-37-U reverse primer

<400> SEQUENCE: 90
agctttgtcc tgttgctccr tttctttcc                                          29

<210> SEQ ID NO 91
<211> LENGTH: 25
<212> TYPE: DNA
<213> ORGANISM: artificial
<220> FEATURE:
<223> OTHER INFORMATION: PHM1934-37-U probe 1

<400> SEQUENCE: 91
cgcgccgagg cggacaggac acagg                                              25

<210> SEQ ID NO 92
<211> LENGTH: 27
<212> TYPE: DNA
<213> ORGANISM: artificial
<220> FEATURE:
<223> OTHER INFORMATION: PHM1934-37-U probe 2

<400> SEQUENCE: 92
acggacgcgg agaggacagg acacagg                                            27

<210> SEQ ID NO 93
<211> LENGTH: 24
<212> TYPE: DNA
<213> ORGANISM: artificial
<220> FEATURE:
<223> OTHER INFORMATION: PHM4423-4-U forward primer

<400> SEQUENCE: 93
```

```
aggcaagaac cttgccaaaa tcgt                                          24

<210> SEQ ID NO 94
<211> LENGTH: 21
<212> TYPE: DNA
<213> ORGANISM: artificial
<220> FEATURE:
<223> OTHER INFORMATION: PHM4423-4-U reverse primer

<400> SEQUENCE: 94
tgggttcgct ctccacttcc t                                             21

<210> SEQ ID NO 95
<211> LENGTH: 27
<212> TYPE: DNA
<213> ORGANISM: artificial
<220> FEATURE:
<223> OTHER INFORMATION: PHM4423-4-U probe 1

<400> SEQUENCE: 95
cgcgccgagg accatagcct gatctcg                                       27

<210> SEQ ID NO 96
<211> LENGTH: 28
<212> TYPE: DNA
<213> ORGANISM: artificial
<220> FEATURE:
<223> OTHER INFORMATION: PHM4423-4-U probe 2

<400> SEQUENCE: 96
acggacgcgg aggccatagc ctgatctc                                      28

<210> SEQ ID NO 97
<211> LENGTH: 32
<212> TYPE: DNA
<213> ORGANISM: artificial
<220> FEATURE:
<223> OTHER INFORMATION: PHM9362-8-U forward primer

<400> SEQUENCE: 97
gtggcatcta tgtcaaacac tcaactactc aa                                 32

<210> SEQ ID NO 98
<211> LENGTH: 27
<212> TYPE: DNA
<213> ORGANISM: artificial
<220> FEATURE:
<223> OTHER INFORMATION: PHM9362-8-U reverse primer

<400> SEQUENCE: 98
tccagttgtt gtagtcttcc tgcacaa                                       27

<210> SEQ ID NO 99
<211> LENGTH: 29
<212> TYPE: DNA
<213> ORGANISM: artificial
<220> FEATURE:
<223> OTHER INFORMATION: PHM9362-8-U probe 1

<400> SEQUENCE: 99
cgcgccgagg tgcatttgtc caatgtatg                                     29

<210> SEQ ID NO 100
<211> LENGTH: 31
<212> TYPE: DNA
```

<213> ORGANISM: artificial
<220> FEATURE:
<223> OTHER INFORMATION: PHM9362-8-U probe 2

<400> SEQUENCE: 100
acggacgcgg agcgcatttg tccaatgtat g                                31

<210> SEQ ID NO 101
<211> LENGTH: 32
<212> TYPE: DNA
<213> ORGANISM: artificial
<220> FEATURE:
<223> OTHER INFORMATION: PHM1147-16-U forward primer

<400> SEQUENCE: 101
actaggtagc tcatttccag tatgtttcct gg                               32

<210> SEQ ID NO 102
<211> LENGTH: 25
<212> TYPE: DNA
<213> ORGANISM: artificial
<220> FEATURE:
<223> OTHER INFORMATION: PHM1147-16-U reverse primer

<400> SEQUENCE: 102
tggatcattg ccagagctgt gaaga                                       25

<210> SEQ ID NO 103
<211> LENGTH: 29
<212> TYPE: DNA
<213> ORGANISM: artificial
<220> FEATURE:
<223> OTHER INFORMATION: PHM1147-16-U probe 1

<400> SEQUENCE: 103
cgcgccgagg gttccttacc cattcatgt                                   29

<210> SEQ ID NO 104
<211> LENGTH: 33
<212> TYPE: DNA
<213> ORGANISM: artificial
<220> FEATURE:
<223> OTHER INFORMATION: PHM1147-16-U probe 2

<400> SEQUENCE: 104
acggacgcgg agattcctta cccattcatg tat                              33

<210> SEQ ID NO 105
<211> LENGTH: 26
<212> TYPE: DNA
<213> ORGANISM: artificial
<220> FEATURE:
<223> OTHER INFORMATION: PHM1147-19-U forward primer

<400> SEQUENCE: 105
agctctggca atgatccaat ggatgt                                      26

<210> SEQ ID NO 106
<211> LENGTH: 33
<212> TYPE: DNA
<213> ORGANISM: artificial
<220> FEATURE:
<223> OTHER INFORMATION: PHM1147-19-U reverse primer

<400> SEQUENCE: 106
acaaaacaat gctgaatgtt aagatttgca ggt                              33

<210> SEQ ID NO 107
<211> LENGTH: 25
<212> TYPE: DNA
<213> ORGANISM: artificial
<220> FEATURE:
<223> OTHER INFORMATION: PHM1147-19-U probe 1

<400> SEQUENCE: 107
cgcgccgagg cgcagagagg tcact                                         25

<210> SEQ ID NO 108
<211> LENGTH: 29
<212> TYPE: DNA
<213> ORGANISM: artificial
<220> FEATURE:
<223> OTHER INFORMATION: PHM1147-19-U probe 2

<400> SEQUENCE: 108
acggacgcgg agtgcagaga ggtcactac                                     29

<210> SEQ ID NO 109
<211> LENGTH: 13
<212> TYPE: DNA
<213> ORGANISM: artificial
<220> FEATURE:
<223> OTHER INFORMATION: PHM11850-3-U forward primer

<400> SEQUENCE: 109
gcgtggcccg cgc                                                      13

<210> SEQ ID NO 110
<211> LENGTH: 26
<212> TYPE: DNA
<213> ORGANISM: artificial
<220> FEATURE:
<223> OTHER INFORMATION: PHM11850-3-U reverse primer

<400> SEQUENCE: 110
cgtgtctagc aagacattgc tggact                                        26

<210> SEQ ID NO 111
<211> LENGTH: 32
<212> TYPE: DNA
<213> ORGANISM: artificial
<220> FEATURE:
<223> OTHER INFORMATION: PHM11850-3-U probe 1

<400> SEQUENCE: 111
cgcgccgagg tggtataatc cactacaatc tg                                 32

<210> SEQ ID NO 112
<211> LENGTH: 33
<212> TYPE: DNA
<213> ORGANISM: artificial
<220> FEATURE:
<223> OTHER INFORMATION: PHM11850-3-U probe 2

<400> SEQUENCE: 112
acggacgcgg agcggtataa tccactacaa tct                                33

<210> SEQ ID NO 113
<211> LENGTH: 19
<212> TYPE: DNA
<213> ORGANISM: artificial
<220> FEATURE:

-continued

<223> OTHER INFORMATION: PHM11850-6-U forward primer

<400> SEQUENCE: 113
tgctgccgat gctggatcg                                                    19

<210> SEQ ID NO 114
<211> LENGTH: 24
<212> TYPE: DNA
<213> ORGANISM: artificial
<220> FEATURE:
<223> OTHER INFORMATION: PHM11850-6-U reverse primer

<400> SEQUENCE: 114
tgcaagtgaa ctcaggtgcc atgt                                              24

<210> SEQ ID NO 115
<211> LENGTH: 26
<212> TYPE: DNA
<213> ORGANISM: artificial
<220> FEATURE:
<223> OTHER INFORMATION: PHM11850-6-U probe 1

<400> SEQUENCE: 115
cgcgccgagg actgctgagc acatag                                            26

<210> SEQ ID NO 116
<211> LENGTH: 28
<212> TYPE: DNA
<213> ORGANISM: artificial
<220> FEATURE:
<223> OTHER INFORMATION: PHM11850-6-U probe 2

<400> SEQUENCE: 116
acggacgcgg aggctgctga gcacatag                                          28

<210> SEQ ID NO 117
<211> LENGTH: 30
<212> TYPE: DNA
<213> ORGANISM: artificial
<220> FEATURE:
<223> OTHER INFORMATION: PHM9301-37-U forward primer

<400> SEQUENCE: 117
aatgcctggc aaaaataaac actggaaact                                        30

<210> SEQ ID NO 118
<211> LENGTH: 19
<212> TYPE: DNA
<213> ORGANISM: artificial
<220> FEATURE:
<223> OTHER INFORMATION: PHM9301-37-U reverse primer

<400> SEQUENCE: 118
agggcctccg agactgtgt                                                    19

<210> SEQ ID NO 119
<211> LENGTH: 29
<212> TYPE: DNA
<213> ORGANISM: artificial
<220> FEATURE:
<223> OTHER INFORMATION: PHM9301-37-U probe 1

<400> SEQUENCE: 119
cgcgccgagg accttctttc tttccttgc                                         29

```
<210> SEQ ID NO 120
<211> LENGTH: 30
<212> TYPE: DNA
<213> ORGANISM: artificial
<220> FEATURE:
<223> OTHER INFORMATION: PHM9301-37-U probe 2

<400> SEQUENCE: 120
acggacgcgg aggccttctt tctttccttg                                      30

<210> SEQ ID NO 121
<211> LENGTH: 20
<212> TYPE: DNA
<213> ORGANISM: artificial
<220> FEATURE:
<223> OTHER INFORMATION: PHM5280-41-U forward primer

<400> SEQUENCE: 121
cccttgctgc ttgccctagg                                                 20

<210> SEQ ID NO 122
<211> LENGTH: 28
<212> TYPE: DNA
<213> ORGANISM: artificial
<220> FEATURE:
<223> OTHER INFORMATION: PHM5280-41-U reverse primer

<400> SEQUENCE: 122
gctacatttc tacaaactgc cacctggg                                        28

<210> SEQ ID NO 123
<211> LENGTH: 29
<212> TYPE: DNA
<213> ORGANISM: artificial
<220> FEATURE:
<223> OTHER INFORMATION: PHM5280-41-U probe 1

<400> SEQUENCE: 123
cgcgccgagg gtttggtttg atcagtagc                                       29

<210> SEQ ID NO 124
<211> LENGTH: 32
<212> TYPE: DNA
<213> ORGANISM: artificial
<220> FEATURE:
<223> OTHER INFORMATION: PHM5280-41-U probe 2

<400> SEQUENCE: 124
acggacgcgg agatttggtt tgatcagtag ct                                   32

<210> SEQ ID NO 125
<211> LENGTH: 20
<212> TYPE: DNA
<213> ORGANISM: artificial
<220> FEATURE:
<223> OTHER INFORMATION: PHM13773-6-U forward primer

<400> SEQUENCE: 125
agtgktccga gccaaggcca                                                 20

<210> SEQ ID NO 126
<211> LENGTH: 20
<212> TYPE: DNA
<213> ORGANISM: artificial
<220> FEATURE:
<223> OTHER INFORMATION: PHM13773-6-U reverse primer
```

```
<400> SEQUENCE: 126
gccattcaac ggaccggtgt                                            20

<210> SEQ ID NO 127
<211> LENGTH: 25
<212> TYPE: DNA
<213> ORGANISM: artificial
<220> FEATURE:
<223> OTHER INFORMATION: PHM13773-6-U probe 1

<400> SEQUENCE: 127
cgcgccgagg tgtgttcaag ggctc                                      25

<210> SEQ ID NO 128
<211> LENGTH: 27
<212> TYPE: DNA
<213> ORGANISM: artificial
<220> FEATURE:
<223> OTHER INFORMATION: PHM13773-6-U probe 2

<400> SEQUENCE: 128
acggacgcgg agcgtgttca agggctc                                    27

<210> SEQ ID NO 129
<211> LENGTH: 26
<212> TYPE: DNA
<213> ORGANISM: artificial
<220> FEATURE:
<223> OTHER INFORMATION: PHM13773-11-U forward primer

<400> SEQUENCE: 129
cagacgatgg aaacacraac accggt                                     26

<210> SEQ ID NO 130
<211> LENGTH: 25
<212> TYPE: DNA
<213> ORGANISM: artificial
<220> FEATURE:
<223> OTHER INFORMATION: PHM13773-11-U reverse primer

<400> SEQUENCE: 130
cgtcctccgt rgagawggca gcttc                                      25

<210> SEQ ID NO 131
<211> LENGTH: 25
<212> TYPE: DNA
<213> ORGANISM: artificial
<220> FEATURE:
<223> OTHER INFORMATION: PHM13773-11-U probe 1

<400> SEQUENCE: 131
cgcgccgagg atggccattc aacgg                                      25

<210> SEQ ID NO 132
<211> LENGTH: 27
<212> TYPE: DNA
<213> ORGANISM: artificial
<220> FEATURE:
<223> OTHER INFORMATION: PHM13773-11-U probe 2

<400> SEQUENCE: 132
acggacgcgg aggtggccat tcaacgg                                    27

<210> SEQ ID NO 133
<211> LENGTH: 28
```

```
<212> TYPE: DNA
<213> ORGANISM: artificial
<220> FEATURE:
<223> OTHER INFORMATION: PHM16422-11-U forward primer

<400> SEQUENCE: 133
acaggttggt tggtatttac aagacgga                                    28

<210> SEQ ID NO 134
<211> LENGTH: 26
<212> TYPE: DNA
<213> ORGANISM: artificial
<220> FEATURE:
<223> OTHER INFORMATION: PHM16422-11-U reverse primer

<400> SEQUENCE: 134
cgctacacta ctttcatgct ctcggc                                      26

<210> SEQ ID NO 135
<211> LENGTH: 26
<212> TYPE: DNA
<213> ORGANISM: artificial
<220> FEATURE:
<223> OTHER INFORMATION: PHM16422-11-U probe 1

<400> SEQUENCE: 135
cgcgccgagg caacccagga agcttt                                      26

<210> SEQ ID NO 136
<211> LENGTH: 29
<212> TYPE: DNA
<213> ORGANISM: artificial
<220> FEATURE:
<223> OTHER INFORMATION: PHM16422-11-U probe 2

<400> SEQUENCE: 136
acggacgcgg agaaacccag gaagctttg                                   29

<210> SEQ ID NO 137
<211> LENGTH: 19
<212> TYPE: DNA
<213> ORGANISM: artificial
<220> FEATURE:
<223> OTHER INFORMATION: PHM9009-13-U forward primer

<400> SEQUENCE: 137
cagcccaggg ttgctcagt                                              19

<210> SEQ ID NO 138
<211> LENGTH: 28
<212> TYPE: DNA
<213> ORGANISM: artificial
<220> FEATURE:
<223> OTHER INFORMATION: PHM9009-13-U reverse primer

<400> SEQUENCE: 138
gcaatcttca aaatgctgag agcaacca                                    28

<210> SEQ ID NO 139
<211> LENGTH: 29
<212> TYPE: DNA
<213> ORGANISM: artificial
<220> FEATURE:
<223> OTHER INFORMATION: PHM9009-13-U probe 1

<400> SEQUENCE: 139
```
cgcgccgagg atttcgcaca ctcaaaatg                                   29

<210> SEQ ID NO 140
<211> LENGTH: 30
<212> TYPE: DNA
<213> ORGANISM: artificial
<220> FEATURE:
<223> OTHER INFORMATION: PHM9009-13-U probe 2

<400> SEQUENCE: 140
acggacgcgg aggtttcgca cactcaaaat                                  30

<210> SEQ ID NO 141
<211> LENGTH: 19
<212> TYPE: DNA
<213> ORGANISM: artificial
<220> FEATURE:
<223> OTHER INFORMATION: PHM3171-5-U forward primer

<400> SEQUENCE: 141
cgtcagcgcc cgttgaacc                                              19

<210> SEQ ID NO 142
<211> LENGTH: 28
<212> TYPE: DNA
<213> ORGANISM: artificial
<220> FEATURE:
<223> OTHER INFORMATION: PHM3171-5-U reverse primer

<400> SEQUENCE: 142
actcttcgct tgygaatccg agaagact                                    28

<210> SEQ ID NO 143
<211> LENGTH: 23
<212> TYPE: DNA
<213> ORGANISM: artificial
<220> FEATURE:
<223> OTHER INFORMATION: PHM3171-5-U probe 1

<400> SEQUENCE: 143
cgcgccgagg tgcctgaagc cgc                                         23

<210> SEQ ID NO 144
<211> LENGTH: 24
<212> TYPE: DNA
<213> ORGANISM: artificial
<220> FEATURE:
<223> OTHER INFORMATION: PHM3171-5-U probe 2

<400> SEQUENCE: 144
acggacgcgg agcgcctgaa gccg                                        24

<210> SEQ ID NO 145
<211> LENGTH: 28
<212> TYPE: DNA
<213> ORGANISM: artificial
<220> FEATURE:
<223> OTHER INFORMATION: PHM3860-43-U forward primer

<400> SEQUENCE: 145
gcagtgactg ctgaagacct grctaaca                                    28

<210> SEQ ID NO 146
<211> LENGTH: 28
<212> TYPE: DNA
<213> ORGANISM: artificial

```
<220> FEATURE:
<223> OTHER INFORMATION: PHM3860-43-U reverse primer

<400> SEQUENCE: 146
cgagatggtt caccaaatcg aaattgca                                    28

<210> SEQ ID NO 147
<211> LENGTH: 33
<212> TYPE: DNA
<213> ORGANISM: artificial
<220> FEATURE:
<223> OTHER INFORMATION: PHM3860-43-U probe 1

<400> SEQUENCE: 147
cgcgccgagg acaagtagat tcgttctata acg                              33

<210> SEQ ID NO 148
<211> LENGTH: 34
<212> TYPE: DNA
<213> ORGANISM: artificial
<220> FEATURE:
<223> OTHER INFORMATION: PHM3860-43-U probe 2

<400> SEQUENCE: 148
acggacgcgg aggcaagtag attcgttcta taac                             34

<210> SEQ ID NO 149
<211> LENGTH: 22
<212> TYPE: DNA
<213> ORGANISM: artificial
<220> FEATURE:
<223> OTHER INFORMATION: PHM7942-12-U forward primer

<400> SEQUENCE: 149
agctcaagga gctcatccgg aa                                          22

<210> SEQ ID NO 150
<211> LENGTH: 24
<212> TYPE: DNA
<213> ORGANISM: artificial
<220> FEATURE:
<223> OTHER INFORMATION: PHM7942-12-U reverse primer

<400> SEQUENCE: 150
cccatgagga agttgtccac cacc                                        24

<210> SEQ ID NO 151
<211> LENGTH: 23
<212> TYPE: DNA
<213> ORGANISM: artificial
<220> FEATURE:
<223> OTHER INFORMATION: PHM7942-12-U probe 1

<400> SEQUENCE: 151
cgcgccgagg gtcctcgcca gcg                                         23

<210> SEQ ID NO 152
<211> LENGTH: 25
<212> TYPE: DNA
<213> ORGANISM: artificial
<220> FEATURE:
<223> OTHER INFORMATION: PHM7942-12-U probe 2

<400> SEQUENCE: 152
acggacgcgg agatcctcgc cagcg                                       25
```

-continued

<210> SEQ ID NO 153
<211> LENGTH: 21
<212> TYPE: DNA
<213> ORGANISM: artificial
<220> FEATURE:
<223> OTHER INFORMATION: PHM678-22-U forward primer

<400> SEQUENCE: 153
aggagtagtc ctgcagcagc c                                          21

<210> SEQ ID NO 154
<211> LENGTH: 19
<212> TYPE: DNA
<213> ORGANISM: artificial
<220> FEATURE:
<223> OTHER INFORMATION: PHM678-22-U reverse primer

<400> SEQUENCE: 154
gctggcttct tcaccgcga                                             19

<210> SEQ ID NO 155
<211> LENGTH: 24
<212> TYPE: DNA
<213> ORGANISM: artificial
<220> FEATURE:
<223> OTHER INFORMATION: PHM678-22-U probe 1

<400> SEQUENCE: 155
cgcgccgagg gtctgcgtcg gttg                                       24

<210> SEQ ID NO 156
<211> LENGTH: 27
<212> TYPE: DNA
<213> ORGANISM: artificial
<220> FEATURE:
<223> OTHER INFORMATION: PHM678-22-U probe 2

<400> SEQUENCE: 156
acggacgcgg agttctgcgt cggttgt                                    27

<210> SEQ ID NO 157
<211> LENGTH: 18
<212> TYPE: DNA
<213> ORGANISM: artificial
<220> FEATURE:
<223> OTHER INFORMATION: PHM8358-17-U forward primer

<400> SEQUENCE: 157
ggccgtacgg gaacgtgc                                              18

<210> SEQ ID NO 158
<211> LENGTH: 21
<212> TYPE: DNA
<213> ORGANISM: artificial
<220> FEATURE:
<223> OTHER INFORMATION: PHM8358-17-U reverse primer

<400> SEQUENCE: 158
ccctgcctga aggtgaaggt g                                          21

<210> SEQ ID NO 159
<211> LENGTH: 24
<212> TYPE: DNA
<213> ORGANISM: artificial
<220> FEATURE:
<223> OTHER INFORMATION: PHM8358-17-U probe 1

-continued

<400> SEQUENCE: 159
cgcgccgagg gatgcgcaag gacg                                              24

<210> SEQ ID NO 160
<211> LENGTH: 26
<212> TYPE: DNA
<213> ORGANISM: artificial
<220> FEATURE:
<223> OTHER INFORMATION: PHM8358-17-U probe 2

<400> SEQUENCE: 160
acggacgcgg agcatgcgca aggacg                                            26

<210> SEQ ID NO 161
<211> LENGTH: 25
<212> TYPE: DNA
<213> ORGANISM: artificial
<220> FEATURE:
<223> OTHER INFORMATION: PHM16415-8-U forward primer

<400> SEQUENCE: 161
actatcagga agccacacca ttgga                                             25

<210> SEQ ID NO 162
<211> LENGTH: 28
<212> TYPE: DNA
<213> ORGANISM: artificial
<220> FEATURE:
<223> OTHER INFORMATION: PHM16415-8-U reverse primer

<400> SEQUENCE: 162
ytgtcyggyc tgttatctct gtgctggt                                          28

<210> SEQ ID NO 163
<211> LENGTH: 23
<212> TYPE: DNA
<213> ORGANISM: artificial
<220> FEATURE:
<223> OTHER INFORMATION: PHM16415-8-U probe 1

<400> SEQUENCE: 163
cgcgccgagg gcgcatctgg cac                                               23

<210> SEQ ID NO 164
<211> LENGTH: 26
<212> TYPE: DNA
<213> ORGANISM: artificial
<220> FEATURE:
<223> OTHER INFORMATION: PHM16415-8-U probe 2

<400> SEQUENCE: 164
acggacgcgg agacgcatct ggcact                                            26

<210> SEQ ID NO 165
<211> LENGTH: 33
<212> TYPE: DNA
<213> ORGANISM: artificial
<220> FEATURE:
<223> OTHER INFORMATION: PHM737-215-U forward primer

<400> SEQUENCE: 165
ccgttacatt acatgaagtg tggatgttga gtg                                    33

<210> SEQ ID NO 166

```
<211> LENGTH: 32
<212> TYPE: DNA
<213> ORGANISM: artificial
<220> FEATURE:
<223> OTHER INFORMATION: PHM737-215-U reverse primer

<400> SEQUENCE: 166
gactgataga ggacagatga aaggtacctc tc                               32

<210> SEQ ID NO 167
<211> LENGTH: 31
<212> TYPE: DNA
<213> ORGANISM: artificial
<220> FEATURE:
<223> OTHER INFORMATION: PHM737-215-U probe 1

<400> SEQUENCE: 167
cgcgccgagg gacctgaaca gaaacaatat g                                31

<210> SEQ ID NO 168
<211> LENGTH: 33
<212> TYPE: DNA
<213> ORGANISM: artificial
<220> FEATURE:
<223> OTHER INFORMATION: PHM737-215-U probe 2

<400> SEQUENCE: 168
acggacgcgg agaacctgaa cagaaacaat atg                              33

<210> SEQ ID NO 169
<211> LENGTH: 34
<212> TYPE: DNA
<213> ORGANISM: artificial
<220> FEATURE:
<223> OTHER INFORMATION: PHM9092-11-U forward primer

<400> SEQUENCE: 169
gcagtctata tgatccaccg agattaacac ttgt                             34

<210> SEQ ID NO 170
<211> LENGTH: 26
<212> TYPE: DNA
<213> ORGANISM: artificial
<220> FEATURE:
<223> OTHER INFORMATION: PHM9092-11-U reverse primer

<400> SEQUENCE: 170
tcagttacca ttgtgagcca rccagc                                      26

<210> SEQ ID NO 171
<211> LENGTH: 26
<212> TYPE: DNA
<213> ORGANISM: artificial
<220> FEATURE:
<223> OTHER INFORMATION: PHM9092-11-U probe 1

<400> SEQUENCE: 171
cgcgccgagg aacgagcatc agctca                                      26

<210> SEQ ID NO 172
<211> LENGTH: 27
<212> TYPE: DNA
<213> ORGANISM: artificial
<220> FEATURE:
<223> OTHER INFORMATION: PHM9092-11-U probe 2

<400> SEQUENCE: 172
```

```
acggacgcgg aggacgagca tcagctc                                          27
```

<210> SEQ ID NO 173
<211> LENGTH: 500
<212> TYPE: DNA
<213> ORGANISM: artificial
<220> FEATURE:
<223> OTHER INFORMATION: PHM10054 reference sequence

<400> SEQUENCE: 173

```
aaatgggaaa gtcccagtca cgacgagacg gacgacgtcc tgcccgacgg cacagccgtg       60
cgtgcagggt ggttcgtggc gtacaattca tatgggatgg ggcggatgga gtcggtgtgg      120
ggcgacgacg cgcgggaata ccggccggag cggtggctga accccagaga cggaacgttc      180
cggccggaca gcccctttcg gttcgtggca tttcacgcgg ggccgaggct ttgtctgggc      240
aaggaaatgg cgtacatcca gatgaagtcc atcgtggcgt gcgtgctgga ggagctcgac      300
gtggcggttg acgcgcgta ccggccccgg caggttgcgt cgctaacgct gcggatggcg       360
gacgggctac ctgtgaccgt gaagcagaga cgggactgac gagctgctgt cacaaacctg      420
caactccatc agccacccat gaagcctctg cagcagcaca aggcagcaaa gctgtttcac      480
caacttttcg agaaaagtgg                                                  500
```

<210> SEQ ID NO 174
<211> LENGTH: 718
<212> TYPE: DNA
<213> ORGANISM: artificial
<220> FEATURE:
<223> OTHER INFORMATION: PHM10721 reference sequence

<400> SEQUENCE: 174

```
atccttgtta atggcagatc ctttggaaaa caagatgcta gctcggcttt tccaggatac       60
aacctggaaa cgggcaatg ggcatattaa tctgtacaga gcatctgaag aaggtttctc       120
acacaggaac aggatcatcc ctagtccagc aaatgttcac gtgacaagaa acgcccagct      180
atctgcattt cctcaggttt tcattcgacg cccttgaaca gcttcaagtg ctttcctatg      240
tcgattatac tagtttctgc catggcagag aggagttatc tggaacgagg agctttgcag      300
catcgcttca gatagaaatg ctggtagcct ggtagcatag attttttcgt gtcttttaat      360
tttcacattc atcgttatgt tttgcacttc tcctgcagct gtactcaatt ttgtgagatt      420
tttcaagtcc cattttgaca ttgcagattc aatgaaagtg gagtgacatt gtggcaactg      480
acaagccggc agtttaatgg tgatcaactc tgaaagtctt gacaagttgg gttgctactg      540
aggtgccttt tcaagttgca gtggtagcac gacttctctt gggatgagct agttaacttt      600
tggtatttga gaggaaatga ggaattctgg tgtgtccacc catcctgtac agttattaga      660
ataactaatc aaaggagtac tgtgaaattc ttgcgatctg tgaaaattt ctatataa         718
```

<210> SEQ ID NO 175
<211> LENGTH: 690
<212> TYPE: DNA
<213> ORGANISM: artificial
<220> FEATURE:
<223> OTHER INFORMATION: PHM15661 reference sequence

<400> SEQUENCE: 175

```
ggggataagg gaaagagggg cctcatggtt gggcccaatt tgagtttgtc cagcgtggca       60
gtcaaaacca ctgaaaccag cattaaaggg gtgcgcggta gccaaatatg tctggtttac      120
```

```
acaattgaat ggccaaatgt ttctggtctt cgggttcagt gaccgaaacc aaactcggac    180
cataattcta tgggcacaat gatcttctcc ctttcttaaa tgccagtggc tgggagctgt    240
atgcactcct ttttggaatt ttagatttga tctcgcaccc ttgattttttg agaaacttat    300
```

```
atgcactcct ttttggaatt ttagatttga tctcgcaccc ttgattttttg agaaacttat    300 gtgagacatt cctaattctt gcaggagaag cttaaagcgc tcgaggatga aaatcaaat     360 ggaaattggt acaaggatta aaggctgaaa cttctctctc tttctgactg ctgatgtaag    420
gttacttgtg agctgccgtt aggccccctta cagaatacca actctgattg ccggtgtaat   480
gttctccata ttttttttcc agataatttg gtggtaacct gataggacga caactaaaga   540
ggtattcata tacggtatta gacttttgtc cgagggggta aaattgtatc ataggatttg    600
acatggttga cggctacaga ttcttcttcc agttgtgctg ctgtgctgtg ttgtctttct    660
tccctcttcg gctgtctagg gaaaataaca                                     690
```

<210> SEQ ID NO 176  
<211> LENGTH: 513  
<212> TYPE: DNA  
<213> ORGANISM: artificial  
<220> FEATURE:  
<223> OTHER INFORMATION: PHM12872 reference sequence

<400> SEQUENCE: 176

```
gcacgcacca ccaatataag gagtatggta gcaaggctga tgcaaggcct ctggcagata     60
ttatcgagac gtcgccacaa atgcttatgg aatgcttgaa ggcattctat ggtattgtga    120
ctggaacaga aggttccttg cctgaatttg agcaactgca ggttccaagg ttacgttcag    180
atgcctgcaa tggtttggca agagctctag cagaatctta tgagctcatt tacagcgcag    240
tcatggatcc gaataacagt tatcctgacc caaggtcttt ggttaagcac tctcctgaac    300
agataagaac tatactggaa gcctgaggtc ttcgcacgat gccttatggt acatgttaag    360
tagaggtctt ggttaagcac tctcctgcat gaaactttgt catgtaaatt tccgactaca    420
agctgtgggt tcaattgatt acagaaatat ggaagcggtg actctctgaa ctcatgtatc    480
ggtatctagt atggtcatag ctgccttccc ccc                                 513
```

<210> SEQ ID NO 177  
<211> LENGTH: 26  
<212> TYPE: DNA  
<213> ORGANISM: artificial  
<220> FEATURE:  
<223> OTHER INFORMATION: PHM8711-17-U forward primer

<400> SEQUENCE: 177

```
gcatgtgcca cctgttagtt tttgca                                          26
```

<210> SEQ ID NO 178  
<211> LENGTH: 34  
<212> TYPE: DNA  
<213> ORGANISM: artificial  
<220> FEATURE:  
<223> OTHER INFORMATION: PHM8711-17-U reverse primer

<400> SEQUENCE: 178

```
cgctccagcc ttgatattca acttaacyga taca                                 34
```

<210> SEQ ID NO 179  
<211> LENGTH: 28  
<212> TYPE: DNA  
<213> ORGANISM: artificial  
<220> FEATURE:  
<223> OTHER INFORMATION: PHM8711-17-U probe 1

```
<400> SEQUENCE: 179
cgcgccgagg acaaacaggt gaacaaca                                          28

<210> SEQ ID NO 180
<211> LENGTH: 29
<212> TYPE: DNA
<213> ORGANISM: artificial
<220> FEATURE:
<223> OTHER INFORMATION: PHM8711-17-U probe 2

<400> SEQUENCE: 180
acggacgcgg aggcaaacag gtgaacaac                                         29

<210> SEQ ID NO 181
<211> LENGTH: 19
<212> TYPE: DNA
<213> ORGANISM: artificial
<220> FEATURE:
<223> OTHER INFORMATION: PHM10054-14-U forward primer

<400> SEQUENCE: 181
tcgtggcatt tcacgcggg                                                    19

<210> SEQ ID NO 182
<211> LENGTH: 20
<212> TYPE: DNA
<213> ORGANISM: artificial
<220> FEATURE:
<223> OTHER INFORMATION: PHM10054-14-U reverse primer

<400> SEQUENCE: 182
gcacgccacg atggacttca                                                   20

<210> SEQ ID NO 183
<211> LENGTH: 25
<212> TYPE: DNA
<213> ORGANISM: artificial
<220> FEATURE:
<223> OTHER INFORMATION: PHM10054-14-U probe 1

<400> SEQUENCE: 183
cgcgccgagg ctccttgccc agaca                                             25

<210> SEQ ID NO 184
<211> LENGTH: 27
<212> TYPE: DNA
<213> ORGANISM: artificial
<220> FEATURE:
<223> OTHER INFORMATION: PHM10054-14-U probe 2

<400> SEQUENCE: 184
acggacgcgg agttccttgc ccagaca                                           27

<210> SEQ ID NO 185
<211> LENGTH: 35
<212> TYPE: DNA
<213> ORGANISM: artificial
<220> FEATURE:
<223> OTHER INFORMATION: PHM10721-9-U forward primer

<400> SEQUENCE: 185
gctggtagcc tkgtagcata gawttttcg tgtct                                   35

<210> SEQ ID NO 186
```

```
<211> LENGTH: 35
<212> TYPE: DNA
<213> ORGANISM: artificial
<220> FEATURE:
<223> OTHER INFORMATION: PHM10721-9-U reverse primer

<400> SEQUENCE: 186
actccacttk cattgaatct gcaatgtcaa aatgg                               35

<210> SEQ ID NO 187
<211> LENGTH: 26
<212> TYPE: DNA
<213> ORGANISM: artificial
<220> FEATURE:
<223> OTHER INFORMATION: PHM10721-9-U probe 1

<400> SEQUENCE: 187
cgcgccgagg ttgagtacag ctgcag                                        26

<210> SEQ ID NO 188
<211> LENGTH: 28
<212> TYPE: DNA
<213> ORGANISM: artificial
<220> FEATURE:
<223> OTHER INFORMATION: PHM10721-9-U probe 2

<400> SEQUENCE: 188
acggacgcgg agctgagtac agctgcag                                      28

<210> SEQ ID NO 189
<211> LENGTH: 29
<212> TYPE: DNA
<213> ORGANISM: artificial
<220> FEATURE:
<223> OTHER INFORMATION: PHM10721-16-U forward primer

<400> SEQUENCE: 189
actgacaagc cggcagttta atgktgatc                                     29

<210> SEQ ID NO 190
<211> LENGTH: 26
<212> TYPE: DNA
<213> ORGANISM: artificial
<220> FEATURE:
<223> OTHER INFORMATION: PHM10721-16-U reverse primer

<400> SEQUENCE: 190
cgtgctacca ctgcaacttg aaaagg                                        26

<210> SEQ ID NO 191
<211> LENGTH: 27
<212> TYPE: DNA
<213> ORGANISM: artificial
<220> FEATURE:
<223> OTHER INFORMATION: PHM10721-16-U probe 1

<400> SEQUENCE: 191
cgcgccgagg aagttgggtt gctactg                                       27

<210> SEQ ID NO 192
<211> LENGTH: 29
<212> TYPE: DNA
<213> ORGANISM: artificial
<220> FEATURE:
<223> OTHER INFORMATION: PHM10721-16-U probe 2

<400> SEQUENCE: 192
```

```
acggacgcgg aggagttggg ttgctactg                                     29

<210> SEQ ID NO 193
<211> LENGTH: 30
<212> TYPE: DNA
<213> ORGANISM: artificial
<220> FEATURE:
<223> OTHER INFORMATION: PHM15661-21-U forward primer

<400> SEQUENCE: 193
ccaactctga ttgcyggtgt aatgttctcc                                    30

<210> SEQ ID NO 194
<211> LENGTH: 35
<212> TYPE: DNA
<213> ORGANISM: artificial
<220> FEATURE:
<223> OTHER INFORMATION: PHM15661-21-U reverse primer

<400> SEQUENCE: 194
catgtcaaat cctatgatac aattttaccc cctcg                              35

<210> SEQ ID NO 195
<211> LENGTH: 30
<212> TYPE: DNA
<213> ORGANISM: artificial
<220> FEATURE:
<223> OTHER INFORMATION: PHM15661-21-U probe 1

<400> SEQUENCE: 195
cgcgccgagg tttagttgtc gtcctatcag                                    30

<210> SEQ ID NO 196
<211> LENGTH: 32
<212> TYPE: DNA
<213> ORGANISM: artificial
<220> FEATURE:
<223> OTHER INFORMATION: PHM15661-21-U probe 2

<400> SEQUENCE: 196
acggacgcgg agcttagttg tcgtcctatc ag                                 32
```